US011965882B2

(12) United States Patent
Stadler

(10) Patent No.: US 11,965,882 B2
(45) Date of Patent: Apr. 23, 2024

(54) METHODS OF ISOLATING A BIOLOGICAL ENTITY

(71) Applicant: Cell.Copedia GmbH, Leipzig (DE)

(72) Inventor: Herbert Stadler, Niemetal/Ellershausen (DE)

(73) Assignee: CELL.COPEDIA GMBH, Liepzig (DE)

( * ) Notice: Subject to any disclaimer, the term of this patent is extended or adjusted under 35 U.S.C. 154(b) by 0 days.

(21) Appl. No.: 17/758,412

(22) PCT Filed: Feb. 1, 2021

(86) PCT No.: PCT/EP2021/052331
§ 371 (c)(1),
(2) Date: Jul. 6, 2022

(87) PCT Pub. No.: WO2021/152178
PCT Pub. Date: Aug. 5, 2021

(65) Prior Publication Data
US 2023/0140446 A1    May 4, 2023

(30) Foreign Application Priority Data
Jan. 31, 2020 (EP) .................................. 20154816

(51) Int. Cl.
*G01N 33/548* (2006.01)
*G01N 33/543* (2006.01)
(Continued)

(52) U.S. Cl.
CPC . *G01N 33/54353* (2013.01); *G01N 33/54366* (2013.01); *G01N 33/548* (2013.01);
(Continued)

(58) Field of Classification Search
CPC ....... G01N 33/54353; G01N 33/54366; G01N 33/548; G01N 33/56966; G01N 2333/70596; G01N 2458/00
See application file for complete search history.

(56) References Cited

U.S. PATENT DOCUMENTS

2003/0119070 A1*  6/2003  Schaeffer ............... A61P 35/00
                                                        530/391.1
2017/0361314 A1   12/2017  Stadler et al.

FOREIGN PATENT DOCUMENTS

WO    199711183 A1    3/1997
WO    200190153 A2    11/2001
(Continued)

OTHER PUBLICATIONS

Schmidt et al. The Strep-tag system for one-step purification and high-affinity detection or capturing of proteins. Nature Protocols 2 (6): 1528-1535 (2007).*
(Continued)

*Primary Examiner* — Gailene Gabel
(74) *Attorney, Agent, or Firm* — MH2 TECHNOLOGY LAW GROUP, LLP

(57) ABSTRACT

Provided are affinity-based methods of isolating biological entities via a surface antigen from a sample with non-chromatographic and chromatographic methods being provided. Also provided is a dextran polymer, kits for use in the method of isolating a biological entity and an apparatus for performing the methods.

20 Claims, 21 Drawing Sheets
Specification includes a Sequence Listing.

(51) Int. Cl.
 *G01N 33/569* (2006.01)
 *C08B 37/02* (2006.01)
(52) U.S. Cl.
 CPC .... *G01N 33/56966* (2013.01); *C08B 37/0021* (2013.01); *G01N 2333/70596* (2013.01); *G01N 2458/00* (2013.01)

(56) References Cited

FOREIGN PATENT DOCUMENTS

WO 2013124474 A2 8/2013
WO 2015166049 A1 11/2015

OTHER PUBLICATIONS

Korndorfer et al. Improved affinity of engineered streptavidin for the Strep-tag II peptide is due to a fixed open conformation of the lid-like loop of the binding site. Protein Science 11: 883-893 (2002).*
Werther, K. et al., "The use of the CELLection Kit™ in the isolation of carcinoma cells from mononuclear cell suspensions", Journal of Immunological Methods, 2000, vol. 238, No. 1-2, pp. 133-141.
International Search Report and Written Opinion of the International Searching Authority for PCT/EP2021/052331 dated Apr. 6, 2021, 12 pages.
International Preliminary Report on Patentability (PCT Article 36 and Rule 70) for PCT/EP2021/052331 dated Nov. 24, 2021 with Amended Sheets attached, 22 pages.

* cited by examiner

C

Program

(Velocity sample uptake: 0.48 ml/min, Velocity sample release: 0.39 ml/min)

| Step | Posit. | Flow (1 up; 0 down) | Syringe dist. (cor. Volume) | | pause | | | Time (sec) | |
|---|---|---|---|---|---|---|---|---|---|
| 1 | 1 | 1 | 1626 | 1219 | 10 | 0 | 2100 | 80 | 5038 |
| 2 | 1 | 0 | 1626 | 1219 | 0 | 0 | 5300 | 80 | 8228 |
| 3 | 1 | 1 | 1626 | 1219 | 10 | 0 | 2100 | 80 | 5040 |
| 4 | 1 | 0 | 1626 | 1219 | 0 | 0 | 5300 | 80 | 8230 |
| 5 | 5 | 1 | 3048 | 3048 | 20 | 0 | 2100 | 60 | 8287 |
| 6 | 2 | 1 | 2032 | 508 | 0 | 0 | 2100 | 240 | 4889 |
| 7 | 3 | 0 | 2286 | 457 | 0 | 0 | 5300 | 300 | 8353 |
| 8 | 2 | 1 | 2032 | 508 | 0 | 0 | 2100 | 240 | 4891 |
| 9 | 3 | 0 | 2286 | 457 | 0 | 0 | 5300 | 300 | 8355 |
| 10 | 2 | 1 | 2032 | 508 | 0 | 0 | 2100 | 240 | 4893 |
| 11 | 3 | 0 | 2286 | 457 | 0 | 0 | 5300 | 300 | 8357 |
| 12 | 3 | 1 | 2032 | 508 | 0 | 0 | 2100 | 240 | 4896 |
| 13 | 4 | 0 | 2286 | 457 | 0 | 0 | 5300 | 300 | 8360 |
| 14 | 3 | 1 | 2032 | 508 | 0 | 0 | 2100 | 240 | 4898 |
| 15 | 4 | 0 | 2286 | 457 | 0 | 0 | 5300 | 300 | 8362 |
| 16 | 3 | 1 | 2032 | 508 | 0 | 0 | 2100 | 240 | 4900 |
| 17 | 4 | 0 | 3810 | 762 | 0 | 0 | 5300 | 300 | 10193 |
| 18 | 1 | 1 | 25 | 762 | 0 | 0 | 2100 | 2 | 2909 |
| 19 | 1 | 0 | 25 | 762 | 0 | 0 | 5300 | 2 | 6109 |
| 20 | 5 | 1 | 1524 | 610 | 10 | 0 | 2100 | 150 | 4420 |
| 21 | 5 | 0 | 1524 | 3048 | 0 | 0 | 5300 | 30 | 9928 |
| 22 | 6 | 1 | 2540 | 635 | 10 | 0 | 2100 | 240 | 5554 |
| 23 | 6 | 0 | 2540 | 3048 | 0 | 0 | 5300 | 50 | 10967 |
| 24 | 7 | 1 | 4064 | 610 | 10 | 0 | 2100 | 400 | 7216 |
| 25 | 7 | 0 | 4064 | 3048 | 0 | 0 | 5300 | 80 | 12524 |
| 26 | 8 | 1 | 254 | 7620 | 0 | 0 | 2100 | 2 | 10011 |
| 27 | 8 | 0 | 254 | 7620 | 0 | 0 | 5300 | 2 | 13211 |
| 28 | 9 | 1 | 5080 | 1129 | 60 | 0 | 2100 | 270 | 8677 |
| 29 | 10 | 0 | 5080 | 7620 | 0 | 0 | 5300 | 40 | 18079 |
| 30 | 11 | 1 | 5080 | 3048 | 0 | 0 | 2100 | 100 | 10370 |
| 31 | 10 | 0 | 5080 | 10160 | 0 | 0 | 5300 | 30 | 20611 |
| 32 | 11 | 1 | 2540 | 7620 | 60 | 0 | 2100 | 20 | 12384 |
| 33 | 10 | 0 | 2540 | 15240 | 0 | 0 | 5300 | 10 | 23133 |
| END | | | | | | | | | |

| Position | Content | Volume [mL] |
|---|---|---|
| 1 | Fab in Buffer Cl | 4.2 |
| 2 | Sample | 12.5 |
| 3 | - | 0.0 |
| 4 | - | 0.0 |
| 5 | Buffer Cl | 15.0 |
| 6 | Buffer Cl | 10.0 |
| 7 | Buffer Cl | 10.0 |
| 8 | Buffer Cl | 5.0 |
| 9 | 1 mM Biotin | 10.0 |
| 10 | - | 0.0 |
| 11 | 1 mM Biotin | 15.0 |

B

Program

(Velocity sample uptake: 1.84 ml/min, Velocity sample release: 0.74 ml/min (1.59 ml/min for fast release))

| Step | Posit. | Flow (1 up; 0 down) | Syringe dist. (Volume) | | pause | | | Time (sec) | |
|---|---|---|---|---|---|---|---|---|---|
| 1 | 1 | 1 | 1626 | 1219 | 10 | 0 | 2100 | 80 | 5038 |
| 2 | 1 | 0 | 1626 | 1219 | 0 | 0 | 5300 | 80 | 8228 |
| 3 | 1 | 1 | 1626 | 1219 | 10 | 0 | 2100 | 80 | 5040 |
| 4 | 1 | 0 | 1626 | 1219 | 0 | 0 | 5300 | 80 | 8230 |
| 5 | 5 | 1 | 2540 | 2540 | 20 | 0 | 2100 | 60 | 7271 |
| 6 | 2 | 1 | 1270 | 318 | 0 | 0 | 2100 | 80 | 3937 |
| 7 | 3 | 0 | 1524 | 381 | 0 | 0 | 5300 | 240 | 7455 |
| 8 | 2 | 1 | 1270 | 318 | 0 | 0 | 2100 | 80 | 3939 |
| 9 | 3 | 0 | 1524 | 381 | 0 | 0 | 5300 | 240 | 7457 |
| 10 | 2 | 1 | 1270 | 318 | 0 | 0 | 2100 | 80 | 3941 |
| 11 | 3 | 0 | 3302 | 826 | 0 | 0 | 5300 | 240 | 9682 |
| 12 | 1 | 1 | 25 | 762 | 0 | 0 | 2100 | 2 | 2903 |
| 13 | 1 | 0 | 25 | 762 | 0 | 0 | 5300 | 2 | 6103 |
| 14 | 5 | 1 | 1524 | 610 | 10 | 0 | 2100 | 150 | 4414 |
| 15 | 5 | 0 | 1524 | 3048 | 0 | 0 | 5300 | 30 | 9922 |
| 16 | 6 | 1 | 2540 | 635 | 10 | 0 | 2100 | 240 | 5548 |
| 17 | 6 | 0 | 2540 | 3048 | 0 | 0 | 5300 | 50 | 10961 |
| 18 | 7 | 1 | 4064 | 610 | 10 | 0 | 2100 | 400 | 7210 |
| 19 | 7 | 0 | 4064 | 3048 | 0 | 0 | 5300 | 80 | 12518 |
| 20 | 8 | 1 | 254 | 7620 | 0 | 0 | 2100 | 2 | 10005 |
| 21 | 8 | 0 | 254 | 7620 | 0 | 0 | 5300 | 2 | 13205 |
| 22 | 9 | 1 | 2540 | 1270 | 0 | 0 | 2100 | 80 | 6062 |
| 23 | 10 | 0 | 2540 | 2540 | 0 | 0 | 5300 | 60 | 10473 |
| 24 | 11 | 1 | 2540 | 1270 | 0 | 0 | 2100 | 80 | 6066 |
| 25 | 10 | 0 | 2540 | 2540 | 0 | 0 | 5300 | 60 | 10475 |
| END | | | | | | | | | |

| Position | Volumes |
|---|---|
| 1 | 4.2 mL Buffer Cl + 22.5 µg CD81-Fab-Strep |
| 2 | 4.25 mL Buffy Coat + 4.25 mL Buffer Cl |
| 3 | - |
| 4 | - |
| 5 | 9 mL Buffer Cl |
| 6 | 6 mL Buffer Cl |
| 7 | 9 mL Buffer Cl |
| 8 | 2 mL Buffer Cl |
| 9 | 6 mL 1mM Biotin |
| 10 | - |
| 11 | 6 mL 1mM Biotin |

A

B

SEQUENCE LISTING

```
<160> NUMBER OF SEQ ID NOS: 26

<210> SEQ ID NO 1
<211> LENGTH: 8
<212> TYPE: PRT
<213> ORGANISM: Artificial
<220> FEATURE:
<223> OTHER INFORMATION: streptavidin-binding peptide
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (7)..(7)
<223> OTHER INFORMATION: X is Gly or Glu
<220> FEATURE:
<221> NAME/KEY: MISC_FEATURE
<222> LOCATION: (8)..(8)
<223> OTHER INFORMATION: X is Gly, Lys or Arg

<400> SEQUENCE: 1

Trp Xaa His Pro Gln Phe Xaa Xaa
1               5

<210> SEQ ID NO 2
<211> LENGTH: 8
<212> TYPE: PRT
<213> ORGANISM: Artificial
<220> FEATURE:
<223> OTHER INFORMATION: streptavidin-binding peptide

<400> SEQUENCE: 2

Trp Arg His Pro Gln Phe Gly Gly
1               5

<210> SEQ ID NO 3
<211> LENGTH: 8
<212> TYPE: PRT
<213> ORGANISM: Artificial
<220> FEATURE:
<223> OTHER INFORMATION: streptavidin-binding peptide

<400> SEQUENCE: 3

Trp Ser His Pro Gln Phe Glu Lys
1               5

<210> SEQ ID NO 4
<211> LENGTH: 4
<212> TYPE: PRT
<213> ORGANISM: Artificial
<220> FEATURE:
<223> OTHER INFORMATION: streptavidin-binding peptide

<400> SEQUENCE: 4

His Pro Gln Phe
1

<210> SEQ ID NO 5
<211> LENGTH: 8
<212> TYPE: PRT
<213> ORGANISM: Artificial
<220> FEATURE:
<223> OTHER INFORMATION: streptavidin-binding peptide
<220> FEATURE:
<221> NAME/KEY: MISC_FEATURE
<222> LOCATION: (1)..(1)
<223> OTHER INFORMATION: X is Trp, Lys or Arg
<220> FEATURE:
<221> NAME/KEY: MISC_FEATURE
```

```
<222> LOCATION: (2)..(2)
<223> OTHER INFORMATION: X is any amino acid
<220> FEATURE:
<221> NAME/KEY: MISC_FEATURE
<222> LOCATION: (7)..(7)
<223> OTHER INFORMATION: X is Gly or Glu
<220> FEATURE:
<221> NAME/KEY: MISC_FEATURE
<222> LOCATION: (8)..(8)
<223> OTHER INFORMATION: X is Gly, Lys or Arg

<400> SEQUENCE: 5

Xaa Xaa His Pro Gln Phe Xaa Xaa
1               5

<210> SEQ ID NO 6
<211> LENGTH: 8
<212> TYPE: PRT
<213> ORGANISM: Artificial
<220> FEATURE:
<223> OTHER INFORMATION: streptavidin-binding peptide
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (7)..(7)
<223> OTHER INFORMATION: X is Gly or Glu
<220> FEATURE:
<221> NAME/KEY: MISC_FEATURE
<222> LOCATION: (8)..(8)
<223> OTHER INFORMATION: X is Gly, Lys or Arg

<400> SEQUENCE: 6

Trp Xaa His Pro Gln Phe Xaa Xaa
1               5

<210> SEQ ID NO 7
<211> LENGTH: 8
<212> TYPE: PRT
<213> ORGANISM: Artificial
<220> FEATURE:
<223> OTHER INFORMATION: streptavidin-binding peptide

<400> SEQUENCE: 7

Trp Ser His Pro Gln Phe Glu Lys
1               5

<210> SEQ ID NO 8
<211> LENGTH: 28
<212> TYPE: PRT
<213> ORGANISM: Artificial
<220> FEATURE:
<223> OTHER INFORMATION: streptavidin-binding peptide
<220> FEATURE:
<221> NAME/KEY: MISC_FEATURE
<222> LOCATION: (9)..(20)
<223> OTHER INFORMATION: X is any amino acid an up to 12 may be absent

<400> SEQUENCE: 8

Trp Ser His Pro Gln Phe Glu Lys Xaa Xaa Xaa Xaa Xaa Xaa Xaa Xaa
1               5                   10                  15

Xaa Xaa Xaa Xaa Trp Ser His Pro Gln Phe Glu Lys
            20                  25

<210> SEQ ID NO 9
<211> LENGTH: 8
<212> TYPE: PRT
<213> ORGANISM: Artificial
```

```
<220> FEATURE:
<223> OTHER INFORMATION: streptavidin-binding peptide

<400> SEQUENCE: 9

Trp Ser His Pro Gln Phe Glu Lys
1               5

<210> SEQ ID NO 10
<211> LENGTH: 28
<212> TYPE: PRT
<213> ORGANISM: Artificial
<220> FEATURE:
<223> OTHER INFORMATION: streptavidin-binding peptide

<400> SEQUENCE: 10

Trp Ser His Pro Gln Phe Glu Lys Gly Gly Gly Ser Gly Gly Gly Ser
1               5                   10                  15

Gly Gly Gly Ser Trp Ser His Pro Gln Phe Glu Lys
            20                  25

<210> SEQ ID NO 11
<211> LENGTH: 24
<212> TYPE: PRT
<213> ORGANISM: Artificial
<220> FEATURE:
<223> OTHER INFORMATION: streptavidin-binding peptide

<400> SEQUENCE: 11

Trp Ser His Pro Gln Phe Glu Lys Gly Gly Gly Ser Gly Gly Gly Ser
1               5                   10                  15

Trp Ser His Pro Gln Phe Glu Lys
            20

<210> SEQ ID NO 12
<211> LENGTH: 28
<212> TYPE: PRT
<213> ORGANISM: Artificial
<220> FEATURE:
<223> OTHER INFORMATION: streptavidin-binding peptide

<400> SEQUENCE: 12

Trp Ser His Pro Gln Phe Glu Lys Gly Gly Gly Ser Gly Gly Gly Ser
1               5                   10                  15

Gly Gly Ser Ala Trp Ser His Pro Gln Phe Glu Lys
            20                  25

<210> SEQ ID NO 13
<211> LENGTH: 4
<212> TYPE: PRT
<213> ORGANISM: Artificial
<220> FEATURE:
<223> OTHER INFORMATION: streptavidin mutein fragment

<400> SEQUENCE: 13

Val Thr Ala Arg
1

<210> SEQ ID NO 14
<211> LENGTH: 4
<212> TYPE: PRT
<213> ORGANISM: Artificial
<220> FEATURE:
<223> OTHER INFORMATION: streptavidin mutein fragment

<400> SEQUENCE: 14
```

Ile Gly Ala Arg
1

<210> SEQ ID NO 15
<211> LENGTH: 9
<212> TYPE: PRT
<213> ORGANISM: Artificial
<220> FEATURE:
<223> OTHER INFORMATION: HA-tag

<400> SEQUENCE: 15

Tyr Pro Tyr Asp Val Pro Asp Tyr Ala
1               5

<210> SEQ ID NO 16
<211> LENGTH: 11
<212> TYPE: PRT
<213> ORGANISM: Artificial
<220> FEATURE:
<223> OTHER INFORMATION: VSV-G-tag

<400> SEQUENCE: 16

Tyr Thr Asp Ile Glu Met Asn Arg Leu Gly Lys
1               5                   10

<210> SEQ ID NO 17
<211> LENGTH: 11
<212> TYPE: PRT
<213> ORGANISM: Artificial
<220> FEATURE:
<223> OTHER INFORMATION: HSV-tag

<400> SEQUENCE: 17

Gln Pro Glu Leu Ala Pro Glu Asp Pro Glu Asp
1               5                   10

<210> SEQ ID NO 18
<211> LENGTH: 10
<212> TYPE: PRT
<213> ORGANISM: Artificial
<220> FEATURE:
<223> OTHER INFORMATION: T7 epitope

<400> SEQUENCE: 18

Ala Ser Met Thr Gly Gly Gln Gln Met Gly
1               5                   10

<210> SEQ ID NO 19
<211> LENGTH: 10
<212> TYPE: PRT
<213> ORGANISM: Artificial
<220> FEATURE:
<223> OTHER INFORMATION: myc epitope of c-myc

<400> SEQUENCE: 19

Glu Gln Lys Leu Ile Ser Glu Glu Asp Leu
1               5                   10

<210> SEQ ID NO 20
<211> LENGTH: 14
<212> TYPE: PRT
<213> ORGANISM: Artificial
<220> FEATURE:
<223> OTHER INFORMATION: V5 tag

<400> SEQUENCE: 20

Gly Lys Pro Ile Pro Asn Pro Leu Leu Gly Leu Asp Ser Thr

<210> SEQ ID NO 21
<211> LENGTH: 7
<212> TYPE: PRT
<213> ORGANISM: Artificial Sequence
<220> FEATURE:
<223> OTHER INFORMATION: streptavidin-binding peptide
<220> FEATURE:
<221> NAME/KEY: MISC_FEATURE
<222> LOCATION: (3)..(3)
<223> OTHER INFORMATION: X is Gln, Asn, or Met
<220> FEATURE:
<221> NAME/KEY: MISC_FEATURE
<222> LOCATION: (4)..(4)
<223> OTHER INFORMATION: X can be 0-50 amino acids of any type
<220> FEATURE:
<221> NAME/KEY: MISC_FEATURE
<222> LOCATION: (7)..(7)
<223> OTHER INFORMATION: X is Gln, Asn, or Met

<400> SEQUENCE: 21

His Pro Xaa Xaa His Pro Xaa
1               5

<210> SEQ ID NO 22
<211> LENGTH: 7
<212> TYPE: PRT
<213> ORGANISM: Artificial Sequence
<220> FEATURE:
<223> OTHER INFORMATION: streptavidin-binding peptide
<220> FEATURE:
<221> NAME/KEY: MISC_FEATURE
<222> LOCATION: (4)..(4)
<223> OTHER INFORMATION: X can be 0-50 amino acids of any type

<400> SEQUENCE: 22

His Pro Gln Xaa His Pro Gln
1               5

<210> SEQ ID NO 23
<211> LENGTH: 9
<212> TYPE: PRT
<213> ORGANISM: Artificial Sequence
<220> FEATURE:
<223> OTHER INFORMATION: streptavidin-binding peptide
<220> FEATURE:
<221> NAME/KEY: MISC_FEATURE
<222> LOCATION: (5)..(5)
<223> OTHER INFORMATION: X can be 0-50 amino acids of any type

<400> SEQUENCE: 23

His Pro Gln Phe Xaa His Pro Gln Phe
1               5

<210> SEQ ID NO 24
<211> LENGTH: 17
<212> TYPE: PRT
<213> ORGANISM: Artificial Sequence
<220> FEATURE:
<223> OTHER INFORMATION: streptavidin-binding peptide
<220> FEATURE:
<221> NAME/KEY: MISC_FEATURE
<222> LOCATION: (1)..(1)
<223> OTHER INFORMATION: X is Trp, Lys or Arg
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (7)..(7)

```
<223> OTHER INFORMATION: X is Gly or Glu
<220> FEATURE:
<221> NAME/KEY: MISC_FEATURE
<222> LOCATION: (8)..(8)
<223> OTHER INFORMATION: X is Gly, Lys or Arg
<220> FEATURE:
<221> NAME/KEY: MISC_FEATURE
<222> LOCATION: (9)..(9)
<223> OTHER INFORMATION: X can be 0-50 amino acids of any type
<220> FEATURE:
<221> NAME/KEY: MISC_FEATURE
<222> LOCATION: (10)..(10)
<223> OTHER INFORMATION: X is Trp, Lys or Arg
<220> FEATURE:
<221> NAME/KEY: MISC_FEATURE
<222> LOCATION: (11)..(11)
<223> OTHER INFORMATION: X is any amino acid
<220> FEATURE:
<221> NAME/KEY: MISC_FEATURE
<222> LOCATION: (16)..(16)
<223> OTHER INFORMATION: X is Gly or Glu
<220> FEATURE:
<221> NAME/KEY: MISC_FEATURE
<222> LOCATION: (17)..(17)
<223> OTHER INFORMATION: X is Gly, Lys or Arg

<400> SEQUENCE: 24

Xaa Xaa His Pro Gln Phe Xaa Xaa Xaa Xaa Xaa His Pro Gln Phe Xaa
1               5                   10                  15

Xaa

<210> SEQ ID NO 25
<211> LENGTH: 17
<212> TYPE: PRT
<213> ORGANISM: Artificial Sequence
<220> FEATURE:
<223> OTHER INFORMATION: streptavidin-binding peptide
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (7)..(7)
<223> OTHER INFORMATION: X is Gly or Glu
<220> FEATURE:
<221> NAME/KEY: MISC_FEATURE
<222> LOCATION: (8)..(8)
<223> OTHER INFORMATION: X is Gly, Lys, or Arg
<220> FEATURE:
<221> NAME/KEY: MISC_FEATURE
<222> LOCATION: (9)..(9)
<223> OTHER INFORMATION: X can be 0-50 amino acids of any type
<220> FEATURE:
<221> NAME/KEY: MISC_FEATURE
<222> LOCATION: (11)..(11)
<223> OTHER INFORMATION: X is any amino acid
<220> FEATURE:
<221> NAME/KEY: MISC_FEATURE
<222> LOCATION: (16)..(16)
<223> OTHER INFORMATION: X is Gly or Glu
<220> FEATURE:
<221> NAME/KEY: MISC_FEATURE
<222> LOCATION: (17)..(17)
<223> OTHER INFORMATION: X is Gly, Lys, or Arg

<400> SEQUENCE: 25

Trp Xaa His Pro Gln Phe Xaa Xaa Xaa Trp Xaa His Pro Gln Phe Xaa
1               5                   10                  15

Xaa

<210> SEQ ID NO 26
<211> LENGTH: 17
```

```
<212> TYPE: PRT
<213> ORGANISM: Artificial Sequence
<220> FEATURE:
<223> OTHER INFORMATION: streptavidin-binding peptide
<220> FEATURE:
<221> NAME/KEY: MISC_FEATURE
<222> LOCATION: (9)..(9)
<223> OTHER INFORMATION: X can be 0-50 amino acids of any type

<400> SEQUENCE: 26

Trp Ser His Pro Gln Phe Glu Lys Xaa Trp Ser His Pro Gln Phe Glu
1               5                   10                  15

Lys
```

METHODS OF ISOLATING A BIOLOGICAL ENTITY

CROSS-REFERENCE TO RELATED APPLICATIONS

This application is a U.S. National Stage application of PCT/EP2021/052331 filed 1 Feb. 2021, which claims priority to European Application No. 20154816.1 filed 1 Jan. 2020, the entire disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on 23 May 2023, is named SL_0369_0004_PCT_US.txt and is 9 Kilobytes in size.

FIELD OF THE INVENTION

The present invention relates to the field of cell separation or isolation, and specifically to affinity-based methods of isolating a biological entity from a sample via binding of an affinity tag to a molecule on the surface of the biological entity. The invention also relates to a dextran polymer, a kit for use in the methods of the invention and an apparatus for performing the methods of the invention.

BACKGROUND OF THE INVENTION

The isolation of defined pure cell populations expressing specific antigens on their surface is becoming more and more important as their significance is growing in clinical applications like diagnostics, biotechnological and biomedical applications. One example is the field of tissue engineering requiring the isolation of specific stem cells from tissues or organs. Another example is chimeric antigen receptor (CAR) T cell therapy as a novel cancer immunotherapy approach wherein patient-derived T cells are genetically engineered to produce an artificial T cell receptor enabling the CAR T cell to destroy cancer cells. A crucial step in the production of CAR T cells is the isolation of specific and pure T cell populations from patient material. Current cell separation techniques are reviewed in Kumar et al., (2007). Cell Separation: Fundamentals, Analytical and Preparative Methods, Springer-Verlag Berlin Heidelberg.

Specific cells can be isolated due to cell surface molecules via affinity-based methods. Techniques commonly used are flow cytometry such as fluorescence-activated cell sorting (FACS), magnetic bead separation technologies such as magnetic-activated cell sorting (MACS®), or affinity chromatography such as traceless affinity cell selection (TACS®). TACS® is a positive selection technology using immune affinity chromatography based on CD-specific low affinity Fab-fragments for the reversible capture and release of target cells. The positive selection by MACS® is based on magnetic beads coated with specific high affinity monoclonal antibodies to catch the target cells. The target cells separated by TACS® are "label-free" while cells positively isolated by MACS® will carry the cell specific label. A comparative study of these two separation methods was performed for monocyte isolation (Weiss et al., Cytometry Part A (2018), 95).

Mohr et al., Sci. Rep. 8 (2018), 16731 describe a classical immunoaffinity chromatographic method for isolating lymphocytes from whole blood. The method relies on low-affinity Fab-fragments attached to a column-matrix combined with the reversible Strep-tag technology. Further chromatographic techniques relying on the Strep-tag technology for purifying target cells from a sample are described, e.g., in the international applications WO 2013/124474 A2 and WO 2015/166049 A1. In particular, WO 2013/124474 A2 teaches that Strep-Tactin® coated agarose beads can be used to isolate cells which are bound by a Strep-tagged Fab fragment. WO 2015/166049 A1 teaches a further development of the method disclosed in WO 2013/124474 A2, wherein Strep-Tactin® is not directly linked to the beads but fused to or bound by a ligand or ligand binding partner which mediates the binding to the beads.

However, these current techniques suffer from multiple limitations concerning the yield, purity viability, and functionality of the isolated cells, the recovery of rare cells and the throughput. Accordingly, there is still a need for new and improved methods for isolating biological entities such as target cells or other membrane-enclosed vesicles.

This problem is solved by the present invention in accordance with the embodiments characterized in the claims and described further below.

SUMMARY OF THE INVENTION

Beads conventionally used for hitherto known cell separation methods constitute a mixture of beads of varying diameters between, for example, 30 to 180 µm with a majority of beads having a diameter of about 80 to 120 µm such as the agarose beads provided by IBA GmbH, Göttingen, Germany; see FIG. 1. Within the course of experiments performed in accordance with the present invention, it has surprisingly been found that lymphocytes to be isolated from blood preferentially bind to small agarose beads with diameters below 70 µm, whereas beads with a diameter above 70 µm up to 140 µm bind few cells and beads with diameters larger than 140 µm bind substantially no cells. However, as shown in FIG. 2 blood lymphocytes cannot be isolated via chromatographic methods using small agarose beads since the cells block the flow through the chromatographic matrix after binding the beads via filling up of the interstitial space between the beads. Accordingly, the majority of the beads used for conventional cell separation methods do not or do only marginally contribute to cell binding leading to inefficient cell isolation. In order to solve this problem, the inventors moved away from classical chromatography with linear flow and packed gel beds and established a new non-chromatographic method of cell separation using beads which are kept in continuous motion.

The new method has exemplarily been demonstrated by using Fab fragments immobilized on Strep-Tactin-coated agarose beads available from IBA GmbH (Göttingen Germany). The continuous motion of the beads can be achieved either by shaking manually or in a semi-automated form using an apparatus such as the FABian® device by Cell.Copedia GmbH; see Examples 3 and 5. In Example 3, $CD3^+$ cells have been isolated from peripheral blood mononuclear cells (PBMCs) via agarose beads coated with anti-CD3 Fab in a reaction tube, wherein the beads have been kept in motion on a laboratory roller resulting in 98% pure $CD3^+$ cells in high yield; see FIGS. 4A and B. In Example 5, $CD81^+$ cells have been isolated from buffy coat via anti-CD81 Fab coated small agarose beads having a diameter of 40-60 µm and large agarose beads having a diameter of >140 µm in a semiautomated manner, wherein the beads have been kept in motion by an apparatus performing pipetting processes. The method performed in Example 5 resulted in high yield of CD81' cells when small beads were used; see FIG. 6A.

Accordingly, in a first aspect, the present invention generally relates to an affinity-based non-chromatographic method for the isolation of a biological entity and in particular to:

[1] A method of isolating a biological entity from a sample comprising
  (i) providing a sample comprising the biological entity (1), wherein the biological entity comprises a surface antigen (2);
  (ii) providing a tagging agent (3) comprising at least one binding domain (4) capable of specifically binding to the surface antigen (2) on the biological entity;
  (iii) providing freely movable beads (6); and
  (iv) incubating the sample, tagging agent (3) and beads (6) within a container and allowing complex formation between the biological entity (1), the tagging agent (3) and the beads (6) while the beads float within the sample, wherein the binding of the biological entity (1) via the tagging agent (3) to the beads (6) is directly or indirectly mediated by non-covalent protein-ligand interaction comprising a ligand binding partner (7) and a ligand (5); and
  (v) purifying the biological entity (1) by comprising temporarily holding the beads (6) in place in the container, while discarding the supernatant, and adding a washing buffer; and/or
  (vi) isolating the biological entity (1) by releasing the biological entity (1) from the beads (6) and the tagging agent (3), respectively, and recovery of the biological entity (1) from the supernatant while temporarily holding the beads (6) in place in the container, optionally allowing for the recovery of the tagging agent (3) and/or beads (6).

[2] The method of [1], wherein
  (a) the binding domain (4) is present in an antigen-binding fragment (Fab);
  (b) the ligand binding partner (7) comprises streptavidin or a functionally analog or derivative thereof and the ligand (5) comprises a streptavidin binding peptide; and/or
  (c) the beads (6) are non-magnetic beads, preferably agarose beads.

[3] The method of [1] or [2], wherein the ligand binding partner (7) is Strep-Tactin® and the ligand (5) is a Strep®-Tag.

[4] The method of any one of [1] to [3], wherein the beads (6) are characterized to have a diameter of about 30-100 µm, preferably about 40-60 µm.

[5] The method of any one of [1] to [4], wherein the sample and optionally any other liquid is introduced into and discharged from the container through the same opening and/or the beads (6) are hold in place by a frit or sieve.

[6] The method of any one of [1] to [5], wherein the tagging agent (3) comprises an antigen-binding fragment (Fab) (4) which is linked to the ligand (5) and wherein the beads (6) comprise the ligand binding partner (7) which immobilizes the tagging agent on the beads (6).

[7] The method of any one of [1] to [5], wherein the tagging agent (3) comprises an antigen-binding fragment (Fab) (4) which is linked to the ligand (5) and wherein the beads (6) comprise a further ligand (12a), wherein the further ligand (12a) and the ligand binding partner (7) form a further protein-ligand interaction, preferably wherein the further ligand (12a) is biotin.

[8] The method of any one of [1] to [5], wherein the tagging agent (3) comprises an antigen-binding fragment (Fab) (4) which is linked to the ligand (5) and wherein the beads (6) comprise a further ligand (12) and wherein the ligand binding partner (7) comprises a further ligand binding partner (13), wherein the ligand (12) and the ligand binding partner (13) form a further protein-ligand interaction.

[9] The method of [7], wherein the tagging agent is immobilized on a carrier (11) by non-covalent protein-ligand interaction, preferably wherein the non-covalent protein interaction is mediated between the ligand (5) of the tagging agent (3) and the ligand binding partner (7) on the carrier (11).

[10] The method of [7] or [9], wherein the carrier is a dextran polymer having an average molecular weight of about 500 kDa to 3,000 kDa, preferably about 1,500 kDa to 2,500 kDa and comprises at least two molecules of the ligand binding partner (7), which is preferably covalently bound streptavidin or an analog or derivative thereof, which is capable of binding the tagging agent (3) comprising the ligand (5) and the further ligand (12a) on the beads (6), preferably wherein the biological entity (1) to be isolated (1) is an exosome.

[11] The method of any one of [1] to [5], wherein the tagging agent (3) is immobilized on the beads (6) via a linking molecule (10) which comprises an antigen (2') recognized by the tagging agent (3) and a component for said non-covalent protein-ligand interaction, preferably wherein the component is the ligand (5) and wherein the beads (6) comprise the ligand binding partner (7).

[12] The method of [11], wherein the tagging agent (3) is a tagging agent (3') comprising at least two binding domains (4), which are linked to each other.

[13] The method of [11], wherein the method comprises at least two tagging agents (3) capable of recognizing the surface antigen (2) and the recombinant antigen (2') comprised in the linking molecule, wherein the tagging agents (3) are immobilized on a carrier (11) by non-covalent protein-ligand interaction, preferably wherein the non-covalent protein interaction is mediated between the ligand (5) of the tagging agent (3) and the ligand binding partner (7) on the carrier (11)

[14] The method of [13], wherein the tagging agents (3) are immobilized on the carrier (11) and wherein the linking molecule (10) is immobilized to the beads (6) prior to step (iv) as characterized in [1].

[15] The method of [13] or [14], wherein the carrier is a dextran polymer having an average molecular weight of about 500 kDa to 3,000 kDa, preferably about 1,500 kDa to 2,500 kDa and comprises at least two molecules of the ligand binding partner (7), which is preferably covalently bound streptavidin or an analog or derivative thereof, which is capable of binding the tagging agent (3) comprising the ligand (5).

[16] The method of any one of [1] to [15], wherein in step (vi) as characterized in [1] the biological entity (1) is released by adding a competing ligand, optionally which inter alia leads to the release of the tagging agent (3, 3') from the antigen (2, 2') and/or the ligand binding partner (7) and/or the further ligand (12) from the further ligand binding partner (13), and/or the further ligand (12a) from the ligand binding partner (7).

[17] The method of any one of [1] to [16], wherein the sample is a body fluid, preferably blood or umbilical cord blood and/or the biological entity is a cell, nucleus or a membrane-vesicle, preferably a cell-derived membrane vesicle, more preferably an exosome.

[18] The method of any one of [1] to [17], wherein the container is a tube, vial, syringe. ampule, or column.

In further aspects, the present invention relates to chromatographic methods of isolating a biological entity. These methods apply a chromatographic approach but have been optimized in order to archive high yields and purity of the biological entities to be isolated. In particular, as described in Example 6, a dextran molecule has been used as a carrier for the ligand binding partner such as Strep-Tactin® resulting in polymerization/multimerization of the ligand binding partner. Due to the resulting large flexible structure an avidity effect is achieved since more bonds form between the antigens on the cell surface and the carrier and more bonds form between the carrier and the antigens immobilized on the stationary phase compared to the use of a tagging agent only. Thereby, the method results in highly efficient isolation of $CD4^+$ cell; see FIG. 8. Alternatively, instead of the carrier a bivalent tagging agent may been used. Thus, the present invention also relates to:

[19] A method of isolating a biological entity from a sample comprising
- (i) providing a sample comprising the biological entity (1), wherein the biological entity (1) comprises a surface antigen (2);
- (ii) providing a linking molecule (10) comprising an antigen (2') and a component for a non-covalent protein-ligand interaction, preferably wherein the component is a ligand (5);
- (iii) providing at least two tagging agents (3) each comprising at least one binding domain (4) capable of specifically binding to the antigen (2) on the biological entity or to the antigen (2') comprised in the linking molecule (10), preferably wherein the tagging agents further comprise a component for a non-covalent protein-ligand interaction, preferably wherein the component is a ligand (5);
- (iv) providing a carrier (11) comprising at least two components for non-covalent protein-ligand interactions, preferably wherein the components are ligand binding partners (7);
- (vi) providing a stationary phase comprising a component capable of forming a protein-ligand interaction, preferably wherein the component is a ligand binding partner (7); and
- (vii) incubating the sample, linking molecule (10), tagging agents (3), carrier (11) and stationary phase within a container and allowing complex formation between the biological entity (1), the tagging agents (3), the linking molecule (10), the carrier (11) and the beads (6), wherein the binding of the biological entity (1) via the tagging agent (3) to the carrier (11) and the binding of the linking molecule (10) via the tagging agent (3) to the carrier (11) and the binding of the linking molecule (10) to the stationary phase are mediated by non-covalent protein-ligand interaction, wherein the biological entity (1) is immobilized on the stationary phase; and
- (viii) purifying the biological entity (1) by a chromatographic procedure; and/or (ix) isolating the biological entity (1) by releasing the biological entity (1) from the carrier (11) and the tagging agent (3), respectively.

[20] The method of [19], wherein
- (a) the tagging agent (3) comprise an antigen-binding fragment (Fab) (4) which is linked to the ligand (5); and/or
- (b) the ligand binding partner(s) (7) comprise(s) streptavidin or a functionally analog or derivative thereof, and the ligand (5) comprises a streptavidin binding peptide.

[21] The method of [19] or [20], wherein the ligand binding partner (7) is Strep-Tactin® and the ligand (5) is a Strep®-Tag.

[22] The method of any one of [19] to [21], wherein the tagging agents (3) are immobilized on the carrier (11) and wherein the linking molecule (10) is immobilized to the stationary phase prior to step (vii) as characterized in [19].

[23] The method of any one of [19] to [22], wherein the carrier is a dextran polymer having an average molecular weight of 3,000,000 Da.

[24] The method of any one of [19] to [23], wherein in step (ix) as characterized in [15] the biological entity (1) is released by adding a competing agent, optionally which inter alia leads to the release of the tagging agent (3) from the antigen (2, 2') and/or the ligand binding partner (7).

[25] The method of any one of [19] to [24], wherein the sample is a body fluid, preferably blood or umbilical cord blood and/or the biological entity is a cell, nucleus or a membrane-vesicle, preferably a cell-derived membrane vesicle, more preferably an exosome.

[26] The method of any one of [19] to [25], wherein the container is a tube, vial, syringe. ampule, or column.

[27] A method of isolating a biological entity from a sample comprising
- (i) providing a sample comprising the biological entity (1), wherein the biological entity (1) comprises a surface antigen (2);
- (ii) providing a linking molecule (10) comprising an antigen (2') and a component capable of forming a non-covalent protein-ligand interaction, preferably wherein the component is a ligand (5);
- (iii) providing a tagging agent (3') comprising two binding domains (4) which are linked to each other and capable of specifically binding to the antigen (2) on the biological entity and to the antigen (2') comprised in the linking molecule (10), preferably wherein the binding domains are antigen-binding fragments (Fabs);
- (vi) providing a stationary phase comprising a component capable of forming the protein-ligand interaction, preferably wherein the component is a ligand binding partner (7); and
- (vii) incubating the sample, linking molecule (10), tagging agent (3') and the stationary phase within a container and allowing complex formation between the biological entity (1), the tagging agent (3'), the linking molecule (10) and the stationary phase, wherein the binding of the biological entity (1) via the tagging agent (3') and the linking molecule (10) to the stationary phase is mediated by the non-covalent protein-ligand interaction, wherein the biological entity (1) is immobilized on the beads (6); and
- (viii) purifying the biological entity (1) by a chromatographic procedure; and/or
- (ix) isolating the biological entity (1) by releasing the biological entity (1) from the stationary phase and the tagging agent (3'), respectively.

[28] The method of [27], wherein the ligand binding partner (7) comprises streptavidin or a functionally analog or derivative thereof and the ligand (5) comprises a streptavidin binding peptide.

[29] The method of [27] or [28], wherein the ligand binding partner (7) is Strep-Tactin® and the ligand (5) is a Strep®-Tag.

[30] The method of any one of [27] or [29], wherein in step (ix) as characterized in [27] the biological entity (1) is released by adding a competing ligand, optionally which inter alia leads to the release of the tagging agent (3') from the antigen (2, 2') and/or the ligand binding partner (7).

[31] The method of any one of [27] to [30], wherein the sample is a body fluid, preferably blood or umbilical cord blood and/or the biological entity is a cell, nucleus or a membrane-vesicle, preferably a cell-derived membrane vesicle, more preferably an exosome.

[32] The method of any one of [27] to [31], wherein the container is a tube, vial, syringe. ampule, or column.

In a further aspect, the invention relates to kits suitable for performing the methods of the invention:

[33] A kit for use in the method of any one of [1] to [32], the kit comprising a tagging agent (3, 3'), beads (6), carrier (11), linking molecule (10), further ligand (12, 12a), ligand binding partner (13), washing buffer and/or competing agent.

In a further aspect, the invention relates to an apparatus suitable for performing the methods of the invention:

[34] An apparatus for performing the method of any one of [1] to [18], comprising holders for the container, receptacles for the supply and reception of liquids, a device for supplying and receiving liquids from the receptacle to the container, configured to enable floating beads (6) up and down within a liquid present in the container as well as means for soaking, pumping and draining a liquid through one opening of the container and discharging the liquid while the beads (6) are hold in place.

[35] An apparatus for performing the method of any one of [19] to [32], comprising holders for the container, receptacles for the supply and reception of liquids, a device for supplying and receiving liquids from the receptacle to the container, as well as means for soaking, pumping and draining a liquid through one opening of the container.

In another aspect, the invention relates to

[36] A dextran polymer having an average molecular weight of 3,000,000 Da, wherein the dextran polymer comprises at least two molecules of covalently bound streptavidin (7) or an analog or derivative thereof, which is capable of binding a tagging agent (3) comprising a ligand (5), wherein the ligand (5) is a streptavidin binding peptide, preferably a Strep-Tag.

[37] Use of the dextran polymer of [36] in the method of any one of [9] to [26] as the carrier (11).

As mentioned above, in preferred embodiments, the ligand binding partner (7) comprises streptavidin or a functionally analog or derivative thereof, preferably the ligand binding partner (7) is Strep-Tactin® and the ligand (5) comprises a streptavidin binding peptide, preferably the ligand (5) is a Strep®-Tag and in embodiments encompassing the further ligand (12a), this further ligand (12a) is preferably biotin or an analogue or derivative thereof. This encompasses all available Strep-Tactin® systems including for example the Strep-Tactin®XT system or the Strep-Tactin®XTS system (IBA GmbH, Göttingen, Germany). Those are described in detail in the international applications WO 02/077018 A1, WO 2014/076277 A1 and WO 2017/186669 A1 all of which are herein expressly incorporated by reference. These systems are based on muteins of streptavidin that reversibly bind to biotin or the analog or derivative thereof and the corresponding binding peptides, respectively, as explained further below.

DETAILED DESCRIPTION OF THE INVENTION

Figure 2:
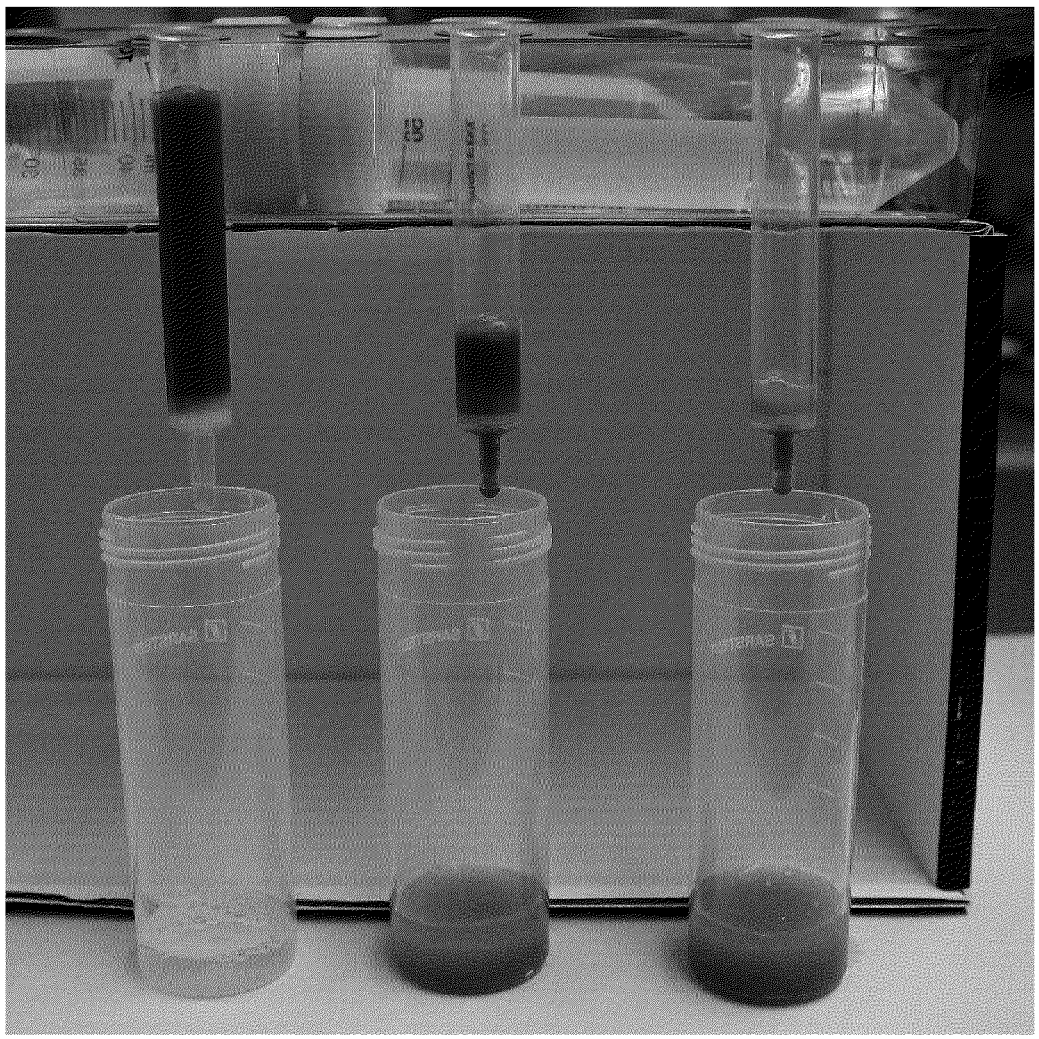
FIG. 2: Photography of column-based chromatography using agarose bead fractions with varying diameters: 40-60 µm (left column), 80-120 µm (middle column), and >140 µm (right column). Small size beads (left column) do not allow for flow through the chromatography column since the binding cells block the flow through the column. Standard size beads (middle column) allow chromatography with retarded speed, whereas the large size beads (right column) allow rapid passage of the sample without delay.
Figure 3:
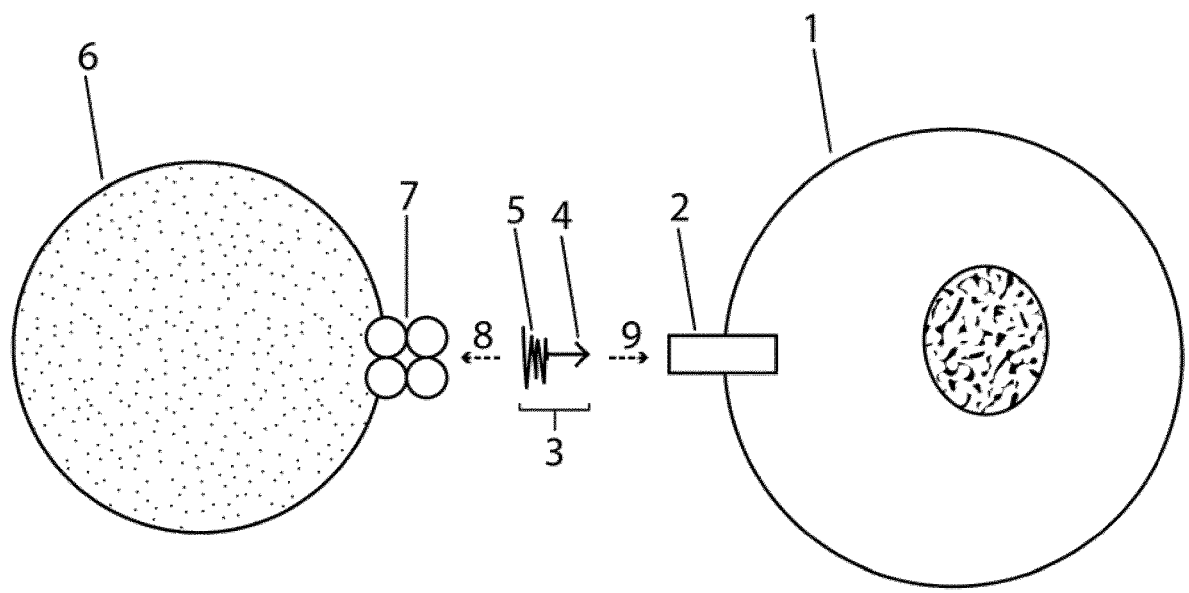
FIG. 3: Schematic representation of a method of isolating a biological entity, wherein an antigen (2) present on the surface of the biological entity (1) is recognized by a binding domain (4) of a tagging agent (3). The tagging agent further comprises a ligand (5), wherein the ligand (5) is involved in a non-covalent protein-ligand interaction (8) with a ligand binding partner (7) on the surface of a bead (6), thereby immobilizing the biological entity (1) on the beads (6) allowing for its isolation from a sample. The principle depicted has been applied in Examples 3-5.

Within the course of experiments performed in accordance with the present invention, it has been found that for cell separation, the beads and, in particular, their packaging are of great importance for the outcome of the cell isolation process. For example, it turned out surprisingly that non-chromatographic methods, wherein freely movable beads are used, are beneficial over conventional chromatographic methods, wherein the beads constitute a stationary phase. This is because in the novel non-chromatographic methods of the present invention, smaller beads can be used which in conventional chromatographic cell separation methods results in clogging of the stationary phase and column, respectively; see FIG. 2. Accordingly, in a first aspect, the present invention generally relates to a non-chromatographic affinity-based method for isolating a biological entity from a sample. Thereby, the biological entity carries a surface antigen which enables the specific isolation of the target entity from components present in the sample that do not contain the antigen. The general principle and components involved in one of the methods underlying the present invention is depicted in FIG. 3.

In particular, in the first aspect, the invention relates to a method of isolating a biological entity from a sample comprising providing a sample comprising the biological entity (1), a tagging agent (3) comprising at least one binding domain (4) capable of specifically binding to a surface antigen (2) on the surface of the biological entity, freely movable beads (6). These components, i.e. the sample, tagging agent (3) and beads (6) are incubated within a container which allows for complex formation between the biological entity (1), the tagging agent (3) and the beads (6) while the beads float within the sample. Thereby, the binding of the biological entity (1) via the tagging agent (3) to the beads (6) is directly or indirectly mediated by non-covalent protein-ligand interaction comprising a ligand binding partner (7) and a ligand (5). The biological entity (1) is then purified by temporarily holding the beads (6) in place in the container, while discarding the supernatant, and adding a washing buffer and may be isolated by release from the beads (6) and the tagging agent (3), respectively. The biological entity (1) is then recovered from the supernatant while temporarily holding the beads (6) in place in the container. Optionally the tagging agent (3) and/or beads (6) may be recovered from the solution.

"Isolating" or "isolation" as used herein means that the biological entity is enriched in a sample that is obtained as a result of a method of the invention compared to the content (concentration) of the sample prior to the isolation of the biological entity. This means the target biological entity might be enriched in a sample, for example, from about a content of about 0.1% of the entire amount of biological entities in a sample to about 10% or more, or 20% or more, 30% or more, 40% or more, in a sample collected after running a method of the invention. "Isolated" also means that the sample, e.g., eluate or fraction obtained contains the biological entity as essentially only kind of, e.g., a cell (cell population), for example, the isolated biological entities represents more than 75%, or more than 80%, or more than 85%, or more than 90%, or more than 95% or more than 97% or more than 99% of the biological entities present in a sample after the isolation procedure. In general, as used herein, the term "about" refers to a value that is ±10% of the recited value.

Before the single components of the invention are explained in detail, the method of the invention in general is outlined in the following and explained by means of an illustrative example: The principle underlying the present invention is schematically depicted in FIG. 3. The method involves complex formation between beads (6) with a tagging agent (3) via a non-covalent protein-ligand interaction (8) and a biological entity (1) which is recognized by the tagging agent (3) via a surface antigen (2) present on the surface of the biological entity (1). As illustratively shown in Example 3, $CD3^+$ cells can efficiently be isolated from human peripheral blood mononuclear cells (PBMCs) via the CD3 receptor which is recognized and bound by a Strep-tagged anti-human CD3 Fab fragment as the tagging agent (3). The tagging agent in turn via it's Strep-tag binds Strep-Tactin® coated agarose beads via a non-covalent protein-ligand interaction. Such complex formation for the isolation of target cells have been described before, e.g. in WO 2013/124474 A2. However, the methods described therein are based on chromatographic methods involving a stationary phase which confers the disadvantages as outlined above. In contrast, in the method of the present invention an approach is applied, wherein the beads float within the sample during the incubation.

As outlined, supra, for the isolation of biological entities from a sample in accordance with the method of the present invention, the sample comprising the biological entity (1) to be isolated, tagging agent (3) and beads (6) are incubated within a container allowing for complex formation between the biological entity (1), the tagging agent (3) and the beads (6) which is mediated via a non-covalent protein-ligand interaction, as described above, which comprises a ligand (5) and a ligand binding partner (7). As schematically depicted in FIG. 3 and illustratively shown in Example 3, for the case where the non-covalent protein ligand interaction (8) is mediated by a streptavidin-biotin-like interaction, the complex forms via the tagging agent (3), i.e. Strep-tagged anti-human CD3 Fab fragment which binds to Strep-Tactin® coated agarose beads (ligand binding partner (7) on beads (6)) via its Step-tag® (ligand (5)), wherein the tagging agent (3) via the Fab fragment (binding domain (4)) recognizes the CD3 receptor (surface antigen (2)) on the $CD3^+$ cell (biological entity (1)) via an antigen recognition interaction (9). The order of the addition of the components to the container for the incubation is thereby not determined. For example, as indicated in Example 3, beads (6) can be used that are pre-coated with the ligand binding partner (7) such as the commercially available Strep-Tactin® coated agarose beads (IBA GmbH, Göttingen, Germany) on which the tagging agent (3) is immobilized via the ligand (5) prior to the addition of the sample comprising the biological entity (1) to be isolated.

Once all components have been added to the container, the suspension, in particular the beads, are kept in continuous motion during the incubation. The person skilled in the art is aware of numerous ways of keeping a solution in motion. For example, the container can be manually gently shaken or a device can be used for keeping the solution within the container in motion. Various different devices performing different motion patterns are available, such as orbital or reciprocating shakers, rollers, rockers, rotators, tube revolvers and mixers. For example, as shown in Example 3, a rocking shaker at low speed is suitable for keeping the beads in motion. In general, according to the present invention, the continuous motion avoids settling of the beads so that the components for the method of the invention and the sample containing the biological entity are continuously mixed with the beads and the complexes as defined herein can form. Of course, the person skilled in the art is aware that the solution is not vigorously shaken so that complex formation is disrupted. Rather in accordance with the invention, during the incubation step the beads continuously float in the suspension.

In accordance with the present invention, the container can be any suitable vessel with a suitable volume that can hold a liquid. In one embodiment of the invention, the container is a tube, vial, syringe, ampule, or column. Preferably, the container is configured in the method of the invention such that it does not allow for flow through of the sample. In one embodiment of the invention, the sample and optionally any other liquid is introduced into and discharged from the container through the same opening. For example, as shown in Example 3, the container can be a tube to which the sample and components for performing the method of isolating a biological entity from the sample are added through the opening. The tube is closed with a lid and the tube is gently moved in order to allow for floating of the beads within the tube. Following the incubation, the tube is kept without movement in order to allow for settling of the beads so that the sample or any other liquid can be removed, i.e. the supernatant is discarded, e.g., by decantation or pipetting. In case the supernatant is discarded by pipetting, a pipette tip can be used which is modified in such a way to prevent that unsettled beads enter the tip and/or are discarded. As indicated in Example 3, this can be achieved when a nylon sieve or any other sieve with a suitable pore size has been glued to the top of the tip to keep remaining unsettled beads away. If necessary, the tip of the pipette tip is removed or a wide bore tip is used and the sieve glued to the edges of the tip. The sieve at the tip of the pipette tip prevents that unsettled beads enter the pipette tip, thereby avoiding loss of beads and biological entities of interest immobilized thereon, respectively. In this context, as used herein the term "immobilized" when referring to a component of the method of the present invention being immobilized on beads or other components does not mean that the beads as such are immobilized but only relates to the component being immobilized in relation to the beads, i.e. being attached, bound, linked or the like thereto. At the same time the beads in accordance with the present invention remain able to continuously float within the sample. Only when the liquid surrounding the beads is to be removed the beads are temporarily allowed to settle or to be kept in place. In one embodiment the beads are kept in place by a frit or sieve. The person skilled in the art will readily appreciate that the pore size of the frit or sieve keeping the beads in place is to be selected to exclude the beads from passing through while all other components, biological entities that are not immobilized on the beads are allowed to flow through.

As described in detail elsewhere herein and shown in Examples 5, 7 and 8, according to the present invention, an apparatus, such as the FABian® device can be used in accordance with the method of the present invention which keeps the beads in continuous motion. In these examples, the container comprises a syringe body and a syringe body attachment and the sample is filled into the syringe body attachment from the bottom via soaking up by the syringe body. The sample is released from the syringe body attachment through the same opening by pressure from the syringe body. Accordingly, the syringe body enables the syringe body attachment to be filled and emptied via a pipetting process from the syringe body. A membrane attached to the bottom of the syringe body attachment prevents the beads which have been prefilled into the container and components in complex therewith from leaving the container. As described, infra, the FABian® device is operated in the "moving batch mode", a novel program proving for continuous motion of the beads. The detailed program is indicated in FIGS. 6B and C. Similarly, peristaltic pumps can be used which can be run in forward and reverse modus and thus, keep the beads "moving" as performed in the FABian® device.

The time of the incubation of the components allowing for complex formation is not particularly limited, e.g., as shown in Example 3, an incubation time of 5 minutes is sufficient for efficient isolation of biological entities such as $CD3^+$ cells. However, longer and shorter incubation periods are likewise encompassed by the present invention. Regarding the use of the FABian® device or the peristaltic pump for performing the method of the present invention, the incubation times largely depend on the amount of the sample from which biological entities are to be isolated. For example, when the flow is set to about 1-2 ml/min/cm$^2$ the resulting incubation times are between 10 to 60 min.

The incubation step and the method of the invention, in general except for where stated otherwise, can be performed in any fluid suitable for preserving the biological activity of the biological entity. Typically, the fluid is a liquid. In some embodiments, the respective liquid is or includes water, for example, in the form of an aqueous solution. Further components may be included in a respective aqueous solution, for example, dissolved or suspended therein. As an illustrative example, an aqueous solution may include one or more buffer compounds. Numerous buffer compounds are used in the art and may be used to carry out the various processes described herein. Examples of buffers include, but are not limited to, solutions of salts of phosphate such as phosphate buffered saline (PBS), carbonate, succinate, carbonate, citrate, acetate, formate, barbiturate, oxalate, lactate, phthalate, maleate, cacodylate, borate, N-(2-acetamido)-2-amino-ethanesulfonate (also called (ACES), N-(2-hydroxyethyl)-piperazine-N'-2-ethanesulfonic acid (also called HEPES), 4-(2-hydroxyethyl)-1-piperazine-propanesulfonic acid (also called HEPPS), piperazine-1,4-bis(2-ethanesulfonic acid) (also called PIPES), (2-[Tris(hydroxymethyl)-methyl-amino]-1-ethansulfonic acid (also called TES), 2-cyclohexy-lamino-ethanesulfonic acid (also called CHES) and N-(2-acetamido)-iminodiacetate (also called ADA). Any counter ion may be used in these salts; ammonium, sodium, and potassium may serve as illustrative examples. Further examples of buffers include, but are not limited to, tri-ethanolamine, diethanolamine, zwitterionic buffers such as betaine, ethylamine, triethylamine, glycine, glycylglycine, histidine, tris-(hydroxymethyl)aminomethane (also called TRIS), bis-(2-hydroxyethyl)-imino-tris(hydroxymethyl)-methane (also called BIS-TRIS), and N-[Tris(hydroxym-ethyl)-methyl]-glycine (also called TRICINE), to name only a few. The buffer may further include components that stabilize the biological entity to be isolated, for example proteins such as (serum) albumin, growth factors, trace elements and the like. The choice of the suitable buffer is within the knowledge of the person of average skill in the art and can be carried out empirically.

In addition, a method according to the present invention may be carried out at any temperature at which the viability of the biological entity is at least essentially uncompromised. When reference is made herein to conditions that are at least essentially not harmful, not detrimental or at least essentially not compromising viability, conditions are referred to, under which the percentage of biological entities that can be recovered with full viability, is at least 70%, including at least 75%, at least 80%, at least 85%, at least 90%, at least 92%, at least 95%, at least 97%, at least 98%, at least 99% or at least 99.5%. In some embodiments a method according to the invention is carried out at a temperature of about 20° C. or below, such as about 14° C. or below, about 9° C. or below or about 6° C. or below. Depending on the biological entity to be isolated a suitable temperature range may for instance be from about 2° C. to about 45° C., including from about 2° C. to about 40° C., from about 3° C. to about 35° C., or from about 4° C. to about 30° C. if an aqueous medium is used to encompass the biological entity. In some embodiments a method according to the invention is carried out at a constant temperature value, or at a selected temperature value ±about 5° C., ±about 4° C., ±about 3° C., ±about 2° C., ±about 1° C. or ±about 0.5° C. The temperature may, for example, be selected to have a value of about 5° C., about 10° C., about 15° C., about 20° C. or about 25° C. In some embodiments, the temperature is altered, i.e. increased, decreased or varied by combinations thereof, during a method according to the present invention. The temperature may for example be altered within a range as defined above, e.g. in the range from about 2° C. to about 40° C. or within the range from about 3° C. to about 35° C. The person skilled in the art is able to empirically determine a suitable temperature, taking into account the nature of the biological entities and the isolation conditions. For example, temperature insensitive cells such as cancer cells might be isolated at room temperature or even elevated temperature such as 37° C.

Following the incubation step during which the complex formation takes place, the biological entity immobilized on the beads is purified from other components and non-target biological entities present in the starting material, i.e. in the sample comprising the biological entity of interest. This purification step is achieved by temporarily holding the beads in place in the container, while discarding the supernatant comprising non-bound biological entities and adding a washing buffer. The addition of the washing buffer to the container or subsequent gentle shaking of the container provides that the beads again float within the container. The washing step usually is repeated several times to enhance purity of the biological entity. Subsequently or alternatively to the purification step(s), the biological entity is isolated by releasing the biological entity from the beads and the tagging agent, respectively, and recovered from the suspension while holding the beads temporarily in place and collecting the supernatant. Optionally, the beads and/or tagging agent can also be recovered to be used again.

Biological Entity

The term "biological entity" (marked with the reference sign (1) in the Figures) is to be understood to encompass cells and all other vesicles such as cell organelles, viruses, exosomes, liposomes, synaptic vesicles and the like, i.e. the target is any biological entity in which a membrane (which can also be a lipid bilayer) separates the interior from the outside environment (ambience) and which comprise one or more kinds of specific surface antigens. A biological entity or a population of biological entities is isolated from a sample that, for example, may include a variety of different cells or cell populations. Virtually any biological entity that has at least one common surface antigen, i.e. antigen on its surface can be separated from other components contained in a sample. In order to achieve an avidity effect, as discussed below, the surface antigen is typically present in two or more copies on the surface of the biological entity.

In one embodiment of the invention, the biological entity is a prokaryotic cell, such as a bacterial cell or archaeon. Alternatively, in one embodiment, the biological entity is a virus, an organelle, such as a mitochondrion, a chloroplast, a Golgi apparatus or a nucleus or an extracellular vesicle such as a microsome, an exosome, or a lysosome, or a synaptic vesicle. In particular, as shown in Example 8, exosomes can efficiently be isolated from a sample, such as a blood sample by applying one of the methods of the present invention. Therefore, in one embodiment of the present invention, the biological entity is an extracellular vesicle, such as an exosome. Furthermore, it is prudent to expect that the method of the present invention is likewise highly suitable for the isolation of cell nuclei. Therefore, in a further embodiment of the present invention, the biological entity is a cell nucleus.

In some embodiments, the biological entity is a eukaryotic cell, such as a plant cell, a fungal cell, a yeast cell, a protozoon or an animal cell. In some embodiments the biological entity is a mammalian cell, including a cell of a rodent species, or an amphibian cell, e.g. of the subclass Lissamphibia that includes, e.g., frogs, toads, salamanders or newts. Examples of a mammalian cell include, but are not limited to a blood cell, a semen cell or a tissue cell, e.g., a hepatocyte or a stem cell, e.g., CD34-positive peripheral stem cells or Nanog or Oct-4 expressing stem cells derived from a suitable source, a hematopoietic stem cell from bone marrow or cord blood. A blood cell is, for instance, a leukocyte or an erythrocyte. A leukocyte is, for example, a neutrophil, an eosinophil, a basophil, a monocyte, a lymphocyte, a macrophage or a dendritic cell. A respective lymphocyte is, for example, a T cell, including a CMV-specific $CD8^+$ T-lymphocyte, a cytotoxic T-cell a, memory T-cell (an illustrative example of memory T-cells are $CD62L^+CD8^+$ specific central memory T-cells) or a regulatory T-cell (an illustrative example of Treg are $CD4^+CD25^+$ $CD45RA^+$ Treg cells), a T-helper cell, for example, a $CD4^+$ T-helper cell, a B cell or a natural killer cell, to mention only a few illustrative examples.

Examples of mammals include, but are not limited to a rat, a mouse, a rabbit, a guinea pig, a squirrel, a hamster, a hedgehog, a cat, a platypus, an American pika, an armadillo, a dog, a lemur, a goat, a pig, an opossum, a horse, an elephant, a bat, a woodchuck, an orangutan, a rhesus monkey, a woolly monkey, a macaque, a chimpanzee, a tamarin (saguinus oedipus), a marmoset and a human. The cell may, for instance, be a cell of a tissue, such as an organ or a portion thereof. Examples of a respective organ include, without being limited thereto, adrenal tissue, bone, blood, bladder, brain, cartilage, colon, eye, heart, kidney, liver, lung, muscle, nerve, ovary, pancreas, prostate, skin, small intestine, spleen, stomach, testicular, thymus, tumor, vascular or uterus tissue, or connective tissue. In some embodiments, the cell is a stem cell.

A sample from which the biological entity is to be isolated may be of any origin. It may for instance, but not limited to, be derived from humans, animals, plants, bacteria, fungi, or protozoae. Accordingly, any of the following samples selected from, but not limited to, the group consisting of a soil sample, an air sample, an environmental sample, a cell culture sample, a bone marrow sample, a rainfall sample, a fallout sample, a sewage sample, a ground water sample, an abrasion sample, an archaeological sample, a food sample, a blood sample (including whole blood), a serum sample, a plasma sample, an urine sample, a stool sample, a semen sample, a lymphatic fluid sample, a cerebrospinal fluid sample, a nasopharyngeal wash sample, a sputum sample, a mouth swab sample, a throat swab sample, a nasal swab sample, a bronchoalveolar lavage sample, a bronchial secretion sample, a milk sample, an amniotic fluid sample, a biopsy sample, a cancer sample, a tumor sample, a tissue sample, a cell sample, a cell culture sample, a cell lysate sample, a virus culture sample, a nail sample, a hair sample, a skin sample, a forensic sample, an infection sample, a nosocomial infection sample, a space sample or any combination thereof. Where desired, a respective sample may have been preprocessed to any degree. As an illustrative example, a tissue sample may have been digested, homogenized or centrifuged prior to being used in a method according to the present invention. In another illustrative example, a sample of a body fluid such as blood might be obtained by standard isolation of blood cells. Furthermore, the sample may be an induced pluripotent stem cell (iPSC) from which, e.g., extracellular vesicles and/or exosomes can be isolated in accordance with the method of the present invention. If an isolation method described here is used in basic research, the sample might be cells of in vitro cell culture experiments. The sample will typically have been prepared in form of a fluid, such as a solution or dispersion.

Surface Antigen

A "surface antigen" or short "antigen" (marked with the reference sign (2) in the Figures) refers to any molecule on the surface of the biological entity as long as it remains covalently or non-covalently bonded on the surface during the isolation process according to the present invention. For the purpose of the isolation process in accordance with the present invention, the surface antigen is recognized and bound by a binding molecule such as the tagging agent described below. In some embodiments, the surface antigen is a peptide or protein. In some embodiments, the surface antigen is a lipid, a polysaccharide or a nucleic acid. A surface antigen that is a protein may be a peripheral membrane protein or an integral membrane protein. It may have in some embodiments one or more domains that span the membrane. As a few illustrative examples, a membrane protein with a transmembrane domain may be a receptor such as a G-protein-coupled receptor, such as an odorant receptors, a rhodopsin receptor, a rhodopsin pheromone receptor, a peptide hormone receptor, a taste receptor, a GABA receptor, an opiate receptor, a serotonin receptor, a $Ca^{2+}$ receptor, melanopsin, a neurotransmitter receptor, such as a ligand gated, a voltage gated or a mechanically gated receptor, including the acetylcholine, the nicotinic, the adrenergic, the norepinephrine, the catecholamines, the L-DOPA-, a dopamine and serotonin (biogenic amine, endorphin/enkephalin) neuropeptide receptor, a receptor kinase such as serine/threonine kinase, a tyrosine kinase, a porin/channel such as a chloride channel, a potassium channel, a sodium channel, an OMP protein, an ABC transporter (ATP-Binding Cassette-Transporter) such as amino acid transporter, the Na-glucose transporter, the $Na^+$/iodide transporter, an ion transporter such as Light Harvesting Complex, cytochrome c oxidase, ATPase Na/K, H/K, Ca, a cell adhesion receptor such as metalloprotease, an integrin or a cadherin.

An internationally accepted system for the classification and nomenclature of human surface antigens is the "cluster of differentiation" or CD number system which evolved in response to the development of the first monoclonal antibodies (Clark et al., Clinical & Translational Immunology (2016) 5, e57). Accordingly, in a further embodiments, the surface antigen is an antigen specified with a CD number. In this context, surface antigens in accordance with the present invention are known to define a desired cell population or subpopulation, for instance a population or subpopulation of blood cells, e.g. lymphocytes (e.g. T cells, T-helper cells, for example, $CD4^+$ T-helper cells, B cells or natural killer cells), monocytes, or stem cells, e.g. CD34-positive peripheral stem cells or Nanog or Oct-4 expressing stem cells. Examples of T cells include cells such as CMV-specific $CD8^+$ T lymphocytes, cytotoxic T cells, memory T cells and regulatory T cells (Treg). An illustrative example of Treg are $CD4^+CD25^+CD45RA$ Treg cells and an illustrative example of memory T-cells are $CD62L^+CD8^+$ specific central memory T-cells. The surface antigen may also be a marker for a tumor cell. Preferred examples for surface antigens are CD4 receptor, CD3, CD8, CD25, CD19, CD34, CD31, CD45, CD81 or markers of Circulating Tumor cells (CTCs) or exosomes from blood. Accordingly, the method of the present invention, enables the isolation of biological entities, cell populations or subpopulations that are defined by the presence of a specific surface antigen as outlined above.

Binding Domain of the Tagging Agent

According to the method of the present invention, the surface antigen (2) is recognized and bound by a tagging agent (3) via at least one binding domain (4) comprised in the tagging agent (3) via an antigen recognition interaction (9). The one or more binding domain(s) of the tagging agent (3), which specifically bind to the surface antigen (2), may for instance be an antibody or an immunoglobulin, a functional fragment of an antibody or an immunoglobulin, a proteinaceous binding molecule with immunoglobulin/antibody-like functions. Examples of (recombinant) antibody fragments are Fab fragments, Fv fragments, single-chain Fv fragments (scFv), a bivalent antibody fragment such as an (Fab)2'-fragment, diabodies, triabodies (Iliades, P., et al., FEBS Lett (1997) 409, 437-441), decabodies (Stone, E., et al., Journal of Immunological Methods (2007) 318, 88-94) and other domain antibodies (Holt, L. J., et al., Trends Biotechnol. (2003), 21, 11, 484-490). It is also possible to use a bivalent full length (intact) antibody molecule as tagging agent; see the embodiment schematically depicted in FIG. 10 and described herein, infra. In some embodiments of the invention, one or more binding domains may be a bivalent proteinaceous artificial binding molecule such as a dimeric lipocalin mutein that is also known as "duocalin". In some embodiments, the binding domain is monovalent. Examples of monovalent tagging agents include, but are not limited to, a monovalent antibody fragment, a proteinaceous binding molecule with antibody-like binding properties or an MHC molecule. Examples of monovalent antibody fragments include, but are not limited to a Fab fragment, an Fv fragment, and a single-chain Fv fragment (scFv), including a bivalent single-chain Fv fragment. In Examples 3 and 5-8 it has been shown that Fab fragments directed against different CD receptors can efficiently recognize the corresponding surface antigen on target cells and exosomes in accordance with the method of the present invention. Therefore, in one embodiment, the binding domain (4) of the tagging agent (3) is an antigen-binding fragment, such as a Fab.

As mentioned above, an example of a proteinaceous binding molecule with antibody-like functions is a mutein based on a polypeptide of the lipocalin family (see for example, WO 03/029462, Beste et al., Proc. Natl. Acad. Sci. U.S.A. (1999) 96, 1898-1903). Lipocalins, such as the bilin-binding protein, the human neutrophil gelatinase-associated lipocalin, human Apolipoprotein D or human tear lipocalin possess natural ligand-binding sites that can be modified so that they bind a given target. Further examples of a proteinaceous binding molecule with antibody-like binding properties that can be used as tagging agent that specifically binds to the surface antigen include, but are not limited to, the so-called glubodies (see e.g. international patent application WO 96/23879), proteins based on the ankyrin scaffold (Mosavi, L. K., et al., Protein Science (2004) 13, 6, 1435-1448) or crystalline scaffold (e.g., international application WO 01/04144) the proteins described in Skerra, J. Mol. Recognit. (2000) 13, 167-187, AdNectins, tetranectins and avimers. Avimers, including multivalent avimer proteins evolved by exon shuffling of a family of human receptor domains, contain so called A-domains that occur as strings of multiple domains in several surface receptors (Silverman, J., et al., Nature Biotechnology (2005) 23, 1556-1561). Adnectins, derived from a domain of human fibronectin, contain three loops that can be engineered for immunoglobulin-like binding to targets (Gill, D. S. & Damle, N. K., Current Opinion in Biotechnology (2006) 17, 653-658). Tetranectins, derived from the respective human homotrimeric protein, likewise contain loop regions in a C-type lectin domain that can be engineered for desired binding (ibid.). Peptoids, which can act as protein ligands, are oligo (N-alkyl) glycines that differ from peptides in that the side chain is connected to the amide nitrogen rather than the a carbon atom. Peptoids are typically resistant to proteases and other modifying enzymes and can have a much higher cell permeability than peptides (see e.g. Kwon, Y.-U., and Kodadek, T., J. Am. Chem. Soc. (2007)129, 1508-1509).

Yet further examples of suitable proteinaceous binding molecules are an EGF-like domain, a Kringle-domain, a fibronectin type I domain, a fibronectin type II domain, a fibronectin type III domain, a PAN domain, a G1a domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, "Kappabodies" (cf. Ill. et al., Protein Eng (1997) 10, 949-57, a so called "minibody" (Martin et al., EMBO J (1994)13, 5303-5309), a diabody (cf. Holliger et al., PNAS USA (1993) 90, 6444-6448), a so called "Janusis" (cf. Traunecker et al., EMBO J (1991) 10, 3655-3659, or Traunecker et al., Int J Cancer (1992) Suppl 7, 51-52), a nanobody, a microbody, an affilin, an affibody, a knottin, ubiquitin, a zinc-finger protein, an autofluorescent protein or a leucine-rich repeat protein. An example of a nucleic acid molecule with antibody-like functions is an aptamer. An aptamer folds into a defined three-dimensional motif and shows high affinity for a given target structure.

Non-Covalent Ligand-Protein Interaction Mediated by Ligand and Ligand Binding Partner The isolation of the biological entity from the sample is enabled via a reversible complex being formed between the biological entity (1), the tagging agent (3) and the beads (6). Besides the binding domain (4) capable of binding to a surface antigen (2) on the biological entity (1), the tagging agent (3) comprises a second domain which directly or indirectly mediates binding to the beads (6) via a non-covalent protein-ligand interaction. Meaning that one of the components, i.e. the ligand (indicated by reference sign 5) or the ligand binding partner (indicated by reference sign 7) forming the non-covalent protein-ligand interaction is comprised in the tagging agent (3). In FIG. 3, it is exemplary shown that the tagging agent (3) comprises the ligand (5) and the beads (6) comprise the ligand binding partner (7). However, the invention also encompasses the reverse case wherein the ligand (5) is present on the beads (6) and the tagging agent (3) comprises the ligand binding partner (7). Furthermore, as described in detail below it is also envisioned that the tagging agent (3) indirectly binds the beads (6), e.g., via a linking molecule (10) and carrier (11) or via a further ligand (12) and ligand binding partner (13) or via a further ligand (12a) and the ligand binding partner (7) which each form a further reversible protein-ligand interaction.

The non-covalent protein-ligand interaction (indicated by reference sign 8 in the Figures) that is formed between the ligand (5) and the ligand binding partner (7) may be of any desired strength and affinity, as long as it is disruptable or reversible under the conditions under which the method of the invention is performed. The dissociation constant (KD) of the binding between the ligand binding partner (7) and the ligand (5) has a value in the range from about $10^{-2}$ M to about $10^{-13}$ M. Thus, this reversible bond can, for example, have a KD from about $10^{-2}$ M to about $10^{-13}$ M, or from about $10^{-3}$ M to about $10^{-12}$ M or from about $10^{-4}$ M to about $10^{-11}$ M, or from about $10^{-5}$ M to about $10^{-10}$ M. In general, the KD of this bond as well as the KD, $k_{off}$ and $k_{on}$ rate of the non-covalent protein-ligand interactions as well as the antigen recognition binding that form in accordance with the present invention can be determined by any suitable means, for example, by fluorescence titration, equilibrium dialysis or surface plasmon resonance. As described in U.S. Pat. Nos. 7,776,562, 8,298,782 or international application WO 2002/054065 any combination of a ligand (5) and ligand binding partner (7) can be chosen, as long as the ligand (5) and the ligand binding partner (7) are able to reversibly bind or multimerize in a (multivalent) complex to cause an avidity effect is the case for a ligand binding partner comprising multiple binding sites for the ligand.

In accordance with the invention, the ligand (5) is a moiety known to the person skilled in the art as an affinity tag. Accordingly, the ligand binding partner (7) is a corresponding binding partner, for example, an antibody or an antibody fragment, known to bind to the affinity tag. Examples of affinity tags known to the person skilled in the art include but are not limited to an oligohistidine, maltose-binding protein, glutathione-S-transferase (GST), chitin binding protein (CBP) or thioredoxin, calmodulin binding peptide (CBP), FLAG-peptide, the HA-tag (sequence: Tyr-Pro-Tyr-Asp-Val-Pro-Asp-Tyr-Ala, SEQ ID NO: 15,), the VSV-G-tag (sequence: Tyr-Thr-Asp-Ile-Glu-Met-Asn-Arg-Leu-Gly-Lys, SEQ ID NO: 16), the HSV-tag or HSV epitope of the herpes simplex virus glycoprotein D (sequence: Gln-Pro-Glu-Leu-Ala-Pro-Glu-Asp-Pro-Glu-Asp, SEQ ID NO: 17), the T7 epitope (Ala-Ser-Met-Thr-Gly-Gly-Gln-Gln-Met-Gly, SEQ ID NO: 18), maltose binding protein (MBP), the "myc" epitope of the transcription factor c-myc of the sequence Glu-Gln-Lys-Leu-Ile-Ser-Glu-Glu-Asp-Leu (SEQ ID NO: 19), the V5-tag (sequence: Gly-Lys-Pro-Ile-Pro-Asn-Pro-Leu-Leu-Gly-Leu-Asp-Ser-Thr, SEQ ID NO: 20). Further examples of a suitable binding pair include an immunoglobulin domain such as antibody Fc domain as ligand (5) and protein A, protein G or protein L as ligand binding partner (7). Protein A, protein G and protein L are all able to reversibly bind an antibody Fc domain. Alternatively, the ligand binding partner (7) may be a conserved domain of an immunoglobulin which can be bound by an antibody or Fab as the ligand (5). The binding can be disrupted by a change in the buffer conditions, for example, by increasing the salt strength of the buffer or by reducing the pH from, for example, a neutral pH of about 7.0 to a pH of about 3.0 to about 2.5.

In alternative embodiments of the invention, the ligand (5) is a calmodulin binding peptide and the ligand binding partner (7) is multimeric calmodulin as described, e.g., in U.S. Pat. No. 5,985,658. Alternatively, the ligand (5) includes a FLAG peptide and the ligand binding partner (7) includes an antibody that binds to the FLAG peptide, e.g., the FLAG peptide, which binds to the monoclonal antibody 4E11 as described in U.S. Pat. No. 4,851,341. In some embodiments, the antibody that binds to the FLAG peptide may be the commercially available monoclonal antibody M1. In one embodiment, the ligand (5) is an oligohistidine tag and the ligand binding partner (7) includes chelating groups K that bind a transition metal ion and thereby are also able of binding an oligohistidine tag. The disruption of all these binding complexes may be accomplished by metal ion chelation, e.g., calcium chelation, for instance by adding EDTA or EGTA. Calmodulin, antibodies such as 4E11 or chelated metal ions or free chelators may be multimerized by conventional methods, e.g., by biotinylation and complexation with streptavidin or avidin or multimers thereof or by the introduction of carboxyl residues into a polysaccharide, e.g., dextran, essentially as described in Noguchi, A, et al. Bioconjugate Chemistry 3 (1992), 132-137 in a first step and linking calmodulin or antibodies or chelated metal ions or free chelators via primary amino groups to the carboxyl groups in the polysaccharide, e.g., dextran, backbone using conventional carbodiimide chemistry in a second step. In such embodiments, the binding between the ligand (5) and the ligand binding partner (7) can be disrupted by metal ion chelation. The metal chelation may be accomplished, for example, by addition of EGTA or EDTA.

In an alternative embodiment, the non-covalent protein-ligand interaction between the ligand (5) and ligand binding partner (7) may be based on the ALFA system by NanoTag Biotechnologies (Göttingen, Germany), i.e. the ligand (5) is the ALFA-tag recognized by a nanobody, such as the NbAL-FA$^{PE}$ as the ligand binding partner (7), wherein the non-covalent protein-ligand interaction may be disrupted by addition of the ALFA peptide. A detailed disclosure of the ALFA system including the relevant sequences of the tag and nanobodies can be found in Götzke et al., Nature Communications 10 (2019), 1-12.

The method of the present invention has exemplary been validated by a cell isolation method, wherein the non-covalent protein-ligand interaction (8) formed between the ligand (5) and the ligand binding partner (7) constitutes a biotin-avidin-like interaction. For example, as shown in Examples 3 and 4, for the isolation of CD3$^+$ cells from a blood sample, the ligand (5) is a Twin-Strep-tag® comprised in the CD3 Fab-Strep (tagging agent (3)) and the ligand binding partner (7) is Strep-Tactin® present on the beads (6).

Accordingly, in one embodiment of the invention, the non-covalent protein-ligand interaction is mediated via a biotin-avidin-like interaction, i.e. the ligand (5) includes biotin or a biotin analog or derivative thereof and the ligand binding partner (7) include a streptavidin mutein or an avidin mutein that reversibly binds to biotin or the analog or derivative thereof. Therefore, in accordance with the invention, the ligand (5) is a biotin derivative that reversibly binds to streptavidin or avidin, and the ligand binding partner (7) is streptavidin, avidin, a streptavidin analog or an avidin analog that reversibly binds to the respective biotin derivative. Preferably, the ligand (5) is a streptavidin or avidin binding peptide and the ligand binding partner (7) is streptavidin, avidin, a streptavidin analog or an avidin analog that reversibly binds to the respective streptavidin or avidin binding peptide.

In preferred embodiments the ligand (5) is a streptavidin-binding peptide that comprises or consists of one of the following sequences:

a) -Trp-Xaa-His-Pro-Gln-Phe-Yaa-Zaa- (SEQ ID NO: 1), wherein Xaa is any amino acid and Yaa and Zaa are both Gly or Yaa is Glu and Zaa is Lys or Arg, b) -Trp-Arg-His-Pro-Gln-Phe-Gly-Gly- (SEQ ID NO: 2), c) -Trp-Ser-His-Pro-Gln-Phe-Glu-Lys- (SEQ ID NO: 3), d) a sequential arrangement of at least two streptavidin binding peptides, wherein each peptide binds streptavidin, wherein the distance between two peptides is at least 0 and not greater than 50 amino acids and wherein each of the at least two peptides comprises the amino acid sequence -His-Pro-Baa- in which Baa is selected from the group consisting of glutamine, asparagine and methionine, and wherein the sequential arrangement comprises at least the amino acid sequence -His-Pro-Baa-Xaa-His-Pro-Baa-(SEQ ID NO: 21), in which Xaa can be 0-50 amino acids of any type, and in which Baa is selected from the group consisting of glutamine, asparagine and methionine, e) a sequential arrangement as recited in d), wherein one of the at least two peptides comprises the sequence -His-Pro-Gln-, and wherein the sequential arrangement comprises at least the amino acid sequence -His-Pro-Gln-Xaa-His-Pro-Gln-(SEQ ID NO: 22), in which Xaa can be 0-50 amino acids of any type, f) a sequential arrangement as recited in d), wherein one of the peptides comprises an amino acid sequence -His-Pro-Gln-Phe- (SEQ ID NO: 4), and wherein the sequential arrangement comprises at least the amino acid sequence -His-Pro-Gln-Phe-Xaa-His-Pro-Gln-Phe-(SEQ ID NO: 23), in which Xaa can be 0-50 amino acids of any type, g) a sequential arrangement as recited in d) wherein at least one peptide includes at least the amino sequence -Oaa-Xaa-His-Pro-Gln-Phe-Yaa-Zaa- (SEQ ID NO: 5), where Oaa is Trp, Lys or Arg, Xaa is any amino acid and where either Yaa and Zaa are both Gly or Yaa is Glu and Zaa is Lys or Arg, and wherein the sequential arrangement comprises at least the amino acid sequence -Oaa-Xaa-His-Pro-Gln-Phe-Yaa-Zaa-Xaa-Oaa-Xaa-His-Pro-Gln-Phe-Yaa-Zaa-(SEQ ID NO: 24), in which Xaa at position 9 can be 0-50 amino acids of any type, where Oaa is Trp, Lys or Arg, Xaa at position 2 and 11 is any amino acid, and where either Yaa and Zaa are both Gly or Yaa is Glu and Zaa is Lys or Arg, h) a sequential arrangement as recited in d) wherein at least one peptide includes at least the amino acid sequence -Trp-Xaa-His-Pro-Gln-Phe-Yaa-Zaa- (SEQ ID NO: 6) where Xaa is any amino acid and where either Yaa and Zaa are both Gly or Yaa is Glu and Zaa is Lys or Arg, and wherein the sequential arrangement comprises at least the amino acid sequence -Trp-Xaa-His-Pro-Gln-Phe-Yaa-Zaa-Xaa-Trp-Xaa-His-Pro-Gln-Phe-Yaa-Zaa-(SEQ ID NO: 25), in which Xaa at position 9 can be 0-50 amino acids of any type, where Xaa at position 2 and 11 is any amino acid, and where either Yaa and Zaa are both Gly or Yaa is Glu and Zaa is Lys or Arg, i) a sequential arrangement as recited in d) wherein at least one peptide includes at least the amino acid sequence -Trp-Ser-His-Pro-Gln-Phe-Glu-Lys- (SEQ ID NO: 7), and wherein the sequential arrangement comprises at least the amino acid sequence -Trp-Ser-His-Pro-Gln-Phe-Glu-Lys-Xaa-Trp-Ser-His-Pro-Gln-Phe-Glu-Lys-(SEQ ID NO: 26), in which Xaa can be 0-50 amino acids of any type, j) the amino acid sequence -Trp-Ser-His-Pro-Gln-Phe-Glu-Lys-(Xaa)n-Trp-Ser-His-Pro-Gln-Phe-Glu-Lys- (SEQ ID NO: 8) wherein Xaa is any amino acid and n is an integer from 0 to 12.

k) an amino acid sequence selected from the group consisting of Trp-Arg-His-Pro-Gln-Phe-Gly-Gly (SEQ ID NO: 2), Trp-Ser-His-Pro-Gln-Phe-Glu-Lys (SEQ ID NO: 9), Trp-Ser-His-Pro-Gln-Phe-Glu-Lys-(GlyGlyGlySer)$_3$-Trp-Ser-His-Pro-Gln-Phe-Glu-Lys (SEQ ID NO: 10), Trp-Ser-His-Pro-Gln-Phe-Glu-Lys-(GlyGlyGlySer)$_2$-Trp-Ser-His-Pro-Gln-Phe-Glu-Lys (SEQ ID NO: 11) or Trp-Ser-His-Pro-Gln-Phe-Glu-Lys-(GlyGlyGlySer)$_2$-Gly-Gly-Ser-Ala-Trp-Ser-His-Pro-Gln-Phe-Glu-Lys (SEQ ID NO: 12).

In these embodiments, the ligand binding partner (7) include the streptavidin mutein (analog) Val$^{44}$-Thr$^{45}$-Ala$^{46}$-Arg$^{47}$ (SEQ ID NO: 13) or the streptavidin mutein (analog) Ile44-Gly$^{45}$-Ala$^{46}$-Arg$^{47}$ (SEQ ID NO: 14), both of which are described, e.g., in U.S. Pat. No. 6,103,493 and are commercially available under the trademark Strep-Tactin®. Such multimeric streptavidin muteins may also be referred to as multimerized Strep-Tactin. In one embodiment, the ligand binding partner (7) is based on the Strep-Tactin®XT system or the Strep-Tactin®XTS system (IBA GmbH, Göttingen, Germany). Those and further components of the non-covalent protein ligand interaction that are encompassed by the present invention as ligand (5) or ligand binding partner (7) are described in detail in the international applications WO 02/077018 A1, WO 2014/076277 A1 and WO 2017/186669 A1 all of which are herein expressly incorporated by reference.

Beads

The beads (illustrated by reference sign 6 in the Figures) used in the non-chromatographic methods of the present invention can be any particulate material as long as they are freely movable particles, i.e. that they can float within a liquid when the container containing the liquid is moved or the liquid is brought in motion. When the container and liquid is kept still the beads are able to settle to the bottom of the container.

In one embodiment of the invention, the beads (6) are non-magnetic beads. Non-magnetic or non-magnetizable beads, include derivatized silica or a crosslinked gel typically manufactured in a bead form. Such crosslinked gel beads may be based on a natural polymer, i.e. on a polymer class that occurs in nature. For example, a natural polymer in form of a bead in accordance with the present invention is based is a polysaccharide. A respective polysaccharide is generally crosslinked. An example of a polysaccharide matrix is an agarose gel (for example, Superflow™ agarose or a Sepharose® material such as Superflow™ Sepharose® that are commercially available in different bead and pore sizes) or a gel of crosslinked dextran(s). A further illustrative example is a particulate cross-linked agarose matrix, to which dextran is covalently bonded, that is commercially available (in various bead sizes and with various pore sizes) as Sephadex® or Superdex®, both available from GE Healthcare. Another illustrative example of such bead material is Sephacryl® that is also available in different bead and pore sizes from GE Healthcare. Such natural polymers, in particular agarose beads have been used in the experiments performed in accordance with the present invention, see Examples 3-5, 7 and 8. Therefore, in one embodiment of the present invention, the beads comprise a natural polymer, preferably a crosslinked polysaccharide, more preferably agarose. It is noted that such materials are also used as stationary phases in chromatographic methods. However, in such methods the materials are usually packed as stationary column material which does not move; see also description of the chromatographic methods of the present invention, infra.

Crosslinked gel beads may also be based on a synthetic polymer, i.e. on a polymer class that does not occur in nature. Usually such a synthetic polymer on which the beads for cell separation are based are a polymer that has polar monomer units, and which is therefore in itself polar. Such a polar polymer is hydrophilic. Hydrophilic molecules, also termed lipophobic, contain moieties that can form dipole-dipole interactions with water molecules. Hydrophobic molecules, also termed lipophilic, have a tendency to separate from water. Illustrative examples of suitable synthetic polymers are polyacrylamide(s), a styrene-divinylbenzene gel and a copolymer of an acrylate and a diol or of an acrylamide and a diol. An illustrative example is a polymethacrylate gel, commercially available as a Fractogel®. A further example is a copolymer of ethylene glycol and methacrylate, commercially available as a Toyopearl®. In some embodiments beads may also include natural and synthetic polymer components, such as a composite matrix or a composite or a co-polymer of a polysaccharide and agarose, e.g., a polyacrylamide/agarose composite, or of a polysaccharide and N,N'-methylenebisacrylamide. An illustrative example of a copolymer of a dextran and N,N'-methylenebisacrylamide is the above-mentioned Sephacryl® series of material. Derivatized silica may include silica particles that are coupled to a synthetic or to a natural polymer. Examples of such embodiments include, but are not limited to, polysaccharide grafted silica, polyvinyl-pyrrolidone grafted silica, polyethylene oxide grafted silica, poly(2-hydroxyethylaspartamide) silica and poly(N-isopropylacrylamide) grafted silica. However, in one embodiment of the present invention, the beads do not comprise a synthetic polymer.

Figure 1:
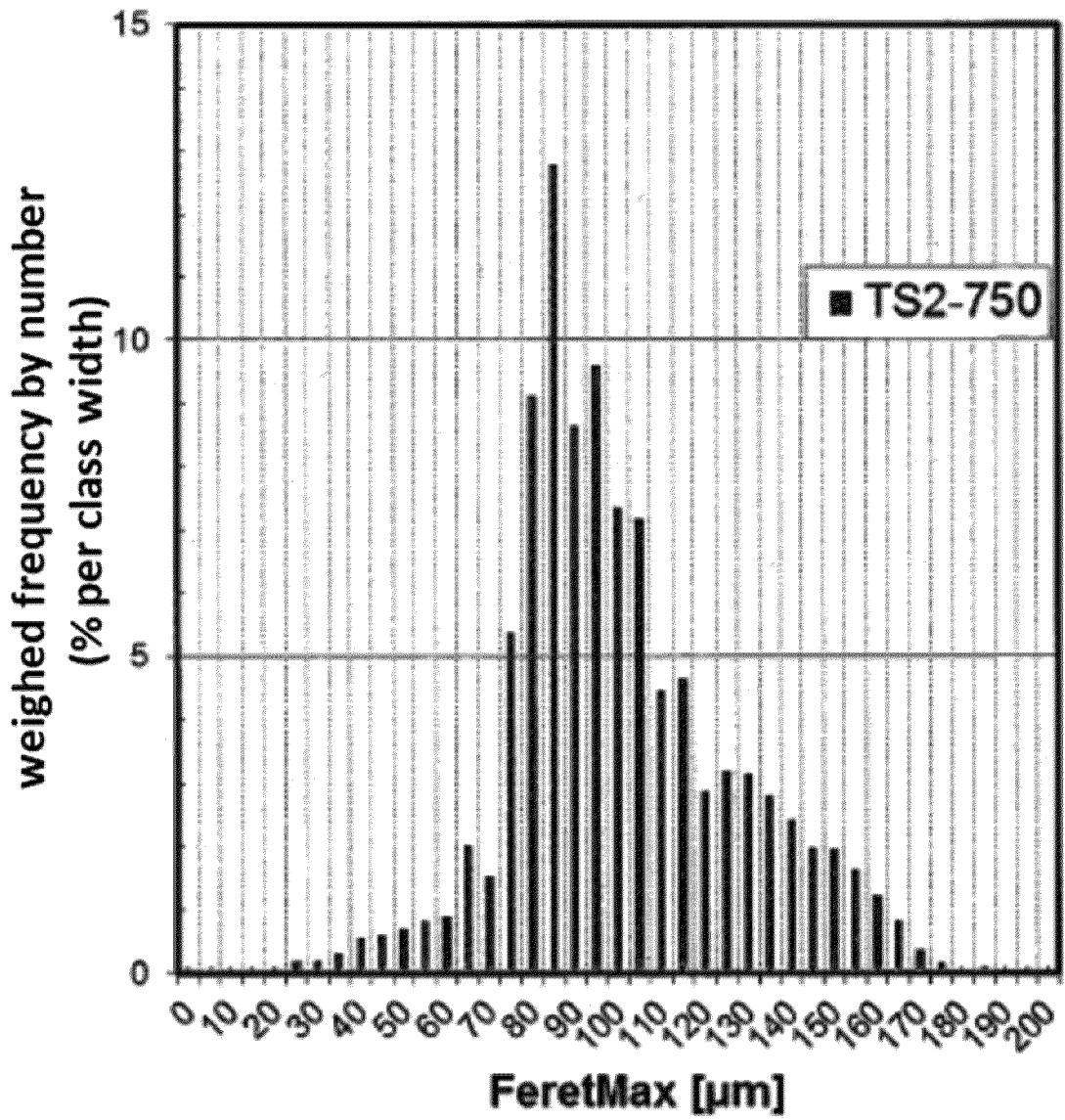
FIG. 1: Size distribution (diameter) of commercially available agarose particles (IBA GmbH, Göttingen Germany). Bead diameters range from about 30 µm to about 180 µm with most of the beads having a diameter between 80 and 120 µm.

As shown in FIG. 1, commercially available agarose beads are a mixture of beads of varying diameter between 30-180 µm. Experiments performed in accordance with the present invention surprisingly revealed that cells preferentially bind small beads having a diameter of less than 70 µm. Therefore, using a mixture of beads decreases the efficiency of cell isolation procedures due to the presence of large beads within the suspension that do not bind the target cells. This was confirmed by applying small beads (40-60 µm diameter) and large beads (>140 µm diameter) to the method of the present invention; see Example 5. As shown in FIG. 6A, using small beads result in efficient isolation of CD81V cells from buffy coat, whereas the use of large beads only result in a marginal yield of the target cells. Therefore, in an additional or alternative embodiment, the beads are characterized to have a diameter of about 30-100 µm, preferably 40-60 µm. As used herein "small" beads are defined to have a diameter of 40-60 µm and "large" beads are defined to have a diameter of 140-180 µm.

The beads themselves are not designed to be capable of specifically binding the biological entity (1). However, they can comprise a component of the non-covalent protein-ligand interaction described, supra, i.e. the ligand binding partner (7) or the ligand (5) in case of a direct interaction between the tagging agent (3) and the beads (6).

As shown in Examples 3 and 5, the beads (6) can comprise the ligand binding partner (7) such as in the Strep-Tactin®-coated agrose beads (IBA GmbH, Göttingen, Germany) used in the experiments while the tagging agent (3) is a Strep-tagged Fab fragment with the binding domain (4) being a Fab and the ligand (5) being a Strep-tag. Accordingly, in one embodiment of the invention, the tagging agent (3) comprises an antigen-binding fragment (Fab) as the binding domain (4) which is linked to the ligand (5) and the beads (6) comprise the ligand binding partner (7) which immobilizes the tagging agent on the beads.

Figure 11:
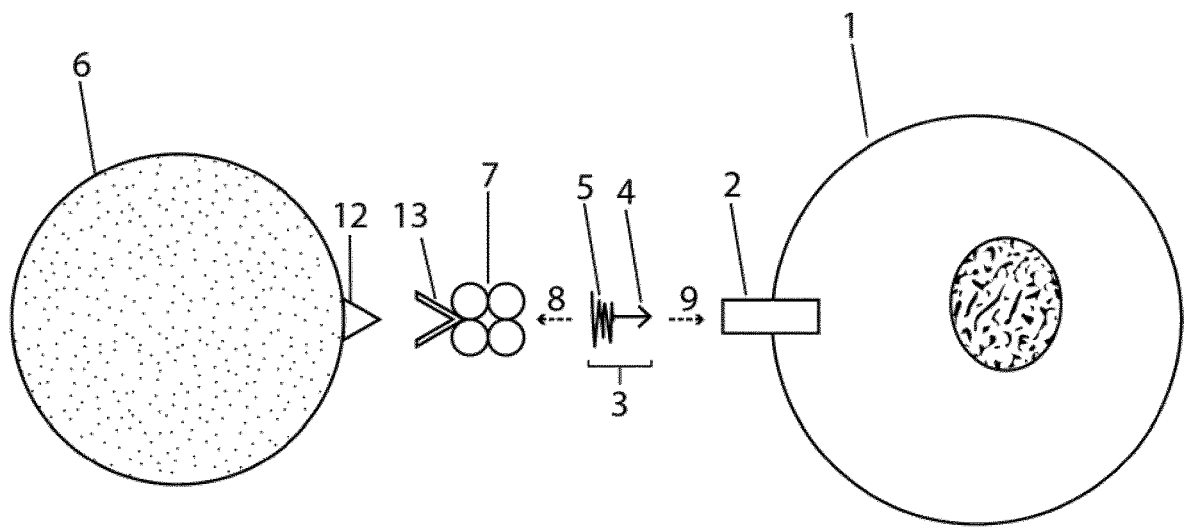
FIG. 11: (A) Schematic representation of a method of isolating a biological entity (1) representing a further development of the method depicted in FIG. 3, wherein the binding of the biological entity (1) via the tagging agent (3) to the beads (6) is indirectly mediated by further protein-ligand interaction between a further ligand (12) present on the beads (6) and a further ligand binding partner (13) fused to the ligand binding partner (7). (B) Schematic representation of a method of isolating a biological entity (1) representing a further development of the method depicted in FIG. 3, wherein the binding of the biological entity (1) via the tagging agent (3) to the beads (6) is indirectly mediated by further protein-ligand interaction between a further ligand (12a) present on the beads (6) and the ligand binding partner (7).
Figure 11:
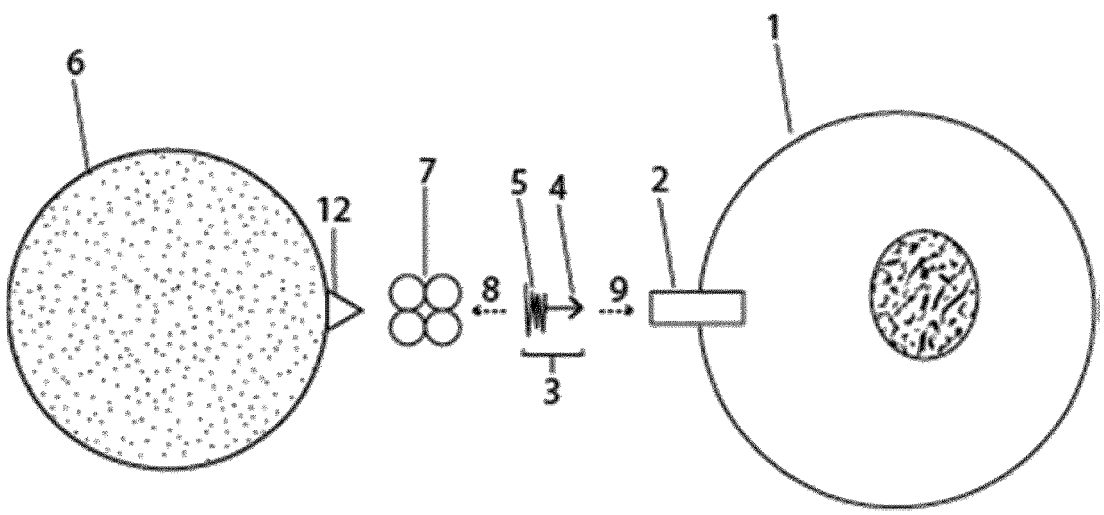

In another embodiment of the present invention, the method comprises a further protein-ligand interaction between the ligand binding partner (7) and the beads (6). As schematically depicted in FIG. 11A, the beads comprise a further ligand (12) which is recognized by a further ligand binding partner (13) comprised on the ligand binding partner (7). Accordingly, the ligand binding partner (7) is indirectly immobilized on the beads (6) via the protein-ligand interaction between the further ligand (12) and the further ligand binding partner (13). The components used in this embodiment of the invention are described in international application WO 2015/166049. As described therein, the further ligand binding partner (13), e.g., produced as a fusion protein with the ligand binding partner (7) may be a hexa-histidine tag or glutathione-S-transferase. The further ligand (12) associated with the beads (6) may be chelating groups that have a transition metal complexed thereto and are capable of binding to an oligohistidine peptide such as a hexa-histidine tag, or if glutathione-S-transferase is used as further ligand binding partner (13), the ligand (12) may be glutathione.

In an alternative embodiment, the beads comprise a further ligand (12a) which is recognized by the ligand binding partner (7); see FIG. 11B. The components used in this embodiment of the invention are also described in international application WO 2015/166049. As described therein, the further ligand (12a) may be biotin or a derivative of biotin. Examples of a suitable derivative of biotin including, but are not limited to, desthiobiotin, iminobiotin, 2-(4'-hydroxyazobenzene) benzoic acid (HABA) or a streptavidin binding peptide. For example, the biotin binds to the free binding sites of the ligand binding partner (7), which is preferably streptavidin, thereby immobilizing the target cells on the beads (6). Accordingly, the beads can be made of biotin-agarose obtainable for example from IBA GmbH, Göttingen, Germany. This method has the advantage that no linking molecule (10), i.e., the Strep-tagged recombinant antigen, is needed on the beads (6) but that the further ligand (12a) can be directly coupled to the beads. Thus, biotin agarose, a common and commercially available product, can be used.

However, the methods disclosed in WO 2015/166049 relate to a chromatographic method of isolating a target cell wherein the chelating groups or glutathione-S-transferase and the biotin or derivatives thereof, respectively are attached to the stationary phase. It is prudent to expect that transferring the components described therein to a non-chromatographic method as described herein, i.e. by using freely movable beads which are kept in continuous motion confers the same advantages for the isolation of biological entities such as an avidity effect and improved accessibility of the surface antigen on the biological entity.

Competing Agent

Dissociation of the components, which immobilizes the biological entity indirectly on the beads, may be induced, for example, by a change in conditions. Such a change in conditions may for instance be a change in the ionic strength of the buffer or a change in temperature. In some embodiments a competing reagent is employed in order to induce dissociation of the reversible non-covalent complex between surface antigen (2) and tagging agent (3), tagging agent (3) and beads (6). The competing reagent may be able to associate to, occupy or block the (further) ligand or (further) ligand binding partner. By using a competing reagent with a particularly high affinity for the ligand or ligand binding partner or by using an excess of the competing reagent the non-covalent protein-ligand interaction may be disrupted. The biological entity (1) is allowed to elute from the beads. The eluate and thereby the biological entity (1) is collected.

The term "competing agent" as used herein refers to any reagent or condition that is able to reduce, interfere with or abrogate the formation of a complex between a pair of binding agents or binding sites, such as the ligand and ligand binding partner, and binding domain and the surface antigen. The term "competition" is meant to refer any interference with binding, regardless of the nature of such interference. Such interference may also be in some embodiments a non-competitive binding to a certain binding site. An example of such a competition mechanism is the metal chelation by a chelating reagent such as EDTA or EGTA, when the reversibly bond is mediated by complexed metal ions such as $Ca^{2+}$, $Ni^{2+}$, $Co^{2+}$, or $Zn^{2+}$. This mechanism applies for binding pairs such as calmodulin and calmodulin binding peptides that bind in the presence of $Ca^{2+}$ or for binding pairs that are used in Immobilized Metal-chelate Affinity Chromatography (IMAC). In some embodiments, competition is provided by a change in pH or the salt strength of a buffer and the competing reagent is then either an increased or decreased pH or salt strength. A change in pH can be, for example, used for displacing/disrupting the binding of streptavidin to a streptavidin binding peptide or for displacing/disrupting the binding between protein A or protein G and an antibody Fc domain.

In case the non-covalent protein-ligand interaction is formed between an affinity tag as the ligand (5) and a corresponding antibody or antibody fragment as the ligand binding partner (7) the complex/interaction formed can be disrupted competitively by adding the free ligand, i.e. the free peptide (epitope tag) or the free protein (such as MBP or CBP).

As outlined herein, the competing reagent in general may disrupt every interaction of the components with each other or the biological entity. In preferred embodiments, the competing agent is able to disrupt the binding of the ligand to the ligand binding partner. The competing reagent may also be capable of competitively bind to the ligand binding partners.

Since the bond between the ligand binding partner (7) and the ligand (5) of the tagging agent (3) can be disrupted by addition of a competition agent, the biological entity (1) can be subsequently eluted under mild conditions under which the tagging agent (3) completely dissociates from the biological entity (1), thereby avoiding that the tagging agent (3) affects the functional status of the biological entity (1). The method of the invention, thus, does not only have the advantage that it allows for the isolation/purification of, e.g., target cell population (or any other biological entity described herein) without altering the functional status of the cell population that is defined by a common specific receptor molecule. Rather, this method also has the added advantage that it entirely abolishes the need to use magnetic beads for cell purification and thereby simplifies any further handling of the cell and opens the way to automatization of the isolation of biological entities, as also described herein.

In one embodiment, the competing agent is biotin or a biotin derivative. Biotin or a biotin derivative is particularly preferred in embodiments of the invention that make use of streptavidin, a streptavidin mutein, avidin or an avidin mutein. Examples of such biotin derivatives include, but are not limited to, desthiobiotin, iminobiotin, 2-(4'-hydroxyazobenzene) benzoic acid (HABA) or a streptavidin binding peptide including the streptavidin binding peptides that are illustratively mentioned herein.

Linking Molecule

Figure 7:
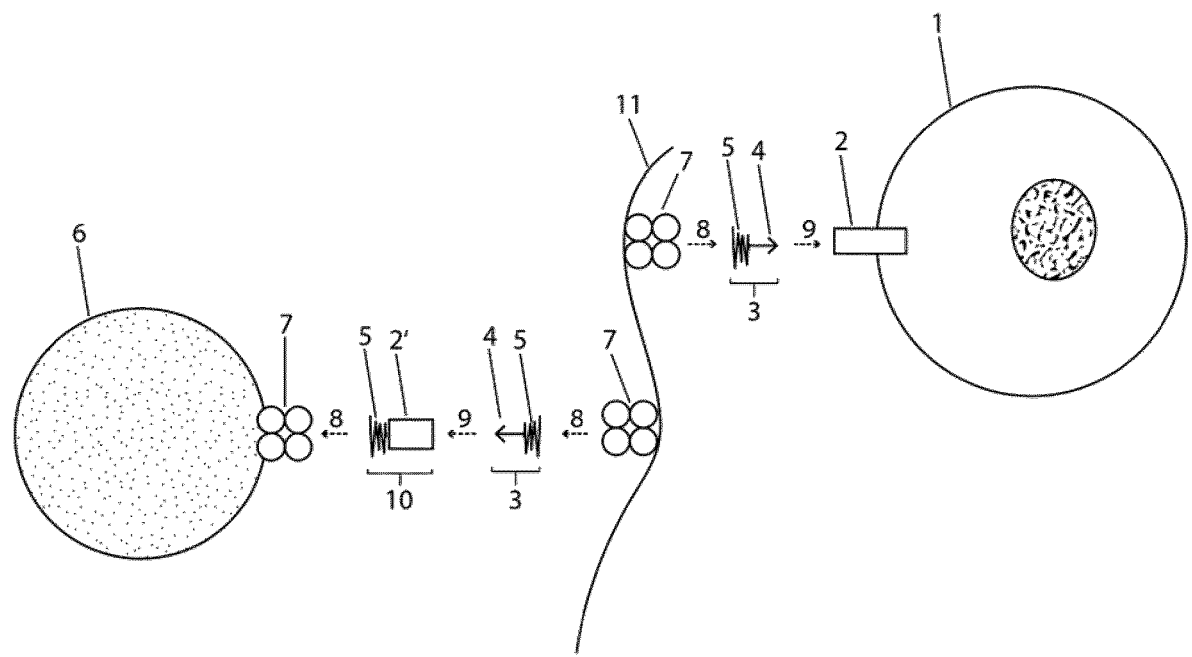
FIG. 7: Schematic representation of a method of isolating a biological entity, wherein the biological entity (1) indirectly binds a bead (6) via a linking molecule (10) and carrier (11) forming an "antibody polymer". High molecular weight dextran as the carrier (11) can be chemically modified to bind many antibodies or Fab fragments (5) in active form. This antibody polymer can bind an antigen (2) present on cells but still has free binding sites for the recombinant antigen (2') present on another structure like a linking molecule (10) bound to the surface of an agarose bead (6) and is therefore highly suitable for the isolation of biological entities. The principle depicted has been applied in Examples 6-8.
Figure 10:
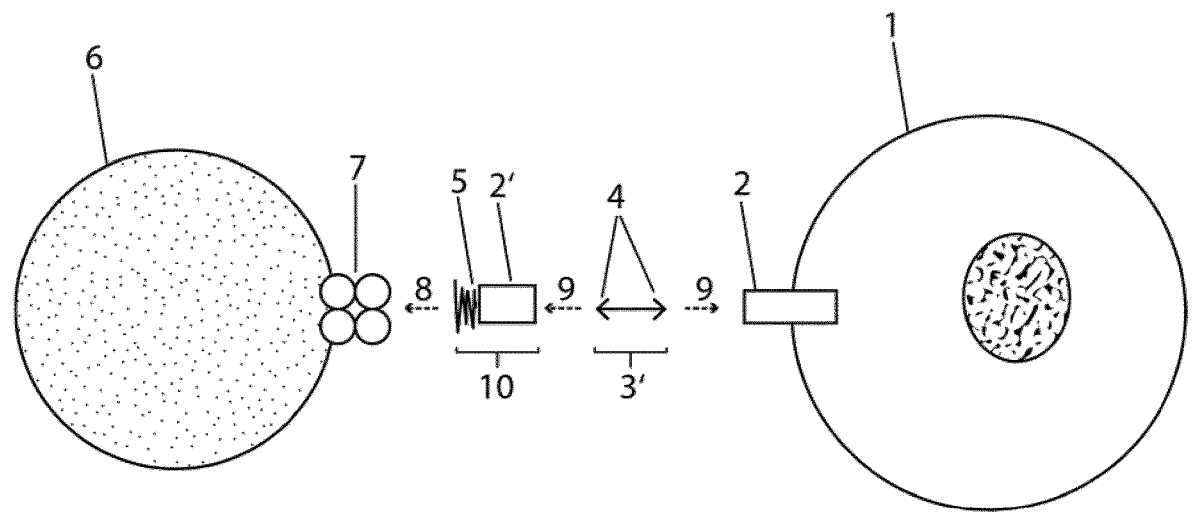
FIG. 10: Schematic representation of a method of isolating a biological entity, wherein the biological entity (1) indirectly bind the beads (6) via a linking molecule (10). Thereby, the tagging agent (3') comprises at least two binding domains (4), one of which recognizes the antigen (2) on the surface of the biological entity and the other one to a recombinant antigen (2') on a linking molecule (10) immobilized on a bead (6) via a non-covalent protein-ligand interaction (8).

As indicated, supra, the binding of the biological entity (1) via the tagging agent (3) to the beads (6) can be indirectly mediated by non-covalent protein-ligand interaction. Therefore, in an additional or alternative embodiment of the invention, the binding between the tagging agent (3) and the beads (6) is mediated via a linking molecule (illustrated by reference sign 10 in the Figures). Such indirect binding is schematically depicted in FIGS. 7 and 10. In this example, the beads (6) comprise a ligand binding partner (7) which is recognized by a ligand (5) comprised in the linking molecule (10). The linking molecule (10) in turn comprises an antigen (illustrated by reference sign 2' in the Figures) which is recognized by the tagging agent (3).

Accordingly, the linking molecule (10) comprises a component for a non-covalent protein-ligand interaction (8), e.g., a ligand (5), and an antigen (2'). The ligand (5) on the linking molecule (10) and the binding partner (7) on the beads (6), or vice versa, form a non-covalent protein-ligand interaction (8) as described in detail, supra. In order to avoid confusion of the antigen (2') of the linking molecule (10) with the antigen (2) present on the biological entity (1), the antigen (2') is designated as "recombinant antigen" (2'). The recombinant antigen (2') of the linking molecule resembles the surface antigen (2) in such a manner that it is usually a soluble portion thereof. Preferably, the recombinant antigen (2') comprises an entire extracellular region or a fragment of the extracellular region (domain) of the surface antigen (2). Fragments of an extracellular region (domain) or an entire extracellular domain usually are usually easy to express (by standard recombinant gene expression technology) and comprise an epitope that can be recognized by the binding domain (4) of the tagging agent (3). The extracellular fragment may have the same or a different epitope than the tagging agent. In case the recombinant antigen (2') shares the epitope with the antigen (2) (meaning the recombinant antigen includes in its sequence the epitope that the tagging agent (3) recognizes in the antigen (2)), than the methods of the invention can be carried out with using only (one kind) of tagging agent (3). In case the recombinant antigen (2) does not share the epitope with the antigen (2) (meaning the recombinant antigen (2') does not include in its sequence the epitope that the tagging agent (3) recognizes in the antigen (2)) as it may be the case, if the tagging agent (3) binds to one extracellular domain of the surface antigen (2) while the recombinant antigen (2') is (part/derived from) a different extracellular domain), then in addition to the tagging agent (3) a second tagging agent recognizing the different extracellular domain is used in the methods of the invention.

One purely illustrative example of a linking molecule (10) is shown in FIG. 7 and in Example 7. Here, the human CD4 extracellular domain without signal peptide that comprises a membrane anchor has been fused to a streptavidin binding peptide referred to as Twin-Strep-tag®, i.e. this linking molecule (10) comprises a soluble form of CD4 that is recognized by the tagging agent (3). In this illustrative example, the tagging agent (3) is an antibody targeting CD4 that has been modified to carry a streptavidin binding peptide referred to as Twin-Strep-tag® (ligand). Of course, the linking molecule (10) is not limited to human CD4. A person skilled in the art will readily recognize that virtually every antigen or cell marker can be employed within the methods of the invention. If the sequence of the antigen is known, it can be modified to carry a ligand as described herein. In addition, a fragment of a receptor molecule may be used. This fragment is preferably soluble and comprises an extracellular domain or a part of an extracellular domain of the receptor molecule present on the surface of a biological entity.

In one embodiment of the method of the present invention comprising a linking molecule (10), the tagging agent is bivalent, i.e. comprises at least two binding domains (4) which are linked to each other. Such tagging agent is referred to by reference sign (3') in the Figures. As schematically depicted in FIG. 10, one binding domain of the tagging agent (3') binds to the surface antigen (2) on the biological entity (1) and the other binding domain (4) binds the recombinant antigen (2') of the linking molecule (10). Hence, the tagging agent (3') of this specific embodiment concatenates the biological entity (1) with the linking molecule (10), wherein the linking molecule has been immobilized on the beads (6). Thereby, the biological entity (1) is immobilized indirectly on the beads (6). An elution of the biological entity is still possible because the interaction of the ligand (5) of the linking molecule (10) with the ligand binding partner (7) on the beads (6), or vice versa, may be disrupted by a competition reagent or by altering the physico-chemical environment. Preferably, the at least two binding domains (4) of the tagging agent (3') are linked by a spacer. In a preferred embodiment, the tagging agent (3') does not comprise a component of the non-covalent protein-ligand interaction, for example a ligand (5).

In one embodiment of the method of the invention, where a linking molecule (10) mediates the indirect binding of the tagging agent (3) to the beads (6), the method comprises at least two tagging agents (3) capable of recognizing the surface antigen (2) and the recombinant antigen (2'), wherein the at least two tagging agents (3) can be the same or different as outlined above. In a further embodiment thereof the at least two tagging agents (3) bind a carrier (11) via a non-covalent protein-ligand interaction. This embodiment is schematically depicted in FIG. 7. The at least two tagging agents (3) are immobilized on the carrier (11) via a non-covalent protein-ligand interaction (8) formed between the ligand (5) and the ligand binding partner (7) as described above. For example, the ligand binding partner (7) can be bound to the carrier (11) and the ligand (5) can be comprised within the tagging agents (3). So to say, the carrier (11) provides a scaffold as it can bind at least two tagging agents (3).

Figure 9:
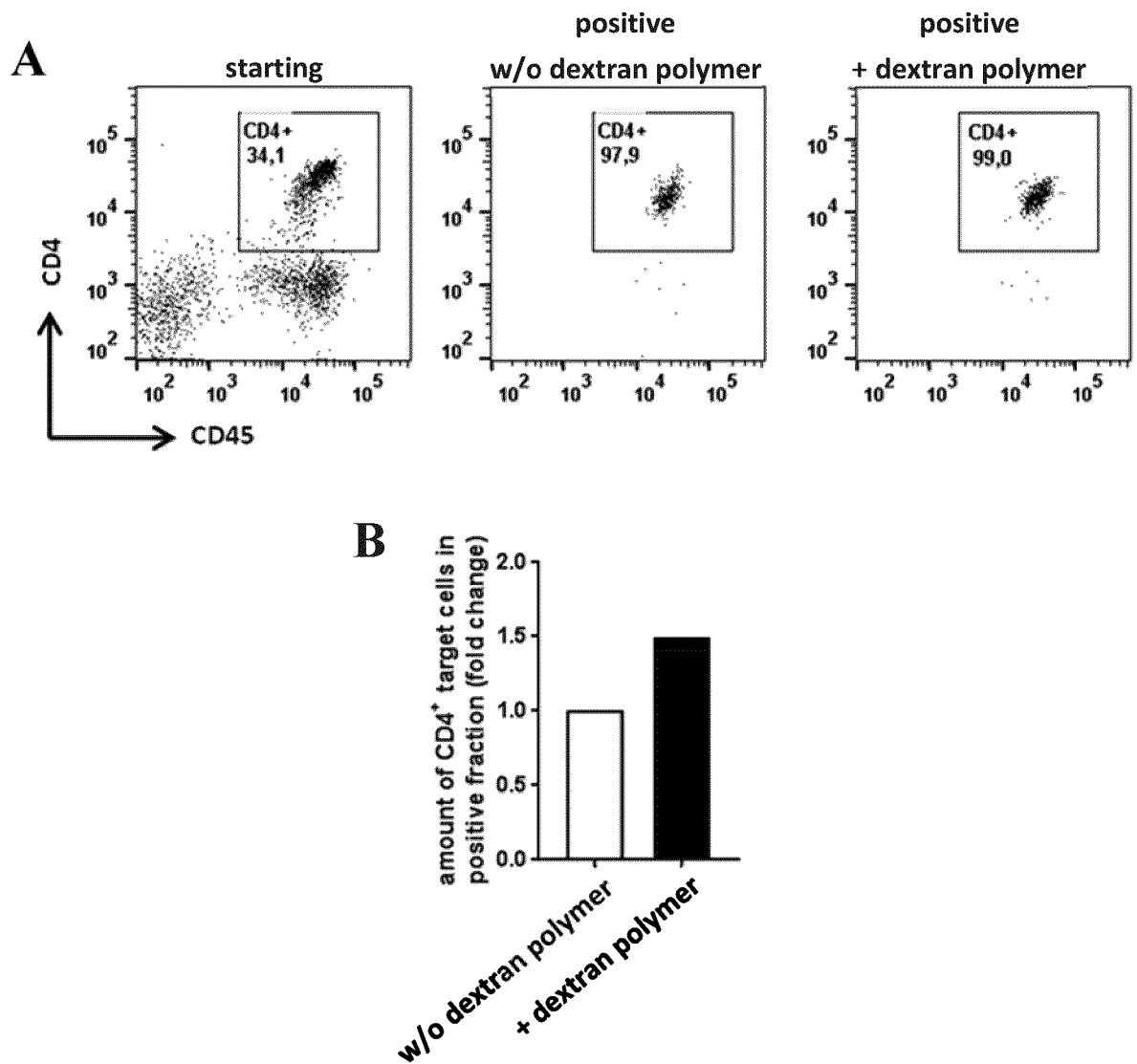
FIG. 9: FACS analyses of CD4+ cells enriched from human PBMCs (A, B) and human whole blood (C, D) via a Strep-Tactin®/dextran polymer using the "moving batch mode" of the FABian® device with agarose beads having a diameter of 90 μm (+/−50 μm) as shown in dot plot (A) and bar chart (B) in the indicated fractions.
Figure 9:
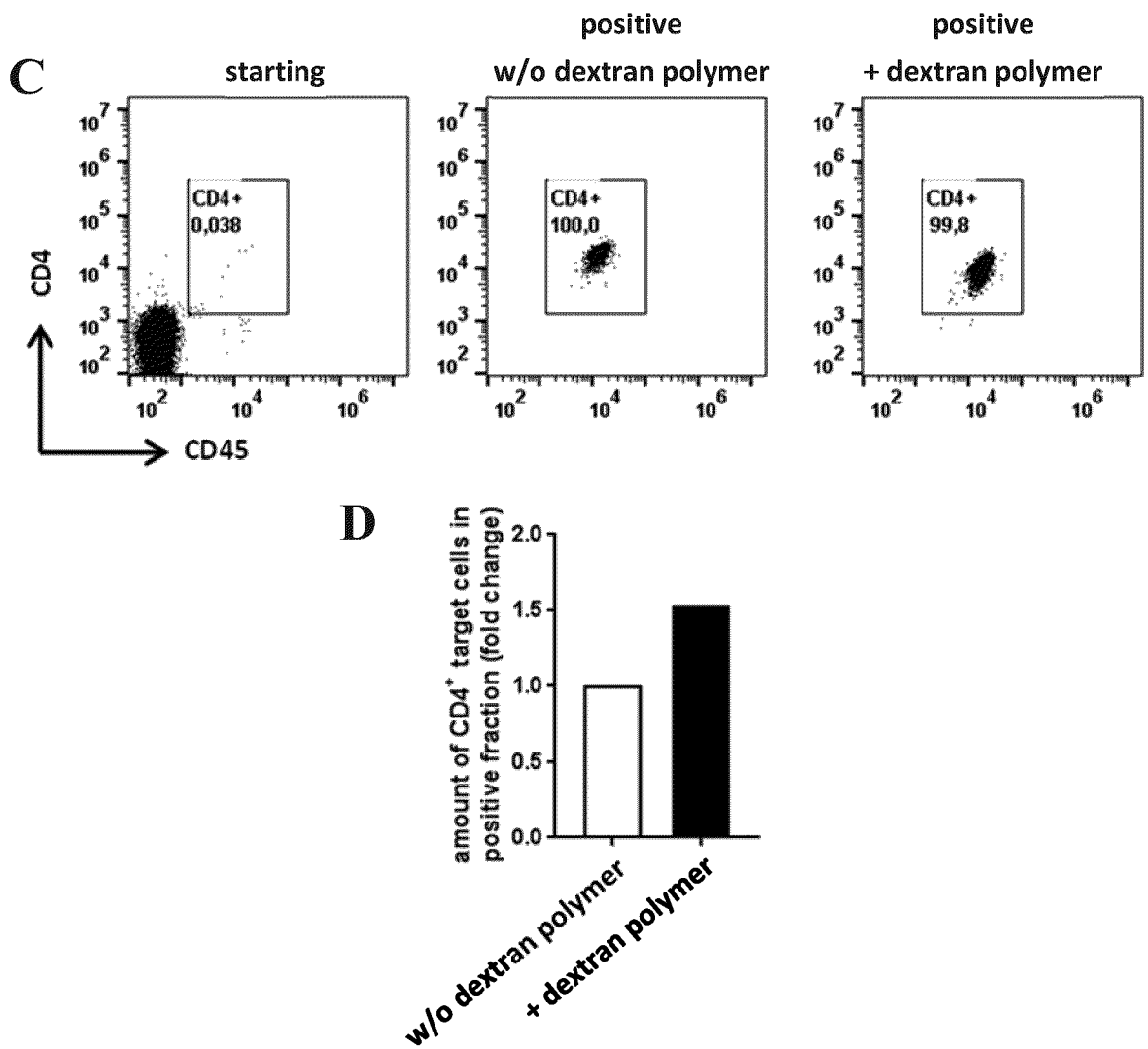

Such embodiment of the method of the invention has exemplary been performed in Example 7, wherein CD4+ cells have been purified from human PBMCs, i.e. the antigen (2) is CD4. The procedure comprises a carrier (11) which is high molecular weight dextran having at least two ligand binding partners (7), i.e. Strep-Tactin® covalently coupled thereto. The tagging agents (3) are anti-human CD4 Strep-tagged Fab fragments, wherein the binding domains (4) are CD4 Fab fragments and the ligands (5) being part of the protein-ligand-interaction are Strep-tags. At least two of those tagging agents (3) are immobilized on the Strep-Tactin®/dextran carrier (10-7) via a non-covalent protein-ligand interaction (8) between the Strep-tag (5) and the Strep-Tactin® (7). One of the at least two tagging agents (3) binds the CD4 antigen (2) on the biological entity and the other tagging agent (3) binds a linking molecule (10) via an antigen recognition interaction (9). The linking molecule (10) is a CD4-Twin-Strep-tag® fusion protein comprising the antigen (2') which is the recombinantly expressed extracellular domain of the CD4 protein and the ligand (5) being part of the non-covalent protein-ligand-interaction which is a Twin-Strep-tag®. The beads (6) are coated with the ligand binding partner (7), i.e. Strep-Tactin® which is bound by the ligand (5), i.e. Twin-Strep-tag® of the linking molecule (10). As shown in FIG. 9, the use of the additional dextran polymer as a carrier (11) increases the yield of target cells isolated from PBMCs (A, B) and whole blood (C, D) compared to the isolation procedure without the dextran polymer.

Carrier

As depicted in FIG. 7, the soluble carrier (11) contains a plurality, i.e. at least two, ligand binding partners (7), which are capable of reversibly binding to the ligand (5), or vice versa. For the sake of illustration and convenience only, in the following, the carrier is described as having the ligand binding partner (7) bound thereto, whereas the tagging agent (3) comprises the ligand (5) but the reverse case is also encompassed by the present invention. Accordingly, the tagging agents (3) bind via their ligand (5) to a ligand binding partner (7) on the carrier (11). When the carrier (11) and a plurality of the tagging agents (3) bind to each other, they form a multivalent binding complex with respect to the binding domain (4) of the tagging agent (3).

As described, for example, in U.S. Pat. Nos. 7,776,562, 8,298,782, international application WO 2002/054065 or WO 2013/124474, this multivalent binding complex thus provides an avidity effect compared to the binding of the (monovalent) tagging agent alone, thereby allowing using low affinity monovalent tagging agents, which in single form would not stably bind the biological entity but would rapidly dissociate from the surface antigen. In the present invention, the avidity effect may be also important for the interaction of the tagging agent (3) with the recombinant antigen (2') of a linking molecule (10) as described herein. The so multimerized tagging agent (3) contained in this multivalent complexes can bind to the biological entity (1) or the linking molecule (10). In addition, due to the avidity effect, it is prudent to expect, that the method of the present invention is particularly useful for isolating cells having a low abundant surface antigen, such as CD34 or CD56.

Figure 13:
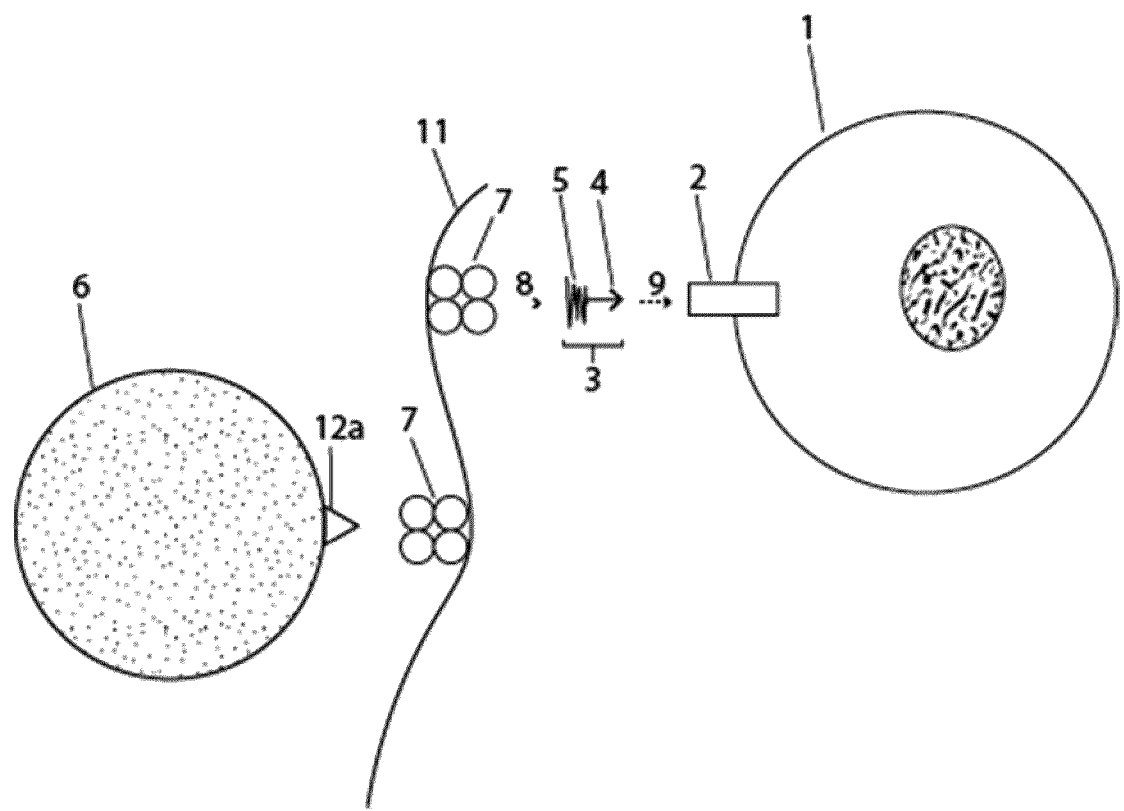
FIG. 13: Schematic representation of a method of isolating a biological entity, wherein the biological entity (1) indirectly binds a bead (6) via a carrier (11) forming an "antibody polymer". High molecular weight dextran as the carrier (11) can be chemically modified to bind many antibodies or Fab fragments (5) in active form. This antibody polymer can bind an antigen (2) present on biological entity but still has free binding sites for the further ligand (12a) bound to the surface of an agarose bead (6) and is therefore highly suitable for the isolation of biological entities. The principle depicted has been applied in Examples 9 and 10.

Alternatively, as depicted in FIG. 13, the soluble carrier (11) contains a plurality, i.e. at least two, ligand binding partners (7), which are capable of reversibly binding to the ligand (5) and to the further ligand (12a), or vice versa.

Accordingly, the tagging agent (3) binds its ligand (5) to a ligand binding partner (7) on the carrier (11) and the further ligand (12a) on the beads binds to a ligand binding partner (7) on the carrier. This method has the advantage that no linking molecule (10), i.e., the Strep-tagged recombinant antigen, is needed on the beads (6) but that the further ligand (12a) can be directly coupled to the beads. Thus, biotin agarose, a common and commercially available product, can be used. As explained with regard to FIG. 13, the carrier (11), i.e. the Strep-Tactin®/dextran polymer after binding to the biotin agarose (6) has still enough free binding sites to bind the ligand (5) of the tagging agent (3), i.e. the Strep-Tag of the Fab fragment, which can bind the antigen (2) of the biological entity (1) and can be eluted with a biotin solution.

This method is in particular useful for the isolation of exosomes and thus, in a preferred embodiment, the biological entity (1) is an exosome.

In one embodiment of the invention, the carrier (11) comprises the ligand binding partner (7) coupled thereto resulting in oligomerization or polymerization of the ligand binding partner (7). In a further embodiment, the ligand binding partner (7) coupled to the carrier (11) is streptavidin or avidin or of any analog of streptavidin or avidin. In one embodiment, the carrier (11) is a polysaccharide crosslinking the ligand binding partners (7) thereby forming an oligomer or polymer of the ligand binding partners (7). In one embodiment oligomers or polymers of streptavidin or of avidin or of analogs of streptavidin or of avidin are prepared by the introduction of carboxyl residues into a polysaccharide, e.g. dextran, essentially as described in Noguchi, A, et al., Bioconjugate Chemistry 3 (1992), 132-137 in a first step. Then streptavidin, avidin, or analogs thereof may be linked via primary amino groups of internal lysine residue and/or the free N-terminus to the carboxyl groups in the dextran backbone using conventional carbodiimide chemistry in a second step. Nevertheless, cross-linked oligomers or polymers of streptavidin or avidin or of any analog of streptavidin or avidin may also be obtained by crosslinking via bifunctional molecules, serving as a linker, such as glutardialdehyde or by other methods described in the art. The use of iminothiolan/SMCC, NHS activated carboxydextran or dendrimers are further examples of crosslinking techniques established in the art.

When using a streptavidin binding peptide as ligand (5) comprised in the tagging agent (3), the multimerized ligand binding partners (7) on the carrier (11) can be any streptavidin mutein, for example, any of the streptavidin muteins/analogues outlined, supra, e.g., a streptavidin mutein comprising the amino acid sequence Val44-Thr45-Ala46-Arg47 (SEQ ID NO: 13) at sequence positions 44-47 of wild type streptavidin or the streptavidin mutein (analog) Ile44-Gly45-Ala46-Arg47 (SEQ ID NO: 14) at sequence positions 44-47 of wild type streptavidin. Such muteins are described in U.S. Pat. No. 6,103,493, for example, and are commercially available in the form of mutein "m1" and mutein "m2" under the trademark Strep-Tactin®. Such multimeric streptavidin muteins may also be referred to as multimerized Strep-Tactin®. Another example for a carrier (11) with at least two ligand binding partners (7) bound thereto could be a streptavidin mutein as described herein coupled to complex branched glucan. In an exemplary embodiment, the streptavidin muteins available under the trademark "Strep-Tactin®" are coupled to a dextran (e.g. MW of 500,000 Da) using divinyl sulfone as coupling reagent to form the carrier (11) with the Strep-Tactin® coupled thereto.

In one embodiment, the coupling reaction is performed at a molar ratio of about 60 moles streptavidin or streptavidin mutein per mole of dextran. Other illustrative examples of oligomers or polymers of streptavidin, or a streptavidin mutein include the two kinds of a soluble oligomeric Strep-Tactin® mutein that act as soluble carrier and that are described in international application WO 2015/158868. The first kind of this oligomeric Strep-tactin® can be the fraction of the oligomeric streptavidin mutein (n≥3) described in Example 5 of WO 2015/158868. The second kind of such an oligomeric streptavidin mutein used as soluble carrier can be an oligomer that is obtained by reacting the soluble oligomeric streptavidin mutein with either biotinylated bovine serum albumin (BSA) or by crosslinking the soluble oligomeric streptavidin mutein with a soluble polyethylene glycol (PEG) molecule. These BSA or PEG based soluble carriers of the conventional Streptactin multimer also referred in WO 2015/158868 as "large Strep-Tactin® backbone"). Further illustrative examples of carriers are described in WO 2012/044999.

Dextrans are defined as branched poly-α-D-glucosides of microbial origin having glycosidic bonds predominantly C-1→C-6 (IUPAC. Compendium of Chemical Terminology, 2nd ed. (the "Gold Book"). Compiled by A. D. McNaught and A. Wilkinson. Blackwell Scientific Publications, Oxford (1997). Online version (2019-) created by S. J. Chalk). Accordingly, they are homopolysaccharides composed only with glucose residues linked at α(1-6) and with branches at α(1-3). There is a wide range of dextran varieties according to their molecular weight (from 3 to 3000 kDa) (Tabernero, A., et al. "Microbial exopolisaccharides for biomedical applications." Materials for Biomedical Engineering. Elsevier, 2019. 165-219). Due to the common solubility in water and various other solvents (e.g. DMSO, formamide), the biocompatibility, and the ability of degrading in certain physical environments, dextran is already successfully applied in the medical and biomedical field (Heinze et al. "Functional polymers based on dextran." Polysaccharides Ii. Springer, Berlin, Heidelberg, 2006. 199-291; DeBelder "Medical applications of dextran and its derivatives." In: Dimitriu S (ed) Polysaccharides in medicinal applications. Marcel Dekker, New York, 1996, p 505). As described by Heinze et al. (2006) the weight average molecular weight ($M_w$) of dextrans can be determined by light scattering, ultracentrifugation, small-angle neutron scattering and viscometry. Membrane osmometry and end group analysis give information about the number average molecular weight ($M_n$). Native dextran is generally of a high average molecular weight ranging from $9 \times 10^6$ to $5 \times 10^8$ g/mol with a high polydispersity. The polydispersity of dextran increases with the molecular weight as a result of increasing branch density. However, defined molecular weight fractions are of interest for many current applications. Beside the fractional precipitation with subsequent molecular weight determination, size exclusion chromatography (SEC) is a useful tool for analysis of the molecular weight distribution (MWD).

As indicated, supra, dextran polymers conjugated with a component capable of forming a non-covalent protein-ligand interaction, such as the ligand binding partner (7) of the method of the present invention, are useful in methods of isolating a biological entity in which they act as carrier molecules for the oligomerization/polymerization of the ligand binding partners (7). As shown in Example 7 and FIG. 9, the use of a carrier in the isolation method increases the yield of the target cells.

Therefore, in a further aspect, the present invention relates to a dextran polymer comprising at least two molecules of a covalently bound ligand binding partner (7), preferably a streptavidin or an analog or derivative thereof which is capable of binding a tagging agent (3), preferably comprising a streptavidin binding peptide. Alternatively, the present invention relates to a dextran polymer comprising at least two molecules of a covalently bound ligand binding partner (7), preferably a streptavidin or an analog or derivative thereof which is capable of binding a tagging agent (3), preferably comprising a streptavidin binding peptide and which is further capable of binding a further ligand (12a), which is preferably biotin. According to the invention, the dextran polymer has a molecular weight of about 500 kDa to 3,000 kDa, preferably about 1,000 kDa to 2,700 kDa, more preferably about 1,500 kDa to 2,500 kDa.

The components to be covalently bound to the dextran polymer, i.e. the ligand binding partner (7) as well as the tagging agent (3) binding to the ligand binding partner (7) and the further ligand (12a) binding to the ligand binding partner (7), respectively are described elsewhere herein. Examples of dextran polymers having a streptavidin derivative coupled thereto are described herein, supra and are within the scope of the present invention. Furthermore, chemical modifications of dextran including the synthesis of dextran derivatives and conjugates are reviewed in Heinze et al. (2006), supra, which is herein incorporated by reference in its entirety. Methods for preparing dextran polymers coupled with ligand binding partners are known in the art (Hermanson, G. T. Bioconjugate techniques. Elsevier; Rockford, Il: 2008. The chemistry of reactive groups; p. 188; Porath, J. (1974) General methods and coupling procedures. Meth. Enzymol. 34, 13-30). As described in WO 1993/001498 A1, dextran can be modified by divinyl sulfone (DVS) to which molecular species, such as the ligand binding partners comprised in the method of the present invention, in particular avidin or streptavidin analogues as defined herein can be covalently attached to; see, e.g., Example 31 in WO 1993/001498 A1.

In a further embodiment of the dextran polymer of the present invention, the dextran polymer is used in any of the methods of isolating a biological entity of the invention described herein as the carrier (11). A dextran polymer in accordance with the present invention has been used in a chromatographic method of the invention as described infra and in Example 6 and in a non-chromatographic method in Examples 7, 9 and 10 for the isolation of CD4+ cells, CD3+ cells and exosomes, respectively from human blood samples.

In accordance with the present invention, the dextran polymer can comprise different ligand binding partners (7), such as two, three, four or more enabling the purification of populations of biological entities via more than one surface antigen, such as populations of T cells defined by two or more CD receptors; see section "Surface antigen", supra. Therefore, the dextran polymer having at least two ligand binding partners (7) covalently attached thereto which thereby forms a ligand binding partner multimer, such as a dextran/Strep-Tactin® multimer represents a versatile tool as bi-, tri- or multivalent binding molecule that binds and immobilizes different tagging agents, such as Strep-tagged full antibodies, Fab fragments or nanobodies. Those can be used in stoichiometric mixtures to provide a dextran based macromolecule with different binding domains against different antigens.

However, instead of dextran based Strep-Tactin® multimers, Strep-Tactin® itself can be covalently linked forming multimers on which different tagging agents comprising e.g. a Strep-tag® and a binding domain can be immobilized via a non-covalent protein-ligand interaction as described, supra. Methods for linking Strep-Tactin® molecules are described in Hermanson, G. T. (2008) Bioconjucate techniques ($2^{nd}$ ed.), Elsevier.

Chromatographic Methods

In a further aspect, the present invention relates to chromatographic methods for isolating a biological entity comprising the above defined components. The principle underlying the method is schematically represented in FIG. 7, i.e. this principle and components depicted therein are not only suitable for isolating a biological entity via the above described non-chromatographic methods using freely movable beads but also via a chromatographic method, wherein, e.g., beads are packed as stationary phase or an equivalent stationary phase as defined below is used. Thus, the details as regards the biological entity (1), the antigen (2, 2'), the tagging agent (3), the binding domain (4), the ligand binding partner(s) (7), the ligand (5), the linking molecule (10), the carrier (11), the sample, the release of the biological entity (1), and the container as described above, do apply for the present method as well.

Accordingly, in this aspect of the invention, a method of isolating a biological entity is provided comprising providing
(i) a sample comprising the biological entity (1), wherein the biological entity (1) comprises a surface antigen (2);
(ii) a linking molecule (10) comprising an antigen (2') and a component for a non-covalent protein-ligand interaction, preferably wherein the component is a ligand (5);
(iii) at least two tagging agents (3) each comprising at least one binding domain (4) capable of specifically binding to the antigen (2) on the biological entity or to the antigen (2') comprised in the linking molecule (10);
(iv) a carrier (11) comprising at least two components for non-covalent protein-ligand interactions, preferably wherein the components are a ligand binding partner (7);
(vi) a stationary phase comprising a component capable of forming a protein-ligand interaction, preferably wherein the component is a ligand binding partner (7).

The sample, linking molecule (10), tagging agents (3), carrier (11) and stationary phase are then incubated within a container and a complex as indicated in FIG. 7 forms between the biological entity (1), the tagging agents (3), the linking molecule (10), the carrier (11) and the stationary phase, wherein the binding of the biological entity (1) via the tagging agent (3) to the carrier (11) and the binding of the linking molecule (10) to the carrier (11) and the stationary phase are mediated by non-covalent protein-ligand interactions (8). Complex formation results in immobilization of the biological entity (1) on the stationary phase. The biological entity (1) is purified by a chromatographic procedure and isolated by releasing the biological entity (1) from the carrier (11) and the tagging agent (3), respectively.

Figure 8:
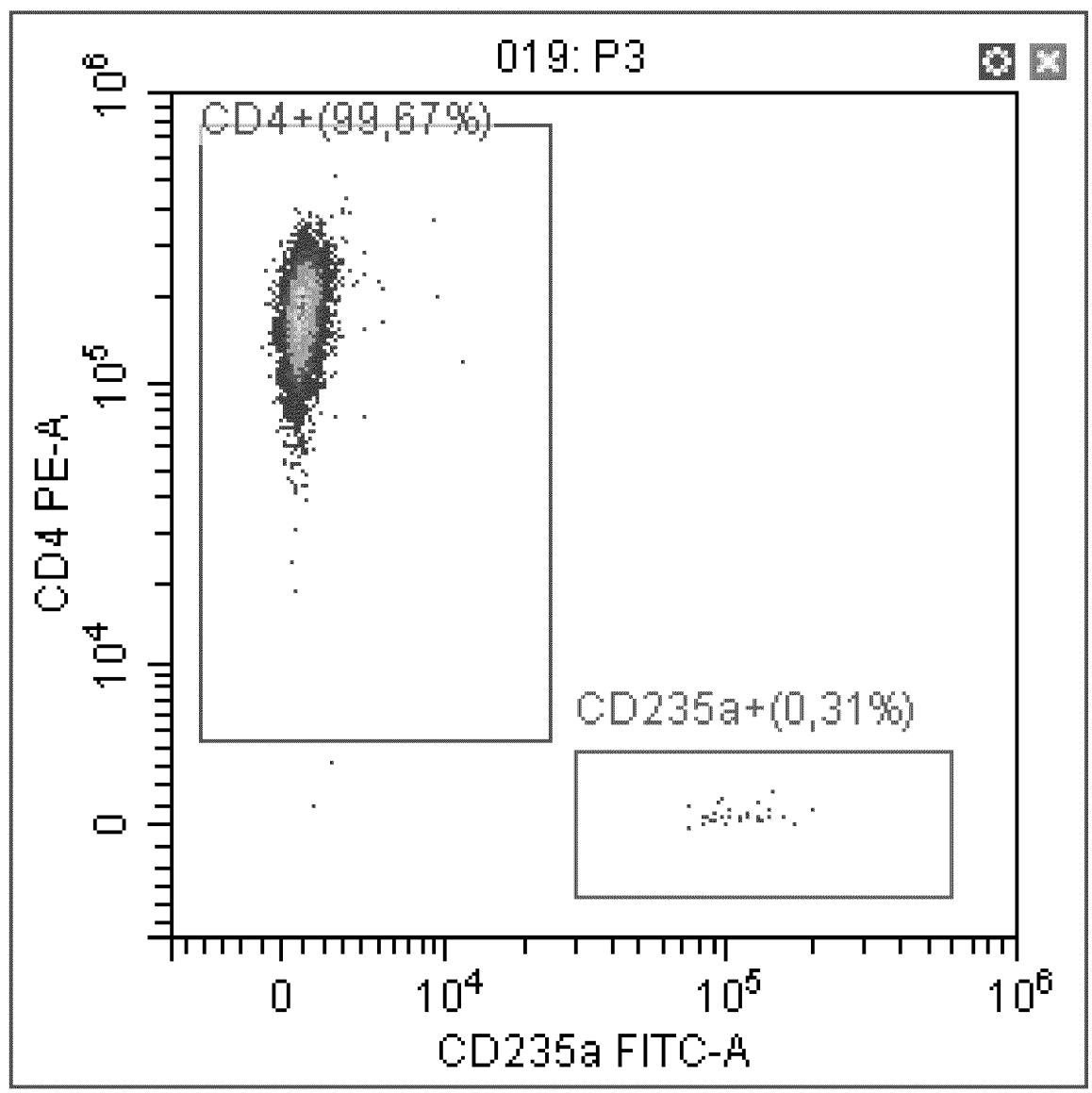
FIG. 8: FACS analyses of $CD4^+$ cells purified from buffy coat using the Strep-Tactin®/dextran polymer in a chromatographic method using the "standard mode" of the FABian® device results in pure CD4+ cells in good yields.

As described in Example 6, a dextran molecule used as a carrier inducing an avidity effect in an chromatographic method surprisingly results in highly efficient isolation of CD4+ cell; see FIG. 8.

Alternatively, to the above chromatographic method, the invention relates to a chromatographic method based on the components and principles schematically depicted in FIG. 10, i.e. this principle and components depicted therein are not only suitable for isolating a biological entity via the above described non-chromatographic methods using freely movable beads but also via a chromatographic method, wherein, e.g., beads are packed as stationary phase or an equivalent stationary phase as defined below is used.

Accordingly, in this aspect of the invention, a method of isolating a biological entity is provided comprising providing
- (i) a sample comprising the biological entity (1), wherein the biological entity (1) comprises a surface antigen (2);
- (ii) a linking molecule (10) comprising an antigen (2') and a component capable of forming a non-covalent protein-ligand interaction, preferably wherein the component is a ligand (5);
- (iii) a tagging agent (3') comprising two binding domains (4) capable of specifically binding to the antigen (2) on the biological entity and to the antigen (2') comprised in the linking molecule (10);
- (vi) a stationary phase comprising a component capable of forming the protein-ligand interaction, preferably wherein the component is a ligand binding partner (7).

The sample, linking molecule (10), tagging agent (3') and the beads (6) are incubated within a container and a complex as indicated in FIG. 10 forms between the biological entity (1), the tagging agent (3'), the linking molecule (10) and the beads (6), wherein the binding of the biological entity (1) via the tagging agent (3') and the linking molecule (10) to the stationary phase is mediated by the non-covalent protein-ligand interaction, wherein the biological entity (1) is immobilized on the stationary phase. The biological entity (1) is purified by a chromatographic procedure and/or isolated by releasing the biological entity (1) from the stationary phase and the tagging agent (3'), respectively.

The details as regards the biological entity (1), the antigen (2, 2'), the tagging agent (3), the binding domains (4), the ligand binding partner (7), the ligand (5), the linking molecule (10), the sample, the release of the biological entity (1), and the container as described above, do apply for the present method as well. In the Figures schematically representing the corresponding methods, i.e. FIGS. 7 and 10, the beads (6) of the non-chromatographic method are equivalent to the stationary phase of the chromatographic methods.

In both chromatographic methods, the chromatography can be carried out in a flow through mode in which a fluid sample containing the biological entity to be isolated is applied, for example, by gravity flow or by a pump on one end of a column containing the chromatography matrix, e.g., beads packed as stationary phase, and in which the fluid sample exits the column at the other end of the column. In addition, the chromatography can be carried out in an "up and down" mode in which a fluid sample containing the cells to be isolated is applied, for example, by a pipette on one end of a column containing the chromatography matrix packed within a pipette tip and in which the fluid sample enters and exits the chromatography matrix/pipette tip at the other end of the column.

Any material may be employed as stationary phase in the context of the invention, as long as the material is suitable for the chromatographic isolation of cells. A suitable chromatography material is at least essentially innocuous, i.e. not detrimental to cell viability (or the viability or stability of the biological entity), when used in a packed chromatography column under desired conditions for cell isolation and/or cell separation. A chromatography matrix as used in the present invention remains in a predefined location, typically in a predefined position, whereas the location of the sample to be separated and of components included therein, is being altered. Thus, the "stationary phase" in the context of the chromatographic methods of the invention is the part of a chromatographic system through which the mobile phase flows and where distribution of the components contained in the liquid phase (either dissolved or dispersed) between the phases occurs.

Typically, the respective stationary phase or chromatography matrix has the form of a solid or semi-solid phase, whereas the sample that contains the biological entity to be isolated/separated is a fluid phase. The mobile phase used to achieve chromatographic separation is likewise a fluid phase. The chromatography matrix can be any particulate material (of any suitable size and shape) or a monolithic chromatography material, including a paper substrate or membrane. Thus, the chromatography can be both column chromatography as well as planar chromatography. In addition to standard chromatography columns, columns allowing a bidirectional flow such as PhyTip® columns available from PhyNexus, Inc., San Jose, CA, U.S.A. or pipette tips can be used for column based/flow through mode based chromatographic separation of cells as described here. Thus, pipette tips or columns allowing a bidirectional flow are also encompassed by the term "chromatography columns" as used herein. If a particulate matrix material is used, the particulate matrix material may be a mixture of particles having a mean particle size of about 5 μm to about 200 μm, or from about 5 μm to about 400 μm, or from about 5 μm to about 600 μm. As explained in detail in the following, the chromatography matrix may, for example, be or include a polymeric resin, a metal oxide, or a metalloid oxide. If planar chromatography is used, the matrix material may be any material suitable for planar chromatography, such as conventional cellulose-based or organic polymer based membranes (for example, a paper membrane, a nitrocellulose membrane or a polyvinylidene difluoride (PVDF) membrane) or silica coated glass plates. In one embodiment, the chromatography matrix/stationary phase is a non-magnetic material or non-magnetizable material.

Non-magnetic or non-magnetizable chromatography stationary phases that are used in the art, and that are suitable in the present invention, include derivatized silica or a crosslinked gel. A crosslinked gel (which is typically manufactured in a bead form) may be based on a natural polymer, i.e. on a polymer class that occurs in nature. For example, a natural polymer on which a chromatography stationary phase is based is a polysaccharide. A respective polysaccharide is generally crosslinked. An example of a polysaccharide matrix is an agarose gel (for example, Superflow™ agarose or a Sepharose® material such as Superflow™ Sepharose® that are commercially available in different bead and pore sizes) or a gel of crosslinked dextran(s). A further illustrative example is a particulate cross-linked agarose matrix, to which dextran is covalently bonded, that is commercially available (in various bead sizes and with various pore sizes) as Sephadex® or Superdex®, both available from GE Healthcare. Another illustrative example of such a chromatography material is Sephacryl® that is also available in different bead and pore sizes from GE Healthcare.

A crosslinked gel may also be based on a synthetic polymer, i.e. on a polymer class that does not occur in nature. Usually such a synthetic polymer on which a chromatography stationary phase for cell separation is based is a polymer that has polar monomer units, and which is therefore in itself polar. Such a polar polymer is hydrophilic. Hydrophilic molecules, also termed lipophobic, contain moieties that can form dipole-dipole interactions with water molecules. Hydrophobic molecules, also termed lipophilic, have a tendency to separate from water.

Illustrative examples of suitable synthetic polymers are polyacrylamide(s), a styrene-divinylbenzene gel and a copolymer of an acrylate and a diol or of an acrylamide and a diol. An illustrative example is a polymethacrylate gel, commercially available as a Fractogel®. A further example is a copolymer of ethylene glycol and methacrylate, commercially available as a Toyopearl®. In some embodiments a chromatography matrix may also include natural and synthetic polymer components, such as a composite matrix or a composite or a co-polymer of a polysaccharide and agarose, e.g. a polyacrylamide/agarose composite, or of a polysaccharide and N,N'-methylenebisacrylamide. An illustrative example of a copolymer of a dextran and N,N'-methylenebisacrylamide is the above-mentioned Sephacryl® series of material. Derivatized silica may include silica particles that are coupled to a synthetic or to a natural polymer. Examples of such embodiments include, but are not limited to, polysaccharide grafted silica, polyvinylpyrrolidone grafted silica, polyethylene oxide grafted silica, poly(2-hydroxyethylaspartamide) silica and poly(N-isopropylacrylamide) grafted silica.

A chromatography matrix employed in the present invention is in some embodiments a gel filtration (also known as size exclusion) matrix. A gel filtration can be characterized by the property that it is designed to undergo, at least essentially, no interaction with the cells to be separated. Hence, a gel filtration matrix allows the separation of cells or other biological entities as defined herein largely based on their size. A respective chromatography matrix is typically a particulate porous material as mentioned above. The chromatography matrix may have a certain exclusion limit, which is typically defined in terms of a molecular weight above which molecules are entirely excluded from entering the pores. The respective molecular weight defining the size exclusion limit may be selected to be below the weight corresponding to the weight of a biological entity to be isolated. In such an embodiment, the biological entity is prevented from entering the pores of the size exclusion chromatography matrix. Likewise, a stationary phase that is an affinity chromatography matrix may have pores that are of a size that is smaller than the size of a chosen biological entity. In illustrative embodiments the affinity chromatography matrix and/or the gel filtration matrix has a mean pore size of 0 to about 500 nm.

Other components present in the method such as tagging agents (3), linking molecules (10), carriers (11) or a competing reagent may have a size that is below the exclusion limit of the pores and this can enter the pores of the size exclusion chromatography matrix. Of such components that are able to partially or fully enter the pore volume, larger molecules, with less access to the pore volume will usually elute first, whereas the smallest molecules elute last. In some embodiments, the exclusion limit of the size exclusion chromatography matrix is selected to be below the maximal width of the biological entity. Hence, components that have access to the pore volume will usually remain longer in/on the size exclusion chromatography matrix than the biological entity. Thus, the biological entities can be collected in the eluate of a chromatography column separately from other matter/components of a sample. Therefore components such as a tagging agent (3), a carrier (11) or a linking molecule (10), or where applicable, a competing reagent, elute at a later point of time from a gel filtration matrix than the biological entity.

Figure 5:
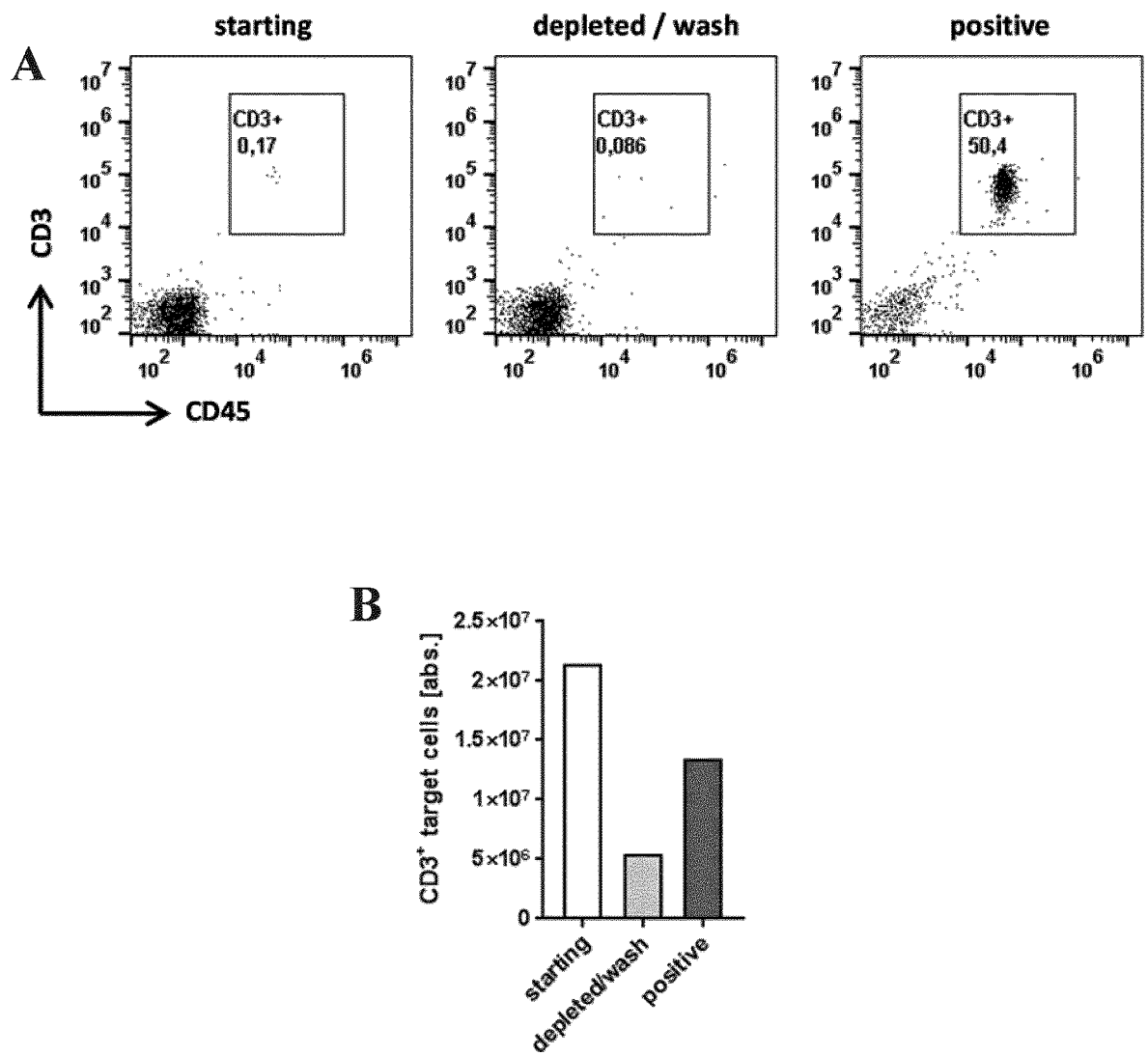
FIG. 5: FACS analyses of $CD3^+$ cells enriched from buffy coat using a chromatographic method in the semiautomated FABian® device in "standard mode" with agarose beads having a diameter of 90 µm (+/−50 µm) as shown in dot plot (A) and bar chart (B) in the indicated fractions. The "standard mode" program of the FABian® device is provided in (C) with a pipetting/filling scheme (D, lower panel) corresponding to the positions of the FABian® device (upper panel). The sample velocity was 0.48 ml/min for uptake and 0.39 ml/min for release.
Figure 5:
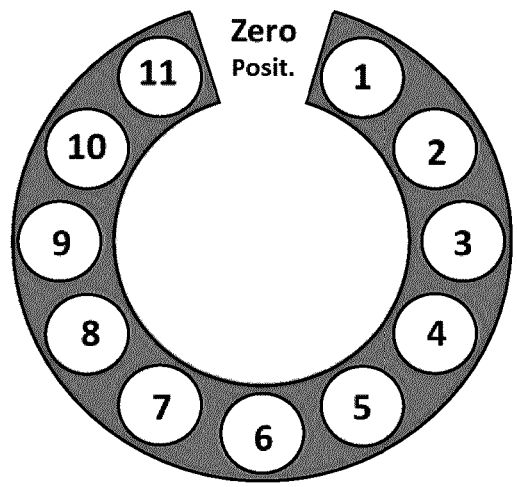

A chromatographic method of the present invention can be performed using an apparatus such as the FABian® device operated in the "standard mode" which does not allow for continuous floating of the beads within the sample due to the low sample uptake and release velocities as compared to the "moving batch mode"; see Example 4 and 6, and FIGS. 5 and 8.

Kits

The present invention also relates to kits, for instance, designed for performing a method as detailed above. The kit may include at least one tagging agent (3, 3'), beads (6), a carrier (11), linking molecule (10), further ligand (12/12a), further ligand binding partner (13), washing buffer and/or competing agent as defined herein. For example, the beads (6) comprised within the kit can have the ligand binding partner (7) immobilized thereon. The kit may for example include a container filled with the tagging agent (3, 3'), e.g. in solution. For the chromatographic methods of the invention, the kit may also include a stationary phase as described herein, which may be (pre)packed into a column, such as a cartridge. Associated with such stationary phase and/or container(s) there is in some embodiments provided a notice in the form of instructions on how to use the kit to carry out a method according to the present invention.

Apparatus

In a further aspect, the present invention relates to an apparatus for performing any of the above described methods of the invention, wherein the apparatus comprises an arrangement designed to perform a method of isolating a biological entity of the invention. In particular, the apparatus comprises holders for the container, receptacles for the supply and reception of liquids, a device for supplying and receiving liquids from the receptacle to the container, configured to enable floating beads (6) up and down within a liquid present in the container as well as means for soaking, pumping and draining a liquid through one opening of the container and discharging the liquid while the beads (6) are hold in place.

An exemplary apparatus of the invention is the FABian® device provided by Cell.Copedia GmbH or in case of the "moving bach method" peristaltic pumps. The FABian® device is described in detail in WO 2016/092025 A1 which is herein incorporated by reference in its entirety. In particular, the apparatus comprises a syringe housing comprising inter alia a syringe body having a syringe body attachment reversibly attached thereto, wherein the syringe body performs a pipetting process for taking up and releasing a liquid to/from the syringe body attachment. Thereby, the beads for the non-chromatographic methods and the stationary phase for the chromatographic methods, respectively are added to the syringe body attachment first, wherein the syringe body attachment comprises a membrane at the bottom edge which prevents the beads to leave the syringe body attachment. In particular, the syringe body attachment for the chromatographic methods comprises another membrane on top of the stationary phase which prevents the stationary phase from floating within the column. Therefore, usually the stationary phase is prepacked within the syringe body attachment. For the chromatographic methods of the invention, the FABian® device can be operated in one of the standard programs available under: https://www.iba-life-sciences.com/download-area-cell.html. In the standard mode, the beads do not continuously float within the sample, and therefore represent a conventional chromatographic method, wherein the sample as the mobile phase passes through the beads as stationary phase. In Example 6, the FABian® device has been used in the "standard mode" (as depicted in FIG. 5C) in order to purify $CD4^+$ cells from human blood using a dextran antibody polymer.

Figure 6:
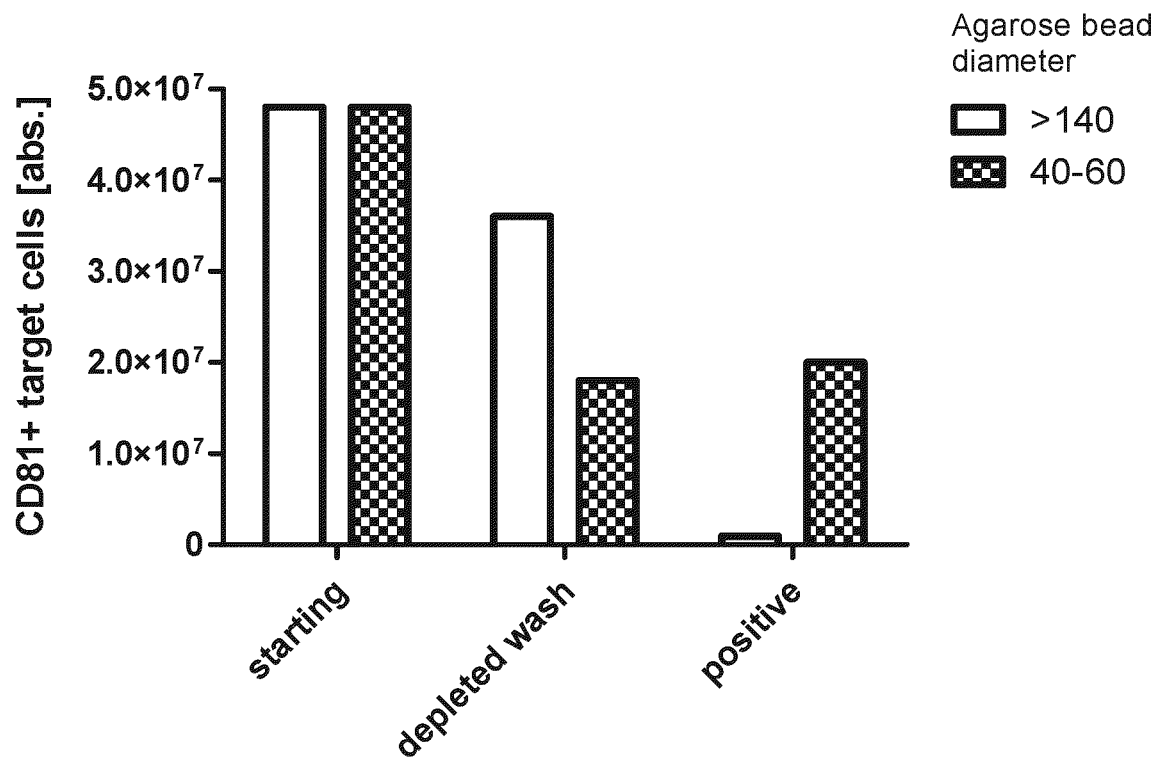
FIG. 6: FACS analyses of CD81V cells purified from buffy coat using a non-chromatographic method in the semiautomated FABian® device with agarose beads having a diameter of about 40-60 µm (small beads) and >140 µm (large beads), respectively, in the cell isolation fractions indicated (A). The detailed program "moving batch mode" of the FABian® device is provided in (B) with a pipetting/filling scheme (C, lower panel) corresponding to the positions of the FABian® device (upper panel). The flow rates and sample velocity were significantly increased in comparison to the "standard mode" reaching 1.84 ml/min for uptake and sample 0.74 ml/min for release (1.59 ml/min for last release).
Figure 6:
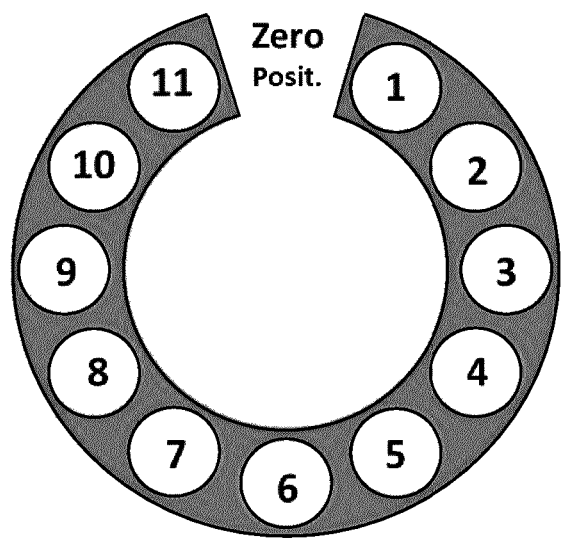
Figure 12:
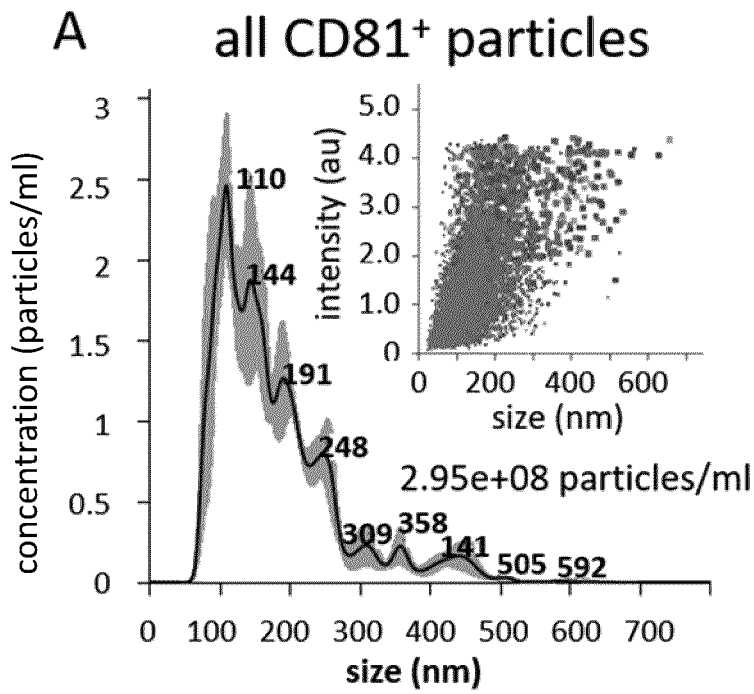
FIG. 12: Analysis of extracellular vesicles including exosomes purified via a Strep-Tactin®/dextran polymer using the "moving batch mode" of the FABian® device. Nanoparticle tracking analysis (NTA) was used to determine size distribution, concentration and absorption intensities of particles. Particles from human buffy coat (A) were immuno-affinity purified with Fab against the tetraspanin CD81. Data of 5 technical NTA replicates reveal a size distribution from 80 to about 500 nm with a majority of particles in the range of 100 to 200 nm (B). Particles in (B) were further processed by size exclusion chromatography with a selective range of 30 to 200 nm to remove Fab, biotin and particles >200 nm. The resulting size distribution of particles in the column's void volume ranges from 60 to <300 nm with the vast majority of events between 80 and 150 nm, representing the approximate size of exosomes. In order to exclude possible impurities from particles in the PBS that was used during the assay, NTA of buffer was performed as negative control (C). The isolated particles have been further analyzed by Immunoblot revealing the identity of purified particles as exosomes (D).
Figure 12:
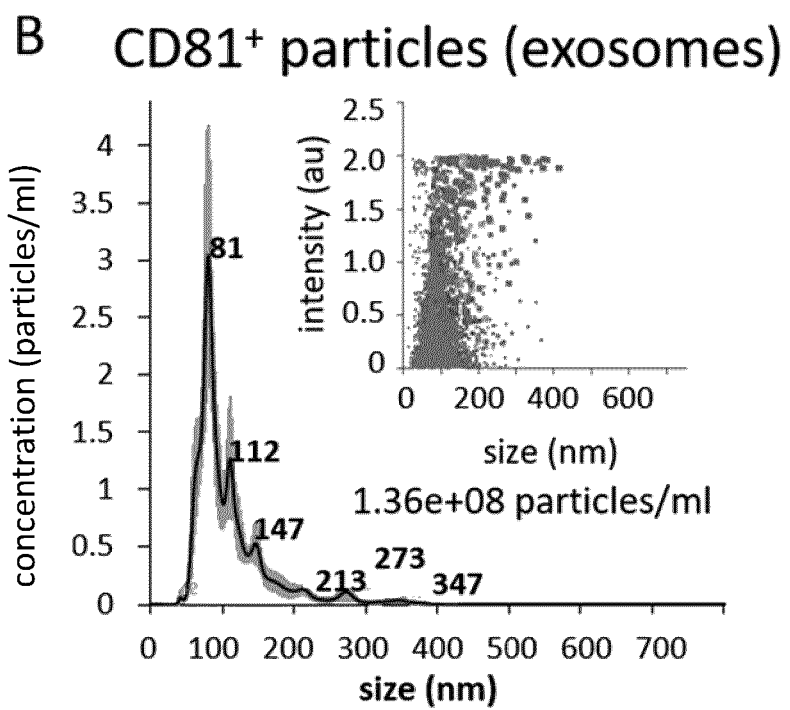
Figure 12:
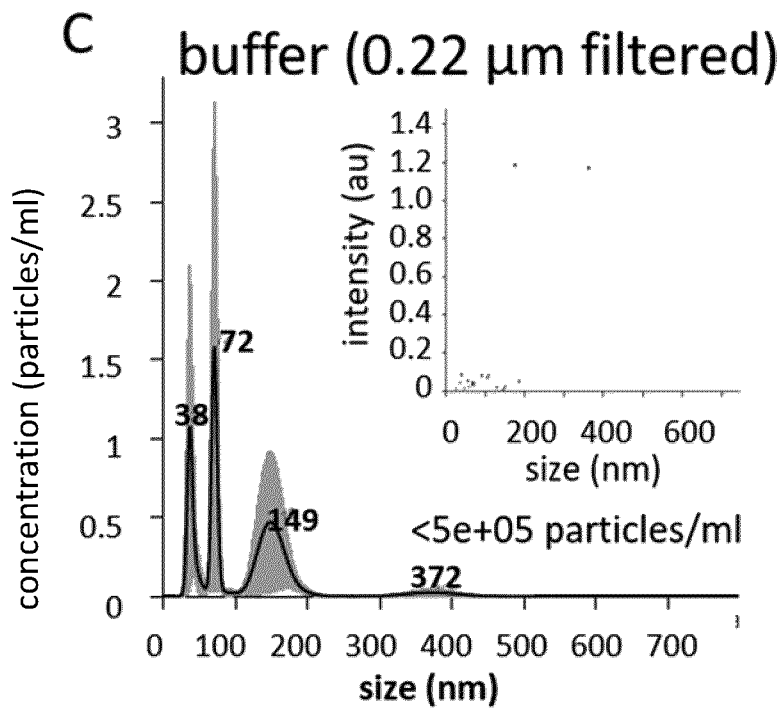
Figure 12:
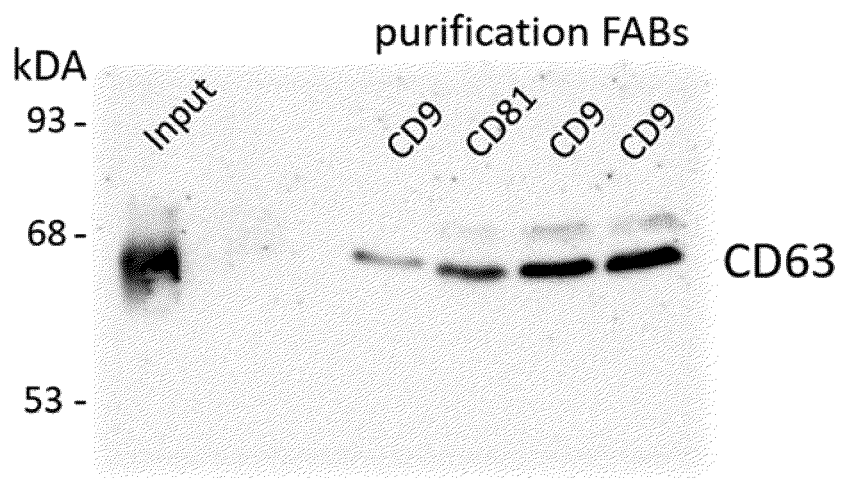

For the non-chromatographic methods disclosed herein, a novel program has been developed which is referred to as the "moving batch mode" in which essentially the velocity of the sample uptake and release have been increased from 0.48 ml/min for the uptake and 0.39 ml/min for the release in the standard mode to 1.84 ml/min for the uptake and 0.74 ml/min for the release (1.59 ml/min for fast release) in the moving batch mode; compare FIG. 5C for the standard mode and FIG. 6B for the moving batch mode. Furthermore, for the "moving batch mode", the apparatus disclosed in WO 2016/092025 A1 has been modified in that only one membrane is present at the bottom of the syringe body attachment whereas the other membrane on top of the beads is absent in order to enable the beads to be freely movable. The moving batch mode of the FABian® device has been exemplary shown to be suitable for the method of isolating a biological entity in accordance with the present invention in Examples 5-8, wherein target cells such as $CD81^+$ and $CD4^+$ as well as exosomes have efficiently been isolated in high purity; see FIGS. 6, 9 and 12. Advantageously, using the FABian® device exosomes can rapidly be isolated within half of the time compared to the time of the complete program necessary for larger biological entities, such as cells.

The above disclosure generally describes the present invention. Several documents are cited throughout the text of this specification, the contents of all of which (including literature references, issued patents, published patent applications as cited throughout this application, including the disclosure in the background section and manufacturer's specifications, instructions, etc.) are hereby expressly incorporated by reference; however, there is no admission that any document cited is indeed prior art as to the present invention.

A more complete understanding can be obtained by reference to the following specific examples which are provided herein for purposes of illustration only and are not intended to limit the scope of the invention.

EXAMPLES

Example 1: Agarose Bead Preparation

Commercially available beads for cell isolation such as agarose beads from IBA GmbH are a mixture of beads with varying diameters between about 30 µm to about 180 µm with a maximum between 80 and 120 µm (FIG. 1). In order to obtain specific fractions of agarose beads, the commercially available agarose beads were sieved through appropriate nylon meshes. For example, bead fractions between 40-60 µm ("small beads") and 140-180 µm ("large beads") were used for the following experiments performed in accordance with the present invention.

Example 2: Conventional Cell Chromatography Using Different Agarose Bead Fractions In order to assess the influence of the particle diameter on the outcome of hitherto conventionally applied cell isolation procedures, immunoaffinity chromatography (IAC) was applied to agarose bead fractions of different sizes. Agarose beads (cell grade, IBA GmbH, Göttingen, Germany) were used in standard size (about 80-120 µm) and small or large fractions as described in Example 1. Plastic columns with a frit at the bottom (IBA GmbH, Göttingen, Germany) were filled with 0.5 ml agarose coated with Strep-Tactin® and Fab against CD81. 5 ml human blood diluted 1:1 with buffer CI (PBS, 1 mM EDTA, 0.5% BSA) and filtered through a 40 µm nylon sieve was applied to the columns at the same time. As can be seen from FIG. 2, small size beads (left column) do not allow for flow through the chromatography column since the binding cells block the flow through the column. Standard size beads (middle column) allow chromatography with retarded speed, whereas the large size beads (right column) allow rapid passage of the blood without delay. Using standard size beads $CD81^+$ cells could be isolated, whereas using large beads essentially no $CD81^+$ cells could be isolated from the beads after eluting the columns with buffer CI containing 1 mM biotin.

Example 3: Enrichment of $CD3^+$ Cells from Human PBMCs $CD3^+$ cells were non-chromatographically isolated from human PBMCs in a reagent tube with antibody coated agarose beads. In particular, 0.5 ml of Strep-Tactin® coated agarose beads (IBA GmbH, Göttingen, Germany) with a bead diameter of about 40-60 µm, i.e. "small beads" as previously mentioned were mixed with 22.5 µg anti-human CD3 Strep-tagged Fab fragments (IBA GmbH, Göttingen, Germany) in a 30 ml tube (Sarstedt AG & Co. KG, Nurnbrecht, Germany) and incubated for 5 min on a rocking table shaker (Unitwist RT, UniEquip Laborgerätebau-und Vertriebs GmbH, Planegg, Germany) at the lowest possible speed (100 shakes per min). After letting the beads settle by gravity, the supernatant was removed by pipetting and discarded. 1 ml of PBMCs (1.57×107 cells) was added to the CD3-Fab/agarose beads and incubated for 5 min on the shaker at the lowest possible speed. After letting the beads settle for 2 min, the supernatant was collected as depleted fraction. Beads were washed 3 times with 5 ml Washing Buffer (CI buffer: PBS, 0.5% BSA, 1 mM EDTA) and the supernatant was collected as wash fraction. Cell elution was performed using two times 5 ml of 1 mM biotin in CI buffer (IBA GmbH, Göttingen Germany). Beads were incubated for 5 min under shaking during biotin incubation and the supernatant was collected as positive fraction. Thereby, supernatants were removed using a "pipette man" and a 10 or 5 ml pipette or a 1 ml pipette tip, that have a nylon sieve with 30 µm pore size glued to the top of the tip to keep remaining unsettled beads away. FACS analysis was carried out using a CyAnTM ADP flow cytometer (Beckman Coulter, Brea, California, USA) after staining with CD3-PeCy7 and CD45-eFluor 450 antibodies (both from eBioscience, Inc., San Diego, California, USA).

Figure 4:
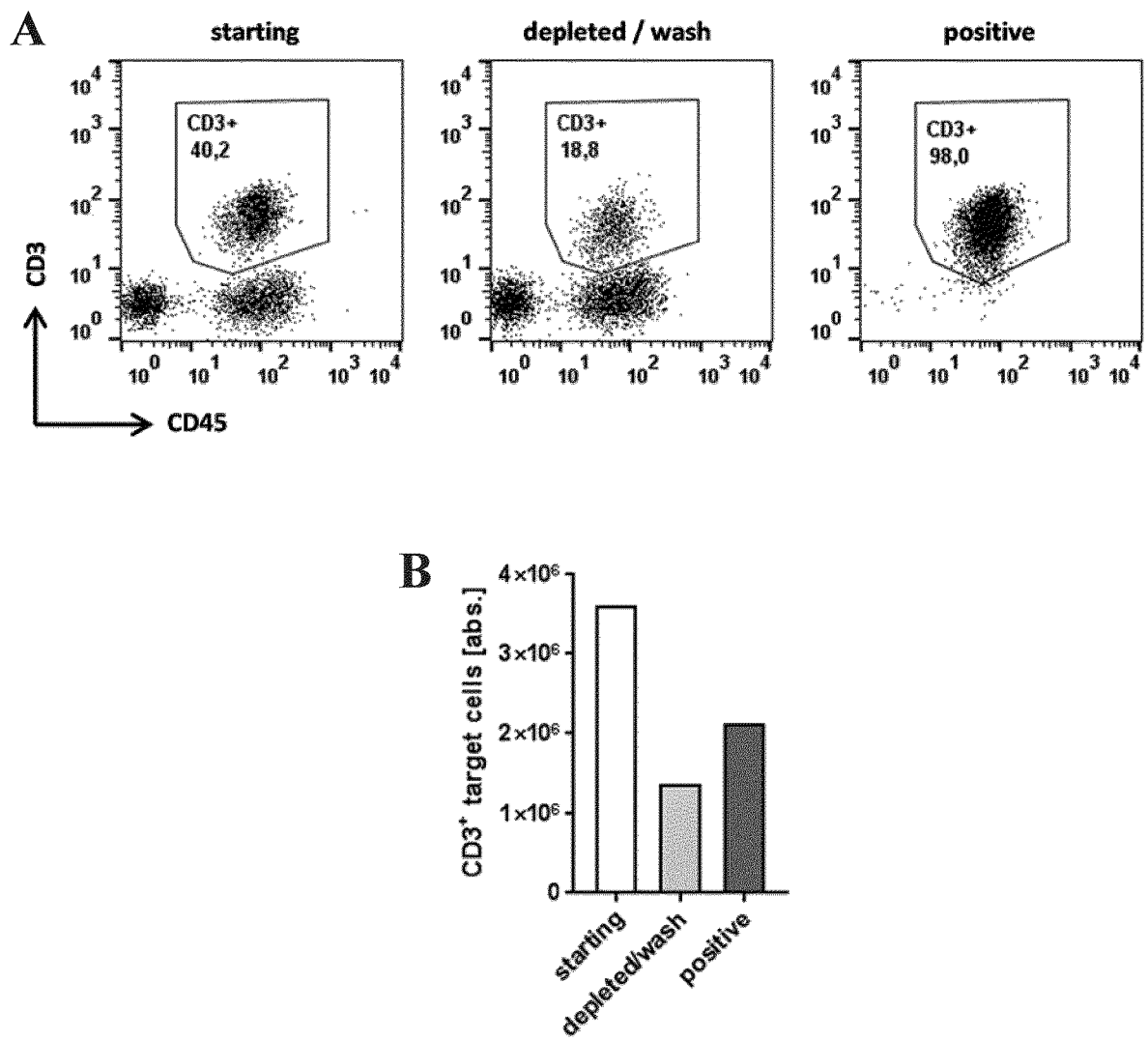
FIG. 4: FACS analyses of $CD3^+$ cells enriched from human PBMCs following non-chromatographic cell isolation using agarose beads with a diameter between about 40-60 µm, wherein the beads are kept in continuous motion in a reagent tube as shown in dot plot (A) and bar chart (B) in the indicated fractions.

The enrichment of $CD3^+$ cells is shown in FIG. 4 in dot plot (A) and bar chart (B) of the starting fraction, depleted/wash fraction and positive fraction. Enrichments were performed with purities of up to 98% and yields of up to 59%. As shown, this procedure leads to cells in the supernatant in high purity and yields.

In this experiment which corresponds to the schematic representation depicted in FIG. 3, the biological entity (1) is a $CD3^+$ cell, i.e. the antigen (2) is CD3. The tagging agent (3) is an anti-human CD3 Strep-tagged Fab fragment, wherein the binding domain (4) is a CD3 Fab fragment and the ligand (5) being part of the protein-ligand-interaction is a Strep-tag. The beads (6) are coated with the ligand binding partner (7) which is Strep-Tactin®.

Example 4: Enrichment of $CD3^+$ Cells from Buffy Coat in the Semiautomated Device FABian® in the "Standard Mode"

In order to show that the procedure schematically visualized in FIG. 3 performed as a chromatographic method is not optimal for purifying biological entities, essentially the same components for isolating CD3+ cells as described in Example 3 were used and applied to the FABian® device (Cell.Copedia GmbH, Leipzig Germany). In particular, CD3+ cells were isolated from buffy coat using the FABian® device in the "standard mode", i.e. in a chromatographic method according to the manufacturer's instructions for use (program A) as provided in FIG. 5C-D with 0.5 ml of Strep-Tactin® coated agarose beads (IBA GmbH, Göttingen Germany) with a bead diameter of 90 μm (+/−50 μm). Thereby, the "standard mode" The FABian® instrument was prepared as follows: position 1: 22.5 μg anti-human CD3 Strep-tagged Fab fragments (IBA GmbH) in 4.2 ml washing buffer (IBA GmbH, Göttingen Germany), position 2: 4.25 ml of buffy coat (diluted in a ratio of 1:1 with washing buffer), positions 3, 4 and 10 with an empty tube, positions 5, 6, 7 and 8 with 9 ml, 6 ml, 9 ml and 2 ml washing buffer, respectively and positions 9 and 11 with 6 ml 1 mM biotin solution. FABian® program A was used. FACS analysis was carried out using a CytoFLEX flow cytometer (Beckman Coulter, Brea, California, USA) with CD3-APC and CD45-PerCP/Cy5.5 antibodies (both from BioLegend, San Diego, California, USA). Enrichment of CD3+ cells is shown in FIG. 5 as dot plot (A) and bar chart (B) of the depicted fractions. The experiment was performed with a purity of up to 51% and a yield of up to 63%.

The data depicted in FIG. 5 indicate that the use of the FABian® device in the "standard mode" does not provide optimal conditions for isolation of a biological entity from a blood sample. As shown in the following Examples, purity and yields may be improved by switching from the "standard mode" to a "moving batch mode" of the FABian® device including the use of smaller beads.

Example 5: Purification of CD81+ Cells from Buffy Coat Using the Semiautomated FABian® Device with Small and Large Beads As described above, in Example 4 the conditions for T cell purification using the FABian® device needed adaptation resulting in establishing the "moving batch mode" of the FABian® device. The moving batch process is achieved in the FABian® device by sucking up and down buffers and blood at new optimized selected speeds as described in detail below, which keep beads in continuous motion. Agarose beads having a diameter of 40-60 μm and 140-200 μm have been used. Both fractions were obtained by sieving of standard IBA GmbH Strep-Tactin® coated beads; see Example 1. The FABian® instrument was used in its standard configuration except that a program with different time intervals and flow through speeds was used which is termed the "moving batch mode" (see FIG. 6B-C).

Strep-Tactin® coated agarose beads (0.5 ml) were initially incubated 5 min with 22.5 μg of CD81 Strep-tagged Fab fragments (IBA GmbH, Göttingen, Germany), then washed with buffer CI (5% BSA in PBS pH 7.4, 1 mM EDTA) to remove unbound Fab. Then beads were incubated under continuous sucking up and down intervals with 4.5 ml buffy coat diluted 1:1 in buffer for 15 min. This was followed by 3 wash cycles using 5 ml buffer each removing unbound cells. Bound cells were then incubated for 5 min in buffer CI containing 1 mm biotin. FACS analysis was carried out as described in Example 4, supra, with markers corresponding to CD81.

FIG. 6 shows that the use of small beads in the context of the "moving batch mode" of the FABian® device results in efficient T cell purification from blood with high yields and purity and while large beads with a diameter above 140 μm show almost negligible yields confirming that the use of large beads as present in commercially available agarose beads should be avoided because they do not bind cells, i.e. the yield is only marginally and may stem from smaller beads left over in the fraction by incomplete sieving.

In this experiment which corresponds to the schematic representation depicted in FIG. 3, the biological entity (1) is a CD81+ cell, i.e. the antigen (2) is CD81. The tagging agent (3) is an anti-human CD81 Strep-tagged Fab fragment, wherein the binding domain (4) is a CD81 Fab fragment and the ligand (5) being part of the protein-ligand-interaction is a Strep-tag. The beads (6) are coated with the ligand binding partner (7) being part of the protein-ligand-interaction which is Strep-Tactin®.

Example 6: Purification of CD4+ Cells from Human Blood Using a Dextran Antibody Polymer Strep-Tactin®/dextran polymers were obtained by coupling dextran (MW 500.000 Da) to Strep-Tactin® (IBA GmbH) with divinylsulfone using standard methods (Hermanson, G. T. (2008) Bioconjugate techniques ($2^{nd}$ ed.), Elsevier) which were incubated with the CD4 binding Fab fragment contained in the CD4 Fab Streptamer Isolation Kit MB, human of IBA GmbH (catalogue no: 6-8000-206) for 5 min. Unbound Fab fragments were removed by gel chromatography. Surprisingly, the Strep-Tactin®/dextran polymer coated with Fab fragment has enough free antibodies not involved in antigen binding present on the bead surface which are available for binding of the biological entity. Column chromatography was carried out using the FABian® device with prepacked 1 ml agarose columns (IBA GmbH) preincubated with 45 μg of the extracellular domain of the CD4 protein fused to the streptavidin binding peptide known as Twin Strep-Tag®. This fusion protein was recombinantly produced in E. coli and purified using standard methods. The FABian® program was then started as described in the IBA FABian® manual except that instead of Fab fragments 100 μg (related to Strep-Tactin® content) Strep-Tactin®/dextran polymer coated with Fab fragment were loaded to the column. In the next step 6 ml of human blood in the form of buffy coat diluted 1:1 with CI buffer was chromatographed on the column and unbound cells were washed away with FACS buffer as described in the manual. CD4+ cells were then obtained after elution with CT buffer containing 1 mM biotin as described in the manual. FACS analysis was carried out using a Cytoflex FACS machine (Beckton & Dickinson, USA) with PE/CD4 antibody staining and anti CD235 staining.

As can be seen in FIG. 8, the biotin elution released extremely pure CD4+ cells in high yields. CD235+ erythrocytes are almost absent.

In this experiment which corresponds to the schematic representation depicted in FIG. 7, the biological entity (1) is a CD4+ cell, i.e. the antigen (2) is CD4. The procedure comprises a carrier (11) which is high molecular weight dextran having at least two ligand binding partners (7), i.e. Strep-Tactin® covalently coupled thereto. The tagging agents (3) are anti-human CD4 Strep-tagged Fab fragments, wherein the binding domains (4) are CD4 Fab fragments and the ligands (5) being part of the protein-ligand-interaction are Strep-tags. At least two of those tagging agents (3) are immobilized on the Strep-Tactin®/dextran carrier (10-7) via a non-covalent protein-ligand interaction (8) between the Strep-tag (5) and the Strep-Tactin® (7). One of the at least two tagging agents (3) binds the CD4 antigen (2) on the biological entity and the other tagging agents (3) binds a linking molecule (10) via an antigen recognition interaction (9). The linking molecule (10) is a CD4-Twin-Strep-tag® fusion protein consisting of the antigen (2') which is the recombinantly expressed extracellular domain of the CD4 protein and the ligand (5) being part of the non-covalent protein-ligand-interaction which is a Twin-Strep-tag®. The beads (6) are coated with the ligand binding partner (7), i.e. Strep-Tactin® which is bound by the ligand (5), i.e. Twin-Strep-tag® of the linking molecule (10).

Example 7: Enrichment of CD4+ Cells from Human PBMCs and Human Whole Blood Using the Strep-Tactin®/Dextran Polymer Combined with the Moving Batch Mode As a further development of the method described in Examples 5 and 6, the use of the Strep-Tactin®/dextran polymer in the "moving batch mode" was analyzed, wherein essentially the same components for isolating CD4+ cell were used as described in Example 6. In particular, for the purification of CD4+ cells from human PBMCs and whole blood standard agarose beads with 90 µm average diameter (+/−50 µm) were used. Therefore, 200 µg Strep-Tactin®/dextran polymers and 200 µg anti-human CD4 Strep-tagged Fab fragments (IBA GmbH) were added to 1 ml Strep-Tactin® coated agarose beads (preincubated with human CD4 antigen, i.e. Strep-tagged CD4 antigen) in a 15 ml column (Biocomma, China) with a 90 µm frit at the bottom. The reference isolation without dextran polymer was performed according to the standard method with Fab-loaded Strep-Tactin® beads (see IBA GmbH cell isolation by gravity columns): 45 µg anti-human CD4 Strep-tagged Fab fragment were added to 1 ml Strep-Tactin® coated agarose beads. Afterwards, 5 ml of PBMCs (2.48×10$^7$ cells) and 10 ml whole blood, respectively, were added to the column and incubated for 10 min under rotation at the lowest speed (one revolution per second; tumbling roller mixer, RM5, A. Hartenstein) by putting an upper and bottom cap on the column. After removing the top cap and the cap at the outlet of the column, unbound cells were drained via gravity. The beads were washed two times with 10 ml washing buffer (IBA GmbH, Göttingen Germany). Beads were incubated for 5 min under rotation (low speed tumbling) and the supernatant was discarded. Elution was performed using 10 ml of 1 mM biotin solution (IBA GmbH). FACS analysis was carried out using a CytoFLEX flow cytometer (Beckman Coulter) with CD4-FITC and CD45-APC antibodies (both from BioLegend). The enrichment of CD4+ target cells from PBMCs is shown in FIG. 9 as dot plots (A) and bar chart (B) of the starting fraction, washing/depleted fraction and positive fraction and the enrichment of CD4+ cells from whole blood in FIGS. 9C and D. Erythrocytes were excluded from the FACS analysis of the positive fractions using CD45 gating. The yield of the method using Strep-Tactin®/dextran polymers was 1.5 times higher as compared to the positive fraction of the method without dextran polymer.

Example 8: Enrichment of Exosomes

Exosomes were isolated from body fluid such as a blood sample using the Strep-Tactin®/dextran polymer combined with moving batch mode. In particular, 10 ml of human buffy coat was diluted with buffer CI and centrifuged for 10 min at 3500 g to remove cells and cellular debris. The supernatant was used for immunaffinity purification using the FABian® device in the moving batch mode as described in the IBA GmbH Webpage "Cell Selection & Expansion" under "hCD14 short program", by using agarose beads coated with CD81 and CD9 antigen, respectively, and Strep-Tactin®/dextran polymers loaded with Strep®-tagged CD81 Fab and CD9 Fab, respectively.

Nanoparticle tracking analysis (NTA) was used to determine size distribution, concentration and absorption intensities of particles (FIG. 12A-C). Particles from human buffy coat in FIG. 12A were immuno-affinity purified with Fab against the tetraspanin CD81. Data of 5 technical NTA replicates reveal a size distribution from 80 to about 500 nm with a majority of particles in the range of 100 to 200 nm. The overall concentration of the CD81-selected particles is 3×10$^8$ per ml. The intensity plot (small insert in FIG. 12A) displays the individual recording events for all particles, which include all CD81+ particles, such as exosomes, membrane shedding, microvesicles and other EVs. Particles in FIG. 12B were further processed by size exclusion chromatography with a selective range of 30 to 200 nm to remove Fab, biotin and particles >200 nm. The resulting size distribution of particles in the column's void volume ranges from 60 to <300 nm with the vast majority of events between 80 and 150 nm, representing the approximate size of exosomes. The concentration of exosomes was >1.3×10$^8$ particles/ml representing about 40% of all isolated CD81-positive vesicles. In order to exclude possible impurities from particles in the PBS that was used during the assay, NTA of buffer was performed as negative control (FIG. 12C). Buffers are routinely passed through a 0.22 µm cellulose-acetate filter to eliminate impurities. The isolated particles have been further analysed by Immunoblot revealing the identity of purified particles as exosomes (FIG. 12D). Particles were subjected to SDS PAGE and transferred to PVDF or nitrocellulose membranes. A pre-purification sample (input) was used as a positive control. The blots were hybridized with an antibody against the tetraspanin CD63, which is a prominent exosome marker. Four individual purification procedures with Fab selecting CD9 or CD81 positive particles resulted in CD63 positive blots, strongly indicating a successful collection of exosomes, and CD9/CD81-positive extracellular vesicles, respectively.

Example 9: Enrichment of CD3+ Cells from Human PBMCs Using the Strep-Tactin®/Dextran Polymer Combined with Moving Batch Mode in the FABian® Device Using Biotin Coated Agarose Beads As a further development for the use of the Strep-Tactin®/dextran polymer, different beads in comparison to those as described in Examples 6 and 7 have been used. In particular, agarose beads have been used that have biotin residues coupled to its surface (IBA GmbH, Göttingen, Germany, Catalogue number: 6-0446-000). Furthermore, Strep-Tactin®/dextran polymers were used, wherein the dextran had an average MW of 2.05 Mio Da (Pharmacosmos A7S, Denmark). During this experiment, CD3+ cells were isolated via the use of CD3 Strep-tagged Fab fragments (IBA GmbH) and essentially the same components for cell isolation have been used as described in Example 8 and the moving batch mode has been applied as described in Example 7. Thus, for the purification of CD3+ cells from human PBMCs, the above-mentioned agarose-biotin beads with 90 µm average diameter (+/−50 µm) and Strep-Tactin®/dextran polymers loaded with Strep®-tagged CD3 Fab were used. In particular, prior to the use in the FABian® device, 1 ml biotin coated beads were incubated with 200 µg Strep-Tactin®/ dextran polymers for 5 minutes under gentle shaking, then loaded into a 15 ml column (Biocomma, China) with a 90 µm frit at the bottom for processing in the FABian® device as described in Example 8. About 200 µg anti-human CD3 Strep®-tagged Fab fragments (IBA GmbH, Göttingen, Germany) were used within the instrument for binding to the Strep-Tactin®/dextran polymers to occupy free binding sites on the Strep-Tactin® not bound to biotin residues on the agarose beads.

Afterwards, 5 ml of PBMCs ($2.48 \times 10^7$ cells) were added to the column and incubated for 10 min under rotation at the lowest speed (one revolution per second; tumbling roller mixer, RM5, A. Hartenstein) by putting an upper and bottom cap on the column. After removing the top cap and the cap at the outlet of the column, unbound cells were drained via gravity. The beads were washed two times with 10 ml washing buffer (IBA GmbH, Göttingen Germany). Beads were incubated for 5 min under rotation (low speed tumbling) and the supernatant was discarded. Elution was performed using 10 ml of 1 mM biotin solution (IBA GmbH).

Figure 14:
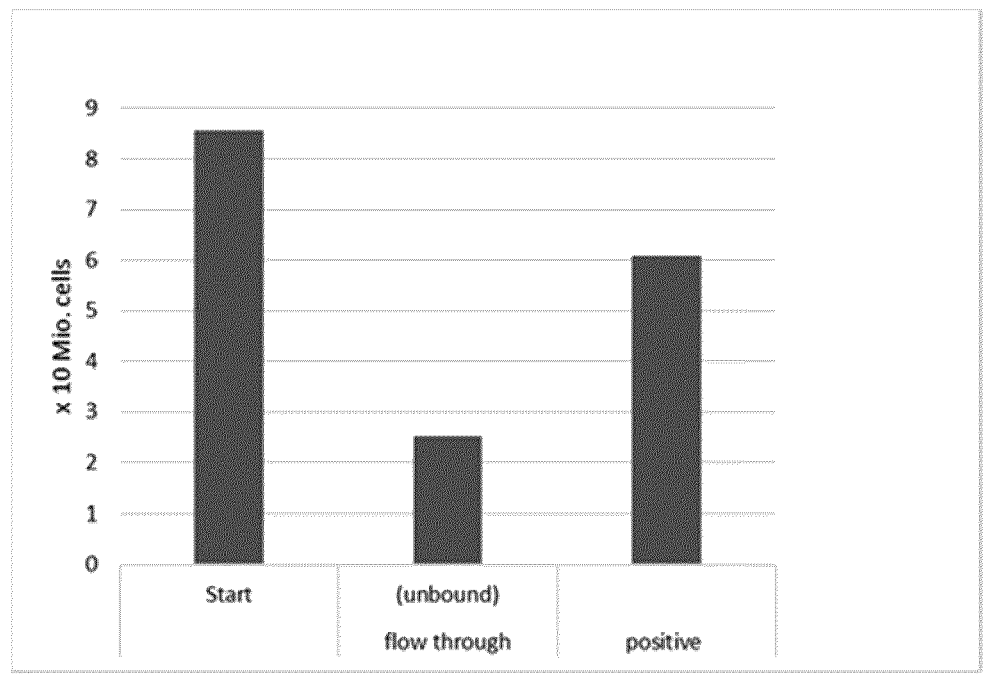
FIG. 14: FACS analyses of CD3+ cells enriched from human PBMCs via the Strep-Tactin®/dextran polymer combined with the "moving batch mode" in the FABian® device with biotin coated agarose beads shown as bar chart.

FACS analysis was carried out using a CytoFLEX flow cytometer (Beckman Coulter, Brea, California, USA) with CD3-APC and CD45-PerCP/Cy5.5 antibodies (both from BioLegend, San Diego, California, USA). The enrichment of CD3$^+$ cells is shown in FIG. 14 as bar char and the experiment was performed with a purity of up to 79%.

This method has the advantage that no Strep-tagged recombinant antigen is needed on the beads but that biotin agarose, a common and commercially available product, can be used. As explained with regard to FIG. 13, the Strep-Tactin®/dextran polymer after binding to the biotin agarose has still enough free binding sites to bind CD3 Fab fragments that can bind CD3$^+$ cells and can be eluted with a biotin solution.

In this experiment which corresponds to the schematic representation depicted in FIG. 13, the biological entity (1) is a CD3$^+$ cell, i.e. the antigen (2) is CD3. The procedure comprises a carrier (11) which is high molecular weight dextran having at least two ligand binding partners (7), i.e. Strep-Tactin® covalently coupled thereto. The tagging agent (3) is an anti-human CD3 Strep-tagged Fab fragment, wherein the binding domain (4) is a CD3 Fab fragment and the ligand (5) being part of the protein-ligand-interaction is a Strep-tag. The tagging agent (3) is immobilized on the Strep-Tactin®/dextran carrier (11) via a non-covalent protein-ligand interaction (8) between the Strep-tag (5) and the Strep-Tactin® (7). The tagging agent (3) binds the CD3 antigen (2) on the biological entity. The beads (6) are coated with the further ligand (12a), i.e. biotin which is bound by the ligand binding partner (7), i.e. Strep-Tactin® of the Strep-Tactin®/dextran polymer.

Example 10: Enrichment of Exosomes from Human Serum Using the Strep-Tactin®/Dextran Polymer Combined with Moving Batch Mode in the FABian® Device Using Biotin Coated Agarose Beads Exosomes were isolated from human serum (pooled from young male donors obtained from blood from a blood bank) using the Strep-Tactin®/dextran polymer, wherein the dextran had an average MW of 2.05 Mio Da (Pharmacosmos A7S, Denmark), combined with moving batch mode and biotin coated agarose beads. In particular, 4.25 ml serum, which was pre-filtered with 0.22 µm polyethylensulfone (PES) filters (Sartorius AG, Göttingen, Germany), was diluted 1:1 with PBS and centrifuged for 30 min at 12 000×g to remove cell debris. The supernatant was used for immunaffinity purification using the FABian® device in the moving batch mode as described in Example 8 by using 1 ml biotin coated agarose beads and Strep-Tactin®/dextran polymers loaded with Strep®-tagged CD81 Fab. In particular, prior to the use in the FABian® device, the beads were incubated with 100 µg Strep-Tactin®/dextran polymers for 5 min under gentle shaking, then loaded into a column for processing in the FABian® device. About 50 µg Strep®-tagged Fab antibodies directed against CD81 were used within the instrument for binding to the Strep-Tactin®/dextran polymers to occupy free binding sites on the Strep-Tactin® not bound to biotin residues on the agarose beads.

Figure 15:
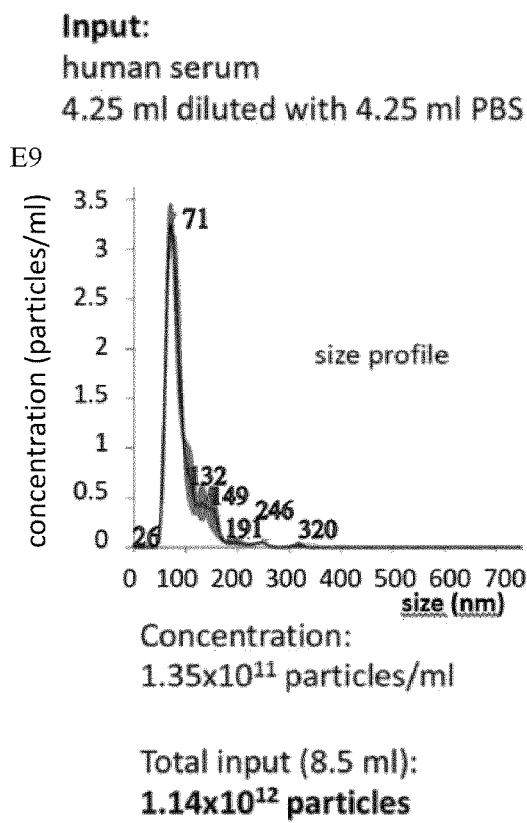
FIG. 15: Analysis of extracellular vesicles including exosomes purified via a Strep-Tactin®/dextran polymer using the "moving batch mode" of the FABian® device and biotin coated agarose beads. Nanoparticle tracking analysis (NTA) was used to determine size distribution, concentration and absorption intensities of particles. Particles from human serum (A) were immuno-affinity purified with Fab against the tetraspanin CD81. Data of 3 technical NTA replicates reveal a size distribution from 50 to about 500 nm with a majority of particles in the range of 50 to 200 nm (B).
Figure 15:
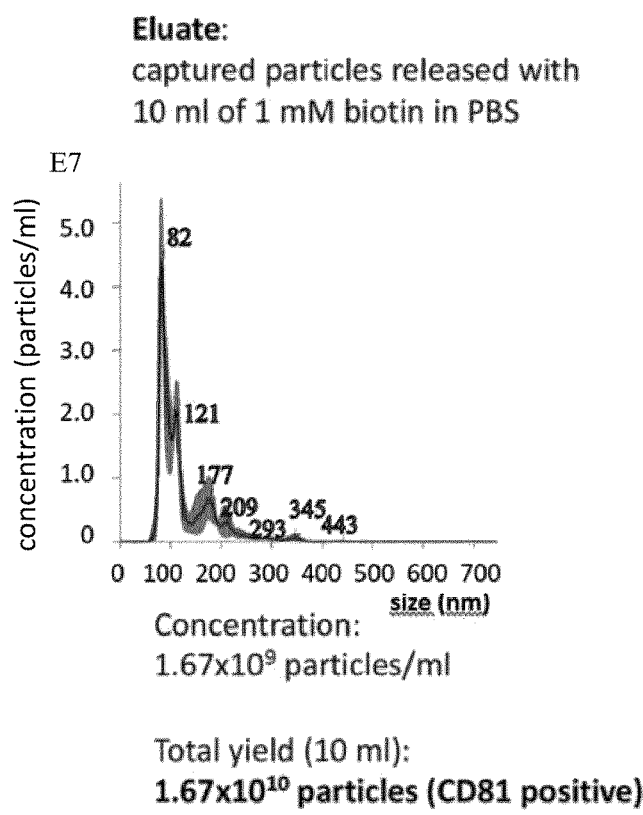

Nanoparticle tracking analysis (NTA) was used to determine size distribution, concentration and absorption intensities of particles as was performed as described in Example 8. The results from three individual measurements are shown in FIG. 15. The resulting particle concentration in the eluate after releasing bound exosomes from the beads was $1.7 \times 10^9$ per ml and the NTA analysis revealed a size distribution from 50 to about 500 nm with a majority of particles in the range of 50 to 200 nm.

The verification that indeed exosomes have been purified can be performed with size exclusion chromatography and Immunoblot as explained with regard to Example 8. Altogether the results showed that isolation of CD81$^+$ exosomes on biotin agarose using the Strep-Tactin®/dextran polymers works with good yields.

In this experiment which corresponds to the schematic representation depicted in FIG. 13, the biological entity (1) is an exosome, i.e. the antigen (2) is in this case CD81. The procedure comprises a carrier (11) which is high molecular weight dextran having at least two ligand binding partners (7), i.e. Strep-Tactin® covalently coupled thereto. The tagging agent (3) is an anti-human CD81 Strep-tagged Fab fragment, wherein the binding domain (4) is a CD81 Fab fragment and the ligand (5) being part of the protein-ligand-interaction is a Strep-tag. The tagging agent (3) is immobilized on the Strep-Tactin®/dextran carrier (11) via a non-covalent protein-ligand interaction (8) between the Strep-tag (5) and the Strep-Tactin® (7). The tagging agent (3) binds the CD81 antigen (2) on the biological entity, i.e. the exosome. The beads (6) are coated with the further ligand (12a), i.e. biotin which is bound by the ligand binding partner (7), i.e. Strep-Tactin® of the Strep-Tactin®/dextran polymer.

REFERENCE SIGNS 1 biological entity
2 surface antigen
2' recombinant antigen
3 tagging agent
3' bivalent tagging agent
4 binding domain
5 ligand
6 (particle) bead
7 ligand binding partner
8 non-covalent protein-ligand interaction
9 antigen recognition interaction
10 linking molecule
11 carrier
1212a (further) ligand
13 (further) ligand binding partner

The invention claimed is:

1. A method of isolating a biological entity from a sample comprising:
   (i) providing a sample comprising the biological entity (1), wherein the biological entity comprises a surface antigen (2);
   (ii) providing a first tagging agent (3) comprising at least one binding domain (4) and a ligand (5), wherein the binding domain (4) is capable of specifically binding to the surface antigen (2) on the biological entity via a first antigen recognition interaction (9);
   (iii) providing a carrier (11) comprising a first ligand binding partner (7) and a second ligand binding partner (7), wherein the first ligand binding partner (7) is capable of forming a first non-covalent protein-ligand interaction (8) with the ligand (5) of the first tagging agent (3);
   (iv) providing a second tagging agent (3) comprising a ligand (5) and at least one binding domain (4), wherein the ligand (5) is capable of forming a second non-covalent protein-ligand interaction (8) with the second ligand binding partner (7) of the carrier (11);
   (v) providing a linking molecule (10) comprising an antigen (2') and a ligand (5), wherein the antigen (2') is capable of specifically binding to the binding domain (4) of the second tagging agent (3) via a second antigen recognition interaction (9); and
   (vi) providing freely movable beads (6), wherein the beads (6) are non-magnetic beads, and wherein the beads comprise a third ligand binding partner (7) capable of forming a third non-covalent protein-ligand interaction (8) with the ligand (5) of the linking molecule (10);
   (vii) incubating the sample, the first tagging agent (3), the carrier (11), the second tagging agent (3), the linking molecule (10) and the beads (6) within a container and allowing complex formation between the biological entity (1), the first tagging agent (3) specifically bound to the biological entity (1) via the first antigen recognition interaction (9), the carrier (11) immobilizing the first tagging agent (3) via the first non-covalent protein-ligand interaction (8), the second tagging agent (3) immobilized on the carrier (11) via the second non-covalent protein-ligand interaction (8), the linking molecule (10) specifically bound to the second tagging agent (3) via the second antigen recognition interaction (9), and the beads (6) immobilizing the linking molecule (10) via the third non-covalent protein-ligand interaction (8); and
   (viii) purifying the biological entity (1) by temporarily holding the beads (6) in place in the container, while discarding the supernatant, and adding a washing buffer; and/or
   (ix) isolating the biological entity (1) by releasing the biological entity (1) from the beads (6) and the tagging agent (3), respectively, and recovery of the biological entity (1) from the supernatant while temporarily holding the beads (6) in place in the container, optionally allowing for the recovery of the first and second tagging agents (3) and/or beads (6).

2. The method of claim 1, wherein:
   (a) the binding domain (4) is present in an antigen-binding fragment (Fab); and/or
   (b) the first to third ligand binding partners (7) comprise streptavidin or a functionally analog or derivative thereof, and the ligand (5) comprises a streptavidin binding peptide.

3. The method of claim 1, wherein the first to third ligand binding partners (7) are a streptavidin mutein comprising the amino acid sequence Val$^{44}$-Thr$^{45}$-Ala$^{46}$-Arg$^{47}$ represented by SEQ ID NO: 13 or Ile$^{44}$-Gly$^{45}$-Ala$^{46}$-Arg$^{47}$ represented by SEQ ID NO: 14, and the ligand (5) is a streptavidin-binding peptide comprising one of the following sequences:
   a) -Trp-Xaa-His-Pro-Gln-Phe-Yaa-Zaa- represented by SEQ ID NO: 1, wherein Xaa is any amino acid and Yaa and Zaa are both Gly or Yaa is Glu and Zaa is Lys or Arg,
   b) -Trp-Arg-His-Pro-Gln-Phe-Gly-Gly- represented by SEQ ID NO: 2,
   c) -Trp-Ser-His-Pro-Gln-Phe-Glu-Lys- represented by SEQ ID NO: 3,
   d) a sequential arrangement of at least two streptavidin binding peptides, wherein each peptide binds streptavidin, wherein the distance between two peptides is at least 0 and not greater than 50 amino acids and wherein each of the at least two peptides comprises the amino acid sequence -His-Pro-Baa- in which Baa is selected from the group consisting of glutamine, asparagine and methionine, and wherein the sequential arrangement comprises at least the amino acid sequence -His-Pro-Baa-Xaa-His-Pro-Baa- (SEQ ID NO: 21), in which Xaa can be 0-50 amino acids of any type, and in which Baa is selected from the group consisting of glutamine, asparagine and methionine,
   e) a sequential arrangement as recited in d), wherein one of the at least two peptides comprises the sequence -His-Pro-Gln-, and wherein the sequential arrangement comprises at least the amino acid sequence -His-Pro- Gln-Xaa-His-Pro-Gln- (SEQ ID NO: 22), in which Xaa can be 0-50 amino acids of any type, f) a sequential arrangement as recited in d), wherein one of the peptides comprises an amino acid sequence -His-Pro-Gln-Phe- represented by SEQ ID NO: 4, and wherein the sequential arrangement comprises at least the amino acid sequence -His-Pro-Gln-Phe-Xaa-His-Pro-Gln-Phe-(SEQ ID NO: 23), in which Xaa can be 0-50 amino acids of any type, g) a sequential arrangement as recited in d) wherein at least one peptide includes at least the amino sequence -Oaa-Xaa-His-Pro-Gln-Phe-Yaa-Zaa- represented by SEQ ID NO: 5, wherein Oaa is Trp, Lys or Arg, Xaa is any amino acid and wherein either Yaa and Zaa are both Gly or Yaa is Glu and Zaa is Lys or Arg, and wherein the sequential arrangement comprises at least the amino acid sequence -Oaa-Xaa-His-Pro-Gln-Phe-Yaa-Zaa-Xaa-Oaa-Xaa-His-Pro-Gln-Phe-Yaa-Zaa-(SEQ ID NO: 24), in which Xaa at position 9 can be 0-50 amino acids of any type, where Oaa is Trp, Lys or Arg, Xaa at position 2 and 11 is any amino acid, and where either Yaa and Zaa are both Gly or Yaa is Glu and Zaa is Lys or Arg, h) a sequential arrangement as recited in d) wherein at least one peptide includes at least the amino acid sequence -Trp-Xaa-His-Pro-Gln-Phe-Yaa-Zaa- represented by SEQ ID NO: 6 wherein Xaa is any amino acid and wherein either Yaa and Zaa are both Gly or Yaa is Glu and Zaa is Lys or Arg, and wherein the sequential arrangement comprises at least the amino acid sequence -Trp-Xaa-His-Pro-Gln-Phe-Yaa-Zaa-Xaa-Trp-Xaa-His-Pro-Gln-Phe-Yaa-Zaa-(SEQ ID NO: 25), in which Xaa at position 9 can be 0-50 amino acids of any type, where Xaa at position 2 and 11 is any amino acid, and where either Yaa and Zaa are both Gly or Yaa is Glu and Zaa is Lys or Arg, i) a sequential arrangement as recited in d) wherein at least one peptide includes at least the amino acid sequence -Trp-Ser-His-Pro-Gln-Phe-Glu-Lys- represented by SEQ ID NO: 7, and wherein the sequential arrangement comprises at least the amino acid sequence -Trp-Ser-His-Pro-Gln-Phe-Glu-Lys-Xaa-Trp-Ser-His-Pro-Gln-Phe-Glu-Lys-(SEQ ID NO: 26), in which Xaa can be 0-50 amino acids of any type, j) the amino acid sequence -Trp-Ser-His-Pro-Gln-Phe-Glu-Lys-(Xaa)n-Trp-Ser-His-Pro-Gln-Phe-Glu-Lys- represented by SEQ ID NO: 8 wherein Xaa is any amino acid and n is an integer from 0 to 12, k) an amino acid sequence selected from the group consisting of Trp-Arg-His-Pro-Gln-Phe-Gly-Gly represented by SEQ ID NO: 2, Trp-Ser-His-Pro-Gln-Phe-Glu-Lys represented by SEQ ID NO: 9, Trp-Ser-His-Pro-Gln-Phe-Glu-Lys-(GlyGlyGlySer)$_3$-Trp-Ser-His-Pro-Gln-Phe-Glu-Lys represented by SEQ ID NO: 10, Trp-Ser-His-Pro-Gln-Phe-Glu-Lys-(GlyGlyGlySer)$_2$-Trp-Ser-His-Pro-Gln-Phe-Glu-Lys represented by SEQ ID NO: 11 and Trp-Ser-His-Pro-Gln-Phe-Glu-Lys-(GlyGlyGlySer)$_2$-Gly-Gly-Ser-Ala-Trp-Ser-His-Pro-Gln-Phe-Glu-Lys represented by SEQ ID NO: 12.

4. The method of claim 1, wherein the beads (6) are characterized to have a diameter of about 30-100 μm.

5. The method of claim 4, wherein the beads (6) are characterized to have a diameter of about 40-60 μm.

6. The method of claim 1, wherein the sample is introduced into and discharged from the container through the same opening and/or the beads (6) are held in place by a frit or sieve.

7. The method of claim 1, wherein the first and second tagging agents (3) are immobilized on the carrier (11) and wherein the linking molecule (10) is immobilized to the beads (6) prior to step (vii).

8. The method of claim 1, wherein the carrier (11) is a dextran polymer having an average molecular weight of about 500 kDa to 3,000 kDa and comprises at least two molecules of the ligand binding partner (7), which is capable of binding the tagging agent (3) comprising the ligand (5).

9. The method of claim 8, wherein the dextran polymer has an average molecular weight of about 1,500 kDa to 2,500 kDa.

10. The method of claim 8, wherein the at least two molecules of the ligand binding partner (7) are covalently bound streptavidin or an analog or derivative thereof.

11. The method of claim 1, wherein, in step (ix), the biological entity (1) is released by adding a competing ligand, optionally which leads to the release of the tagging agent (3) from the antigen (2, 2') and/or the ligand binding partner (7).

12. The method of claim 1, wherein the sample is a body fluid, and/or the biological entity is a cell, nucleus or a membrane-vesicle.

13. The method of claim 12, wherein the body fluid is blood or umbilical cord blood.

14. The method of claim 12, wherein the membrane-vesicle is a cell-derived membrane vesicle.

15. The method of claim 12, wherein the membrane-vesicle is an exosome.

16. The method of claim 1, wherein the container is a tube, vial, syringe, ampule, or column.

17. The method of claim 1, wherein the beads are agarose beads.

18. A kit for use in the method of claim 1, the kit comprising the first and second tagging agents (3), the beads (6), the carrier (11), the linking molecule (10), washing buffer and/or competing agent.

19. A dextran polymer having an average molecular weight of 3,000,000 Da for use in the method of claim 1 as the carrier (11), wherein the dextran polymer comprises at least two molecules of covalently bound streptavidin (7) or an analog or derivative thereof, which is capable of binding the first and second tagging agents (3) comprising a ligand (5), wherein the ligand (5) is a streptavidin binding peptide.

20. The dextran polymer of claim 19, wherein the ligand (5) is a streptavidin binding peptide comprising one of one of the following sequences:

a) -Trp-Xaa-His-Pro-Gln-Phe-Yaa-Zaa- represented by SEQ ID NO: 1, wherein Xaa is any amino acid and Yaa and Zaa are both Gly or Yaa is Glu and Zaa is Lys or Arg, b) -Trp-Arg-His-Pro-Gln-Phe-Gly-Gly- represented by SEQ ID NO: 2, c) -Trp-Ser-His-Pro-Gln-Phe-Glu-Lys- represented by SEQ ID NO: 3, d) a sequential arrangement of at least two streptavidin binding peptides, wherein each peptide binds streptavidin, wherein the distance between two peptides is at least 0 and not greater than 50 amino acids and wherein each of the at least two peptides comprises the amino acid sequence -His-Pro-Baa- in which Baa is selected from the group consisting of glutamine, asparagine and methionine, e) a sequential arrangement as recited in d), wherein one of the at least two peptides comprises the sequence -His-Pro-Gln-, f) a sequential arrangement as recited in d), wherein one of the peptides comprises an amino acid sequence -His-Pro-Gln-Phe- represented by SEQ ID NO: 4, g) a sequential arrangement as recited in d) wherein at least one peptide includes at least the amino sequence -Oaa-Xaa-His-Pro-Gln-Phe-Yaa-Zaa- represented by SEQ ID NO: 5, wherein Oaa is Trp, Lys or Arg, Xaa is any amino acid and wherein either Yaa and Zaa are both Gly or Yaa is Glu and Zaa is Lys or Arg, h) a sequential arrangement as recited in d) wherein at least one peptide includes at least the amino acid sequence -Trp-Xaa-His-Pro-Gln-Phe-Yaa-Zaa- represented by SEQ ID NO: 6 wherein Xaa is any amino acid and wherein either Yaa and Zaa are both Gly or Yaa is Glu and Zaa is Lys or Arg, i) a sequential arrangement as recited in d) wherein at least one peptide includes at least the amino acid sequence -Trp-Ser-His-Pro-Gln-Phe-Glu-Lys- represented by SEQ ID NO: 7, j) the amino acid sequence -Trp-Ser-His-Pro-Gln-Phe-Glu-Lys-(Xaa)n-Trp-Ser-His-Pro-Gln-Phe-Glu-Lys- represented by SEQ ID NO: 8 wherein Xaa is any amino acid and n is an integer from 0 to 12, k) an amino acid sequence selected from the group consisting of Trp-Arg-His-Pro-Gln-Phe-Gly-Gly represented by SEQ ID NO: 2, Trp-Ser-His-Pro-Gln-Phe-Glu-Lys represented by SEQ ID NO: 9, Trp-Ser-His-Pro-Gln-Phe-Glu-Lys-(GlyGlyGlySer)$_3$-Trp-Ser-His-Pro-Gln-Phe-Glu-Lys represented by SEQ ID NO: 10, Trp-Ser-His-Pro-Gln-Phe-Glu-Lys-(GlyGlyGlySer)$_2$-Trp-Ser-His-Pro-Gln-Phe-Glu-Lys represented by SEQ ID NO: 11 and Trp-Ser-His-Pro-Gln-Phe-Glu-Lys-(GlyGlyGlySer)$_2$-Gly-Gly-Ser-Ala-Trp-Ser-His-Pro-Gln-Phe-Glu-Lys represented by SEQ ID NO: 12.

* * * * *